US006403783B1

(12) United States Patent
Sheppard et al.

(10) Patent No.: US 6,403,783 B1
(45) Date of Patent: Jun. 11, 2002

(54) NUCLEIC ACID WHICH ENCODES THE TUMOR MARKER ZSIG62

(75) Inventors: Paul O. Sheppard, Granite Falls; Julia E. Novak, Bainbridge Island; Fenella Raymond, Seattle, all of WA (US)

(73) Assignee: ZymoGenetics, Inc., Seattle, WA (US)

( * ) Notice: Subject to any disclaimer, the term of this patent is extended or adjusted under 35 U.S.C. 154(b) by 0 days.

(21) Appl. No.: 09/493,565

(22) Filed: Jan. 18, 2000

Related U.S. Application Data

(60) Provisional application No. 60/116,321, filed on Jan. 19, 1999.

(51) Int. Cl.[7] .................... C07H 21/04; C07H 21/02; C12N 15/00; C12N 15/09; C12N 15/63
(52) U.S. Cl. ................ 536/23.5; 536/23.1; 435/320.1; 435/69.1; 435/325; 435/348; 435/349; 435/410; 435/254.1; 435/254.2
(58) Field of Search ..................... 536/23.5, 23.1; 435/320.1, 325, 69.1, 348, 349, 410, 243, 252.1, 254.1, 254.2

(56) References Cited

PUBLICATIONS

Alberts et al., Molecular Biology of the Cell, pp. 465, 1994.*
McClean et al., Eur. Journal of Cancer, vol. 29A, No. 16, pp 2243–2248, 1993.*
Fu et al., The EMBO Journal vol. 15. No. 16, pp 4392–4401, 1996.*
Shantz et al., The International Journal of Biochemistry & Cell Biology, vol. 31, pp. 107–122.*
Sequence from Incyte Pharmaceuticals, Inc., (No. INC4644734).
Sequence from Incyte Pharmaceuticals, Inc., (No. INC5272455).

* cited by examiner

*Primary Examiner*—Anthony C. Caputa
*Assistant Examiner*—Jennifer Hunt
(74) *Attorney, Agent, or Firm*—Phillip B. C. Jones

(57) ABSTRACT

Studies indicate that mutations in tumor suppressor genes occur early in the process of carcinogenesis, and that these mutations are correlated with a subsequent development of cancer. The detection of such alterations would provide useful molecular markers for diagnosis, surveillance, early tumor identification and intervention, and prognosis. A novel human gene, designated as "Zsig62," resides within a region of chromosome 16*q* that is associated with prostate and breast cancer, and that appears to contain tumor suppressor genes. Like a tumor suppressor gene, the Zsig62 gene is expressed in particular normal tissues, but not in tumors derived from those tissues.

27 Claims, No Drawings

SEQUENCE LISTING

<160> NUMBER OF SEQ ID NOS: 8

<210> SEQ ID NO 1
<211> LENGTH: 2334
<212> TYPE: DNA
<213> ORGANISM: Homo sapiens
<220> FEATURE:
<221> NAME/KEY: CDS
<222> LOCATION: (20)...(316)

<400> SEQUENCE: 1

```
caggtcatgt cattccaga atg tgt tgc tgg cct tct cca tgg gtg cag gga        52
                    Met Cys Cys Trp Pro Ser Pro Trp Val Gln Gly
                     1               5                  10 agc cct ggc att tgg cat ttg tgg gca gtg ttg gcg tgc cac ctg ggt       100
Ser Pro Gly Ile Trp His Leu Trp Ala Val Leu Ala Cys His Leu Gly
             15                  20                  25 cac agc agc agc agg cag gga atc ctg aga cat cgc cct ggg gga gcc       148
His Ser Ser Ser Arg Gln Gly Ile Leu Arg His Arg Pro Gly Gly Ala
         30                  35                  40 ctg cct tct acc cca ggc tgt aca atg acg agt act ctt gga caa aga       196
Leu Pro Ser Thr Pro Gly Cys Thr Met Thr Ser Thr Leu Gly Gln Arg
     45                  50                  55 ccc ctc ttg caa ggc tgc gag gac atc atg gtc cag ccc gag gga gat       244
Pro Leu Leu Gln Gly Cys Glu Asp Ile Met Val Gln Pro Glu Gly Asp
 60                  65                  70                  75 tta tct ttg att gtc ttg agt gct gca tca gct aag aca aaa acc aca       292
Leu Ser Leu Ile Val Leu Ser Ala Ala Ser Ala Lys Thr Lys Thr Thr
                 80                  85                  90 gag tca gag gga aaa aaa acg tcc tgatgaggat tgtgcaattt ccggaccatc      346
Glu Ser Glu Gly Lys Lys Thr Ser
                 95 atttttaaa aattataaat tatgaaatcc cacattttca atcccaattt ctggaacgtg      406
ttttattttg agcacagaat ggcaacatcc caggaaaaaa agtcatgctc ccattttgct     466
tgtaatcaag tgagctggaa ctgaccctac cccaaatatt ttttgaatag ggaaaagact     526
caactggacc cctctaagga ctgggagctg gcatggagct ggcatcttct gagactgact     586
tgagaagagc ctgataacgc ctagaggaaa caggcagggt tttgcgagca ggggaagatg     646
atagtgggtg ggtggggagc tggcgagggt gccccaggca gaggcaccgt gtgtgtgcaa     706
aggcctgcag gtggagaagg gcctgggact cttggagaat ggcaggaagt ttggtgtgcc     766
tgtagtctat gagccaggct cagggcagca aaggtctgtc ctgcaggtgt tgtgatgagc     826
tgtaccactt agtgggcacc atcaagatga acagagagta acacggtggc actgagaact     886
tgagaacagc tcactctaga atgaactgtg tcctccaaag tgtgcagagc caatacctag     946
gggtccccaa ggtgactgag cacgggcaca gatccagcag caaatccccc cagtccaaga    1006
gctgttcttt ccattctctg ttctttccat tctctgttct tctggtcctt ctgcttatgg    1066
caaggtgaaa gtcacaggtg gaattgtccc tatcacctct cccacaccct gatctccttt    1126
tacaacaaag agcaagcatc ctctacaaca aagcctttgg ttggtgtcag tgcctggctg    1186
```

```
ggaggaagta actgttgttt ttactgtgtt taatttcact cctgccgtct gttcacggca    1246
ccagtgatca ggttctctgc cagtgggagt gatagaaagt tacctttta aagtaaattt    1306 cttggaacgc aaaaaacaag ccaagttaaa taaaaataca aaatatgggg ccaggcgcgg    1366
tggctcgtgc ctgtcatccc agcactttgg gaggctgaga cggtggatca cctgaggtca    1426
ggagtttgag accagcctga ccaacaaggt gaagcccgt ctctactaaa aatacaaaaa     1486
ttagccgggc gtggtggcag gcacctgtag tcccagctac tcgggaggct gggacagagg    1546
aattgcttga acccgggagg cggaggttgc agtgagccga gatcacgcca ccactgcact    1606
ccagcctggg tgacggagcg agatgccatt tcaaaacaaa aacaaaatat gtactggtac    1666
cagtacacag taggaaggtg ggcaaaactt gggaaggggg atattcaaag gacagggttt    1726
gggaaatgct ggatcaaggt cggggaagaa ggagaactga gaggctgtta taatttagag    1786
aagtgcttct cagagtgggg gccagcagcc aggcgccgtg gctcatgcct gtaaccttaa    1846
cactttggga ggtctaggcg ggaggattgc ctgagcccag gagttcgagt ccagcttgtg    1906
caacatagtg agatgctgtc tctacaaaaa atttaaaaat tagctggtgt cctctcagtg    1966
tgtcttgtcc tctccatgtt tctaaaataa aggaagaaag gcccagcgca gtggcgtaca    2026
cctatagtct cagcactttg ggaggccaag gtgggcagat cacttgaggt caggagttcg    2086
agaccagcct ggctaacatg gcaaaacctt gtttctactg gaaatacaaa aattagctag    2146
gcgtggtggt gcacgcctgt aatcccagct acttgggagg ctgagggagg agaaccgctt    2206
gagcctggga ggcagaggct gcagtgagcc aagatcacac actgcactcc agcctgggtg    2266
acagagcgag actccatctc aaataaataa ataaataaat aaaaataaat acataaatac    2326
ataaaata                                                              2334
```

<210> SEQ ID NO 2
<211> LENGTH: 99
<212> TYPE: PRT
<213> ORGANISM: Homo sapiens

<400> SEQUENCE: 2

Met Cys Cys Trp Pro Ser Pro Trp Val Gln Gly Ser Pro Gly Ile Trp
1               5                   10                  15

His Leu Trp Ala Val Leu Ala Cys His Leu Gly His Ser Ser Ser Arg
            20                  25                  30

Gln Gly Ile Leu Arg His Arg Pro Gly Gly Ala Leu Pro Ser Thr Pro
        35                  40                  45

Gly Cys Thr Met Thr Ser Thr Leu Gly Gln Arg Pro Leu Leu Gln Gly
    50                  55                  60

Cys Glu Asp Ile Met Val Gln Pro Glu Gly Asp Leu Ser Leu Ile Val
65                  70                  75                  80

Leu Ser Ala Ala Ser Ala Lys Thr Lys Thr Thr Glu Ser Glu Gly Lys
                85                  90                  95

Lys Thr Ser

<210> SEQ ID NO 3
<211> LENGTH: 297
<212> TYPE: DNA
<213> ORGANISM: Artificial Sequence
<220> FEATURE:
<223> OTHER INFORMATION: This degenerate sequence encodes the amino acid
      sequence of SEQ ID NO:2.
<220> FEATURE:
<221> NAME/KEY: variation

```
<222> LOCATION: (1)...(297)
<223> OTHER INFORMATION: N is any nucleotide.

<400> SEQUENCE: 3
atgtgytgyt ggccnwsncc ntgggtncar ggnwsnccng gnathtggca yytntgggcn    60
gtnytngcnt gycayytngg ncaywsnwsn wsnmgncarg gnathytnmg ncaymgnccn   120
ggnggngcny tnccnwsnac nccnggntgy acnatgacnw snacnytngg ncarmgnccn   180
ytnytncarg gntgygarga yathatggtn carccngarg gngayytnws nytnathgtn   240
ytnwsngcng cnwsngcnaa racnaaracn acngarwsng arggnaaraa racnwsn     297

<210> SEQ ID NO 4
<211> LENGTH: 23
<212> TYPE: DNA
<213> ORGANISM: Artificial Sequence
<220> FEATURE:
<223> OTHER INFORMATION: PCR primer

<400> SEQUENCE: 4
ctgatgcagc actcaagaca atc                                          23

<210> SEQ ID NO 5
<211> LENGTH: 24
<212> TYPE: DNA
<213> ORGANISM: Artificial Sequence
<220> FEATURE:
<223> OTHER INFORMATION: PCR primer

<400> SEQUENCE: 5
ggcatttgtg ggcagtgttg gggc                                         24

<210> SEQ ID NO 6
<211> LENGTH: 18
<212> TYPE: DNA
<213> ORGANISM: Artificial Sequence
<220> FEATURE:
<223> OTHER INFORMATION: PCR primer

<400> SEQUENCE: 6
ggagctggca tcttctga                                                18

<210> SEQ ID NO 7
<211> LENGTH: 18
<212> TYPE: DNA
<213> ORGANISM: Artificial Sequence
<220> FEATURE:
<223> OTHER INFORMATION: PCR primer

<400> SEQUENCE: 7
tccccaccca cccactat                                                18

<210> SEQ ID NO 8
<211> LENGTH: 16
<212> TYPE: PRT
<213> ORGANISM: Artificial Sequence
<220> FEATURE:
<223> OTHER INFORMATION: Peptide linker

<400> SEQUENCE: 8

Gly Gly Ser Gly Gly Ser Gly Gly Gly Ser Gly Gly Gly Gly Ser
 1               5                  10                  15
```

NUCLEIC ACID WHICH ENCODES THE TUMOR MARKER ZSIG62

CROSS-REFERENCE TO RELATED APPLICATIONS

This application claims the benefit of U.S. Provisional application No. 60/116,321 (filed Jan. 19, 1999), the contents of which are incorporated by reference.

TECHNICAL FIELD

The present invention relates generally to a new polypeptide having diagnostic and therapeutic uses. In particular, the present invention relates to a novel tumor marker, designated "Zsig62," and to nucleic acid molecules encoding Zsig62.

BACKGROUND OF THE INVENTION

Cancer is a complex disease, often having a mixed etiology. Although environmental factors appear to play a dominant role in the development of certain cancers, it is also clear that genetic factors determine cancer susceptibility (for a review, see Cornelisse and Devilee, *Patient Education and Counseling* 32:9 (1997), Brandt-Rauf and Pincus, *Pharmacol. Ther.* 77:135 (1998), and Jameson, "Oncogenes and Tumor Suppressor Genes," in *Principles of Molecular Medicine,* Jameson (ed.), pages 73–82 (Humana Press, Inc. 1998)). Genetic changes can affect many aspects of cellular function, such as an increased rate of cellular proliferation, resistance to apoptosis, altered tissue invasiveness, production of growth and angiogenic factors, and the ability to avoid immune defenses.

For example, genetic alterations of oncogenes and tumor suppressor genes can be identified in a variety of human tumor tissues. Upon abnormal activation, the so-called "proto-oncogenes" can induce uncontrolled cellular proliferation. The products of proto-oncogenes include extracellular growth factors, transmembrane growth factor receptors, components of intracellular signal pathways, and components of the system that drives the cell division cycle and cellular self-destruction.

While proto-oncogenes are dominantly-acting genes, tumor suppressor genes act in a recessive manner. That is, both copies of a tumor suppressor gene must be inactivated to induce tumor growth. The inactivating mutations may be inherited in the germline, acquired by somatic mutation, or acquired by a combination of these events. The end result is that, when mutations inactivate both copies of tumor suppressor genes, normal inhibition of cellular growth is lost. Tumor suppressor genes include sequences that encode proteins involved in transcriptional regulation, cell cycle progression, and signaling pathways.

In certain cases, alterations in tumor suppressor genes are believed to occur early in the process of carcinogenesis and to be correlated with a subsequent development of cancer. The detection of such alterations would provide useful molecular markers for diagnosis, surveillance, early tumor identification and intervention, and prognosis. Yet the initial identification of a new tumor suppressor gene marker is difficult because mutations in these genes act recessively at the cellular level.

A need therefore exists for the identification of tumor suppressor genes that are involved in hereditary cancer syndromes.

BRIEF SUMMARY OF THE INVENTION

The present invention provides a novel gene, designated "Zsig62." The present invention also provides Zsig62 polypeptides and Zsig62 fusion proteins, nucleic acid molecules encoding such polypeptides and proteins, and methods for using these amino acid and nucleotide sequences.

DESCRIPTION OF THE INVENTION

1. Overview

The present invention provides nucleic acid molecules that encode a new human polypeptide that is expressed differently by certain normal and tumor tissues. An illustrative nucleic acid molecule containing a sequence that encodes the "Zsig62" polypeptide has the following nucleotide sequence:

```
CAGGTCATGT CATTCCAGAA TGTGTTGCTG GCCTTCTCCA TGGGTGCAGG  (SEQ ID NO:1).

GAAGCCCTGG CATTTGGCAT TTGTGGGCAG TGTTGGCGTG CCACCTGGGT

CACAGCAGCA GCAGGCAGGG AATCCTGAGA CATCGCCCTG GGGGAGCCCT

GCCTTCTACC CCAGGCTGTA CAATGACGAG TACTCTTGGA CAAAGACCCC

TCTTGCAAGG CTGCGAGGAC ATCATGGTCC AGCCCGAGGG AGATTTATCT

TTGATTGTCT TGAGTGCTGC ATCAGCTAAG ACAAAAACCA CAGAGTCAGA

GGGAAAAAAA ACGTCCTGAT GAGGATTGTG CAATTTCCGG ACCATCATTT

TTTAAAAATT ATAAATTATG AAATCCCACA TTTTCAATCC CAATTTCTGG

AACGTGTTTT ATTTTGAGCA CAGAATGGCA ACATCCCAGG AAAAAAAGTC

ATGCTCCCAT TTTGCTTGTA ATCAAGTGAG CTGGAACTGA CCCTACCCCA

AATATTTTTT GAATAGGGAA AAGACTCAAC TGGACCCCTC TAAGGACTGG

GAGCTGGCAT GGAGCTGGCA TCTTCTGAGA CTGACTTGAG AAGAGCCTGA

TAACGCCTAG AGGAAACAGG CAGGGTTTTG CGAGCAGGGG AAGATGATAG

TGGGTGGGTG GGGAGCTGGC GAGGGTGCCC CAGGCAGAGG CACCGTGTGT
```

-continued

```
GTGCAAAGGC CTGCAGGTGG AGAAGGGCCT GGGACTCTTG GAGAATGGCA

GGAAGTTTGG TGTGCCTGTA GTCTATGAGC CAGGCTCAGG GCAGCAAAGG

TCTGTCCTGC AGGTGTTGTG ATGAGCTGTA CCACTTAGTG GGCACCATCA

AGATGAACAG AGAGTAACAC GGTGGCACTG AGAACTTGAG AACAGCTCAC

TCTAGAATGA ACTGTGTCCT CCAAAGTGTG CAGAGCCAAT ACCTAGGGGT

CCCCAAGGTG ACTGAGCACG GCACAGATC CAGCAGCAAA TCCCCCCAGT

CCAAGAGCTG TTCTTTCCAT TCTCTGTTCT TTCCATTCTC TGTTCTTCTG

GTCCTTCTGC TTATGGCAAG GTGAAAGTCA CAGGTGGAAT TGTCCCTATC

ACCTCTCCCA CACCCTGATC TCCTTTTACA ACAAAGAGCA AGCATCCTCT

ACAACAAAGC CTTTGGTTGG TGTCAGTGCC TGGCTGGGAG GAAGTAACTG

TTGTTTTTAC TGTGTTTAAT TTCACTCCTG CCGTCTGTTC ACGGCACCAG

TGATCAGGTT CTCTGCCAGT GGGAGTGATA GAAAGTTACC TTTTTAAAGT

AAATTTCTTG GAACGCAAAA AACAAGCCAA GTTAAATAAA AATACAAAAT

ATGGGGCCAG GCGCGGTGGC TCGTGCCTGT CATCCCAGCA CTTTGGGAGG

CTGAGACGGT GGATCACCTG AGGTCAGGAG TTTGAGACCA GCCTGACCAA

CAAGGTGAAG CCCCGTCTCT ACTAAAAATA CAAAAATTAG CCGGGCGTGG

TGGCAGGCAC CTGTAGTCCC AGCTACTCGG GAGGCTGGGA CAGAGGAATT

GCTTGAACCC GGGAGGCGGA GGTTGCAGTG AGCCGAGATC ACGCCACCAC

TGCACTCCAG CCTGGGTGAC GGAGCGAGAT GCCATTTCAA AACAAAAACA

AAATATGTAC TGGTACCAGT ACACAGTAGG AAGGTGGGCA AAACTTGGGA

AGGGGGATAT TCAAAGGACA GGGTTTGGGA AATGCTGGAT CAAGGTCGGG

GAAGAAGGAG AACTGAGAGG CTGTTATAAT TTAGAGAAGT GCTTCTCAGA

GTGGGGGCCA GCAGCCAGGC GCCGTGGCTC ATGCCTGTAA CCTTAACACT

TTGGGAGGTC TAGGCGGGAG GATTGCCTGA GCCCAGGAGT TCGAGTCCAG

CTTGTGCAAC ATAGTGAGAT GCTGTCTCTA CAAAAAATTT AAAAATTAGC

TGGTGTCCTC TCAGTGTGTC TTGTCCTCTC CATGTTTCTA AAATAAAGGA

AGAAAGGCCC AGCGCAGTGG CGTACACCTA TAGTCTCAGC ACTTTGGGAG

GCCAAGGTGG GCAGATCACT TGAGGTCAGG AGTTCGAGAC CAGCCTGGCT

AACATGGCAA AACCTTGTTT CTACTGGAAA TACAAAAATT AGCTAGGCGT

GGTGGTGCAC GCCTGTAATC CCAGCTACTT GGGAGGCTGA GGGAGGAGAA

CCGCTTGAGC CTGGGAGGCA GAGGCTGCAG TGAGCCAAGA TCACACACTG

CACTCCAGCC TGGGTGACAG AGCGAGACTC CATCTCAAAT AAATAAATAA

ATAAATAAAA ATAAATACAT AAATACATAA AATA
```

The encoded polypeptide has the following amino acid sequence: MCCWPSPWVQ GSPGIWHLWA VLACHLGHSS SRQGILRHRP GGALPSTPGC TMTSTLGQRP LLQGCEDIMV QPEGDLSLIV LSAASAK-TKT TESEGKKTS (SEQ ID NO:2). Thus, the Zsig62 gene described herein encodes a polypeptide of 99 amino acids, as shown in SEQ ID NO:2.

Zsig62 contains a number of structural features, including a signal sequence at amino acid residues 1–31 of SEQ ID NO:2. For example, the Zsig62 protein has a predicted single disulfide bond at Cys50–Cys65. There is also a potential di-basic peptide cleavage site at Lys97. Cleavage at this site would remove amino acid residues 95 to 99, and Gly94 would be converted to an amide. Accordingly, Zsig62 can occur with an amidated C-terminus. In addition, the protein also contains a sequence which is similar to the typical N-terminal cleavage site found in members of the secretin-glucagon-vasoactive intestinal peptide hormone family: RH[SAN]D, wherein acceptable amino acids for a given position are indicated within square brackets (amino acid residues 37 to 40 of SEQ ID NO:2). Cleavage at this site would produce a polypeptide consisting of amino acid residues 39 to 99, while cleavage at both N-terminal and C-terminal sites would produce a polypeptide with an amidated C-terminus that consisted of amino acid residues 39 to 94.

A chromosomal localization study revealed that the Zsig62 gene resides on human chromosome 16 at 16q24.3. Mutations in this location are associated with various tumors, as described below.

Northern analyses demonstrated that expression of the Zsig62 gene is detectable in numerous tissues, such as placenta, spinal cord, total pituitary, prostate, while little or no Zsig62 gene expression was observed in samples obtained from adult brain, fetal brain, heart, kidney, liver, fetal lung, pancreas, skeletal muscle, spleen, testis, thymus, small intestine, colon, peripheral blood lymphocytes, esophageal tumor, normal esophagus, stomach tumor, normal stomach, lung tumor, and the Y-1A adrenal cell line. These results indicate that Zsig62 nucleotide sequences can be used to differentiate between various normal tissues. In addition, Zsig62 RNA was detected in tissue from lung, uterus, breast, fallopian tube, ovary, and gall bladder, while little or no Zsig62 gene expression was found in tumors derived from these organs. Thus, Zsig62 nucleotide sequences can be used to differentiate between normal and tumor tissues obtained from lung, uterus, breast, fallopian tube, ovary, and gall bladder.

As described herein, the present invention provides isolated polypeptides having an amino acid sequence that is at least 70%, at least 80%, or at least 90% identical to the amino acid sequence of SEQ ID NO:2, wherein such isolated polypeptides can specifically bind with an antibody that specifically binds with a polypeptide consisting of the amino acid sequence of SEQ ID NO:2. An illustrative polypeptide is a polypeptide that comprises the amino acid sequence of SEQ ID NO:2. Additional exemplary polypeptides include the following: (a) a polypeptide comprising the amino acid sequence of amino acid residues 32 to 99 of SEQ ID NO:2, (b) a polypeptide comprising the amino acid sequence of amino acid residues 32 to 94 of SEQ ID NO:2, wherein the last amino acid residue of the recited sequence is amidated, (c) a polypeptide comprising the amino acid sequence of amino acid residues 1 to 94 of SEQ ID NO:2, wherein the last amino acid residue of the recited sequence is amidated, (d) a polypeptide comprising the amino acid sequence of amino acid residues 39 to 99 of SEQ ID NO:2, and (e) a polypeptide comprising the amino acid sequence of amino acid residues 39 to 94 of SEQ ID NO:2, wherein the last amino acid residue of the recited sequence is amidated. Other illustrative polypeptides include polypeptides comprising the amino acid sequence of the following amino acid residues of SEQ ID NO:2: 1 to 94, 32 to 94, and 39 to 94, last amino acid residue of the recited sequence is not amidated.

The present invention also includes isolated polypeptides comprising at least 15, or at least 30, contiguous amino acid residues of an amino acid sequence of SEQ ID NO:2 selected from the group consisting of: (a) amino acid residues 1 to 99, (b) amino acid residues 32 to 99 of SEQ ID NO:2, (c) amino acid residues 32 to 94, (d) amino acid residues 1 to 94, (e) amino acid residues 39 to 99, (f) amino acid residues 39 to 94, and (g) an amino acid sequence of (c), (d), or (f), wherein the last amino acid residue of the recited sequence is amidated. Illustrative polypeptides include polypeptides that either comprise, or consist of, amino acid residues (a) to (g).

The present invention further provides antibodies and antibody fragments that specifically bind with such polypeptides. Exemplary antibodies include polyclonal antibodies, murine monoclonal antibodies, humanized antibodies derived from murine monoclonal antibodies, and human monoclonal antibodies. Illustrative antibody fragments include $F(ab')_2$, $F(ab)_2$, Fab', Fab, Fv, scFv, and minimal recognition units. The present invention further includes compositions comprising a carrier and a peptide, polypeptide, or antibody described herein.

The present invention also provides isolated nucleic acid molecules that encode a Zsig62 polypeptide, wherein the nucleic acid molecule is selected from the group consisting of (a) a nucleic acid molecule having the nucleotide sequence of SEQ ID NO:3, (b) a nucleic acid molecule encoding the amino acid sequence of SEQ ID NO:2, and (c) a nucleic acid molecule that remains hybridized following stringent wash conditions to a nucleic acid molecule having the nucleotide sequence of nucleotides 20–316 of SEQ ID NO: 1, or the complement of nucleotides 20–316 of SEQ ID NO: 1.

Illustrative nucleic acid molecules include those in which any difference between the amino acid sequence encoded by the nucleic acid molecule and the corresponding amino acid sequence of SEQ ID NO:2 is due to a conservative amino acid substitution. The present invention further contemplates isolated nucleic acid molecules that comprise a nucleotide sequence of nucleotides 20–316 of SEQ ID NO: 1.

The present invention also includes vectors and expression vectors comprising such nucleic acid molecules. Such expression vectors may comprise a transcription promoter, and a transcription terminator, wherein the promoter is operably linked with the nucleic acid molecule, and wherein the nucleic acid molecule is operably linked with the transcription terminator. The present invention further includes recombinant host cells comprising these vectors and expression vectors. Illustrative host cells include bacterial, yeast, fungal, insect, mammalian, and plant cells. Recombinant host cells comprising such expression vectors can be used to produce Zsig62 polypeptides by culturing such recombinant host cells that comprise the expression vector and that produce the Zsig62 protein, and, optionally, isolating the Zsig62 protein from the cultured recombinant host cells.

The present invention also contemplates methods for detecting the presence of Zsig62 RNA in a biological sample, comprising the steps of (a) contacting a Zsig62 nucleic acid probe under hybridizing conditions with either (i) test RNA molecules isolated from the biological sample, or (ii) nucleic acid molecules synthesized from the isolated RNA molecules, wherein the probe has a nucleotide sequence comprising a portion of the nucleotide sequence of nucleotides 20–316 of SEQ ID NO:1, or its complement, and (b) detecting the formation of hybrids of the nucleic acid probe and either the test RNA molecules or the synthesized nucleic acid molecules, wherein the presence of the hybrids indicates the presence of Zsig62 RNA in the biological sample. As an illustration, the biological sample can be a human biological sample. Exemplary tissues that can provide a biological sample include lung, uterus, breast, fallopian tube, ovary, and gall bladder.

The present invention further provides methods for detecting the presence of Zsig62 polypeptide in a biological sample, comprising the steps of: (a) contacting the biological sample with an antibody or an antibody fragment that specifically binds with a polypeptide consisting of the amino acid sequence of SEQ ID NO:2, wherein the contacting is performed under conditions that allow the binding of the antibody or antibody fragment to the biological sample, and (b) detecting any of the bound antibody or bound antibody fragment. Such an antibody or antibody fragment may further comprise a detectable label selected from the group consisting of radioisotope, fluorescent label, chemiluminescent label, enzyme label, bioluminescent label, and colloidal gold. An exemplary biological sample is a human biological sample, and examples of tissues that can provide a source of the biological sample include lung, uterus, breast, fallopian tube, ovary, and gall bladder.

The present invention also provides kits for performing these detection methods. For example, a kit for detection of Zsig62 gene expression may comprise a container that comprises a nucleic acid molecule, wherein the nucleic acid molecule is selected from the group consisting of (a) a nucleic acid molecule comprising the nucleotide sequence of nucleotides 20–316 of SEQ ID NO:1, (b) a nucleic acid molecule comprising the complement of nucleotides 20–316 of the nucleotide sequence of SEQ ID NO:1, (c) a nucleic acid molecule that is a fragment of (a) consisting of at least eight nucleotides, and (d) a nucleic acid molecule that is a fragment of (b) consisting of at least eight nucleotides. Such a kit may also comprise a second container that comprises one or more reagents capable of indicating the presence of the nucleic acid molecule. On the other hand, a kit for detection of Zsig62 protein may comprise a container that comprises an antibody, or an antibody fragment, that specifically binds with a polypeptide consisting of the amino acid sequence of SEQ ID NO:2.

The present invention also contemplates anti-idiotype antibodies, or anti-idiotype antibody fragments, that specifically bind an antibody or antibody fragment that specifically binds a polypeptide consisting of the amino acid sequence of SEQ ID NO:2.

The present invention further contemplates a method of detecting a tumor in a human subject, comprising the steps of: (a) contacting a Zsig62 nucleic acid probe under hybridizing conditions with a test sample that comprises either (i) RNA molecules isolated from a biological sample of the human subject, wherein the biological sample is suspected of containing tumor cells, or (ii) nucleic acid molecules synthesized from the isolated RNA molecules, wherein the nucleic acid probe has a nucleotide sequence comprising either a portion of the nucleotide sequence of nucleotides 20 to 316 of SEQ ID NO:1, or its complement, and wherein the biological sample is obtained from a tissue selected from the group consisting of lung, uterus, breast, fallopian tube, ovary, and gall bladder, and (b) detecting the formation of hybrids of the nucleic acid probe and the test sample, wherein the absence of hybrids indicates the presence of a tumor in the tissue obtained from the human subject.

In addition, the present invention provides fusion proteins that comprise a Zsig62 polypeptide moiety, and an immunoglobulin moiety, such as an immunoglobulin heavy chain constant region.

These and other aspects of the invention will become evident upon reference to the following detailed description. In addition, various references are identified below and are incorporated by reference in their entirety.

2. Definitions

In the description that follows, a number of terms are used extensively. The following definitions are provided to facilitate understanding of the invention.

As used herein, "nucleic acid" or "nucleic acid molecule" refers to polynucleotides, such as deoxyribonucleic acid (DNA) or ribonucleic acid (RNA), oligonucleotides, fragments generated by the polymerase chain reaction (PCR), and fragments generated by any of ligation, scission, endonuclease action, and exonuclease action. Nucleic acid molecules can be composed of monomers that are naturally-occurring nucleotides (such as DNA and RNA), or analogs of naturally-occurring nucleotides (e.g., α-enantiomeric forms of naturally-occurring nucleotides), or a combination of both. Modified nucleotides can have alterations in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like. The term "nucleic acid molecule" also includes so-called "peptide nucleic acids," which comprise naturally-occurring or modified nucleic acid bases attached to a polyamide backbone. Nucleic acids can be either single stranded or double stranded.

The term "complement of a nucleic acid molecule" refers to a nucleic acid molecule having a complementary nucleotide sequence and reverse orientation as compared to a reference nucleotide sequence. For example, the sequence 5' ATGCACGGG 3' is complementary to 5' CCCGTGCAT 3'.

The term "contig" denotes a nucleic acid molecule that has a contiguous stretch of identical or complementary sequence to another nucleic acid molecule. Contiguous sequences are said to "overlap" a given stretch of a nucleic acid molecule either in their entirety or along a partial stretch of the nucleic acid molecule.

The term "degenerate nucleotide sequence" denotes a sequence of nucleotides that includes one or more degenerate codons as compared to a reference nucleic acid molecule that encodes a polypeptide. Degenerate codons contain different triplets of nucleotides, but encode the same amino acid residue (i.e., GAU and GAC triplets each encode Asp).

The term "structural gene" refers to a nucleic acid molecule that is transcribed into messenger RNA (mRNA), which is then translated into a sequence of amino acids characteristic of a specific polypeptide.

An "isolated nucleic acid molecule" is a nucleic acid molecule that is not integrated in the genomic DNA of an organism. For example, a DNA molecule that encodes a growth factor that has been separated from the genomic DNA of a cell is an isolated DNA molecule. Another example of an isolated nucleic acid molecule is a chemically-synthesized nucleic acid molecule that is not integrated in the genome of an organism. A nucleic acid molecule that has been isolated from a particular species is smaller than the complete DNA molecule of a chromosome from that species.

A "nucleic acid molecule construct" is a nucleic acid molecule, either single- or double-stranded, that has been modified through human intervention to contain segments of nucleic acid combined and juxtaposed in an arrangement not existing in nature.

"Linear DNA" denotes non-circular DNA molecules having free 5' and 3' ends. Linear DNA can be prepared from closed circular DNA molecules, such as plasmids, by enzymatic digestion or physical disruption.

"Complementary DNA (cDNA)" is a single-stranded DNA molecule that is formed from an mRNA template by the enzyme reverse transcriptase. Typically, a primer complementary to portions of mRNA is employed for the initiation of reverse transcription. Those skilled in the art also use the term "cDNA" to refer to a double-stranded DNA molecule consisting of such a single-stranded DNA molecule and its complementary DNA strand. The term "cDNA" also refers to a clone of a cDNA molecule synthesized from an RNA template.

A "promoter" is a nucleotide sequence that directs the transcription of a structural gene. Typically, a promoter is located in the 5' non-coding region of a gene, proximal to the transcriptional start site of a structural gene. Sequence elements within promoters that function in the initiation of transcription are often characterized by consensus nucleotide sequences. These promoter elements include RNA polymerase binding sites, TATA sequences, CAAT sequences, differentiation-specific elements (DSEs; McGehee et al., *Mol. Endocrinol.* 7:551 (1993)), cyclic AMP response elements (CREs), serum response elements (SREs; Treisman, *Seminars in Cancer Biol.* 1:47 (1990)), glucocorticoid response elements (GREs), and binding sites for other transcription factors, such as CRE/ATF (O'Reilly et al., *J Biol. Chem.* 267:19938 (1992)), AP2 (Ye et al., *J Biol. Chem.* 269:25728 (1994)), SP1, cAMP response element binding protein (CREB; Loeken, *Gene Expr.* 3:253 (1993)) and octamer factors (see, in general, Watson et al., eds., *Molecular Biology of the Gene*, 4th ed. (The Benjamin/Cummings Publishing Company, Inc. 1987), and Lemaigre and Rousseau, *Biochem. J.* 303:1 (1994)). If a promoter is an inducible promoter, then the rate of transcription increases in response to an inducing agent. In contrast, the rate of transcription is not regulated by an inducing agent if the promoter is a constitutive promoter. Repressible promoters are also known.

A "core promoter" contains essential nucleotide sequences for promoter function, including the TATA box and start of transcription. By this definition, a core promoter may or may not have detectable activity in the absence of specific sequences that may enhance the activity or confer tissue specific activity.

A "regulatory element" is a nucleotide sequence that modulates the activity of a core promoter. For example, a regulatory element may contain a nucleotide sequence that binds with cellular factors enabling transcription exclusively or preferentially in particular cells, tissues, or organelles. These types of regulatory elements are normally associated with genes that are expressed in a "cell-specific," "tissue-specific," or "organelle-specific" manner. For example, the Zsig62 regulatory element preferentially induces gene expression in placental, spinal cord, pituitary, and prostate tissues, as opposed to adult brain, fetal brain, heart, kidney, liver, fetal lung, pancreas, and skeletal muscle tissues.

An "enhancer" is a type of regulatory element that can increase the efficiency of transcription, regardless of the distance or orientation of the enhancer relative to the start site of transcription.

"Heterologous DNA" refers to a DNA molecule, or a population of DNA molecules, that does not exist naturally within a given host cell. DNA molecules heterologous to a particular host cell may contain DNA derived from the host cell species (i.e., endogenous DNA) so long as that host DNA is combined with non-host DNA (i.e., exogenous DNA). For example, a DNA molecule containing a non-host DNA segment encoding a polypeptide operably linked to a host DNA segment comprising a transcription promoter is considered to be a heterologous DNA molecule. Conversely, a heterologous DNA molecule can comprise an endogenous gene operably linked with an exogenous promoter. As another illustration, a DNA molecule comprising a gene derived from a wild-type cell is considered to be heterologous DNA if that DNA molecule is introduced into a mutant cell that lacks the wild-type gene.

A "polypeptide" is a polymer of amino acid residues joined by peptide bonds, whether produced naturally or synthetically. Polypeptides of less than about 10 amino acid residues are commonly referred to as "peptides."

A "protein" is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless.

A peptide or polypeptide encoded by a non-host DNA molecule is a "heterologous" peptide or polypeptide.

An "integrated genetic element" is a segment of DNA that has been incorporated into a chromosome of a host cell after that element is introduced into the cell through human manipulation. Within the present invention, integrated genetic elements are most commonly derived from linearized plasmids that are introduced into the cells by electroporation or other techniques. Integrated genetic elements are passed from the original host cell to its progeny.

A "cloning vector" is a nucleic acid molecule, such as a plasmid, cosmid, or bacteriophage, that has the capability of replicating autonomously in a host cell. Cloning vectors typically contain one or a small number of restriction endonuclease recognition sites that allow insertion of a nucleic acid molecule in a determinable fashion without loss of an essential biological function of the vector, as well as nucleotide sequences encoding a marker gene that is suitable for use in the identification and selection of cells transformed with the cloning vector. Marker genes typically include genes that provide tetracycline resistance or ampicillin resistance.

An "expression vector" is a nucleic acid molecule encoding a gene that is expressed in a host cell. Typically, an expression vector comprises a transcription promoter, a gene, and a transcription terminator. Gene expression is usually placed under the control of a promoter, and such a gene is said to be "operably linked to" the promoter. Similarly, a regulatory element and a core promoter are operably linked if the regulatory element modulates the activity of the core promoter.

A "recombinant host" is a cell that contains a heterologous nucleic acid molecule, such as a cloning vector or expression vector. In the present context, an example of a recombinant host is a cell that produces Zsig62 from an expression vector. In contrast, Zsig62 can be produced by a cell that is a "natural source" of Zsig62, and that lacks an expression vector.

"Integrative transformants" are recombinant host cells, in which heterologous DNA has become integrated into the genomic DNA of the cells.

A "fusion protein" is a hybrid protein expressed by a nucleic acid molecule comprising nucleotide sequences of at least two genes. For example, a fusion protein can comprise at least part of a Zsig62 polypeptide fused with a polypeptide that binds an affinity matrix. Such a fusion protein provides a means to isolate large quantities of Zsig62 using affinity chromatography.

The term "receptor" denotes a cell-associated protein that binds to a bioactive molecule termed a "ligand." This interaction mediates the effect of the ligand on the cell. Receptors can be membrane bound, cytosolic or nuclear; monomeric (e.g., thyroid stimulating hormone receptor, beta-adrenergic receptor) or multimeric (e.g., PDGF receptor, growth hormone receptor, IL-3 receptor, GM-CSF receptor, G-CSF receptor, erythropoietin receptor and IL-6 receptor). Membrane-bound receptors are characterized by a multi-domain structure comprising an extracellular ligand-binding domain and an intracellular effector domain that is typically involved in signal transduction. In certain membrane-bound receptors, the extracellular ligand-binding domain and the intracellular effector domain are located in separate polypeptides that comprise the complete functional receptor.

In general, the binding of ligand to receptor results in a conformational change in the receptor that causes an interaction between the effector domain and other molecule(s) in the cell, which in turn leads to an alteration in the metabolism of the cell. Metabolic events that are often linked to receptor-ligand interactions include gene transcription, phosphorylation, dephosphorylation, increases in cyclic AMP production, mobilization of cellular calcium, mobilization of membrane lipids, cell adhesion, hydrolysis of inositol lipids and hydrolysis of phospholipids.

The term "secretory signal sequence" denotes a nucleotide sequence that encodes a peptide (a "secretory peptide") that, as a component of a larger polypeptide, directs the larger polypeptide through a secretory pathway of a cell in which it is synthesized. The larger polypeptide is commonly cleaved to remove the secretory peptide during transit through the secretory pathway.

An "isolated polypeptide" is a polypeptide that is essentially free from contaminating cellular components, such as carbohydrate, lipid, or other proteinaceous impurities associated with the polypeptide in nature. Typically, a preparation of isolated polypeptide contains the polypeptide in a highly purified form, i.e., at least about 80% pure, at least about 90% pure, at least about 95% pure, greater than 95% pure, or greater than 99% pure. One way to show that a particular protein preparation contains an isolated polypeptide is by the appearance of a single band following sodium dodecyl sulfate (SDS)-polyacrylamide gel electrophoresis of the protein preparation and Coomassie Brilliant Blue staining of the gel. However, the term "isolated" does not exclude the presence of the same polypeptide in alternative physical forms, such as dimers or alternatively glycosylated or derivatized forms.

The terms "amino-terminal" and "carboxyl-terminal" are used herein to denote positions within polypeptides. Where the context allows, these terms are used with reference to a particular sequence or portion of a polypeptide to denote proximity or relative position. For example, a certain sequence positioned carboxyl-terminal to a reference sequence within a polypeptide is located proximal to the carboxyl terminus of the reference sequence, but is not necessarily at the carboxyl terminus of the complete polypeptide.

The term "expression" refers to the biosynthesis of a gene product. For example, in the case of a structural gene, expression involves transcription of the structural gene into mRNA and the translation of mRNA into one or more polypeptides.

The term "splice variant" is used herein to denote alternative forms of RNA transcribed from a gene. Splice variation arises naturally through use of alternative splicing sites within a transcribed RNA molecule, or less commonly between separately transcribed RNA molecules, and may result in several mRNAs transcribed from the same gene. Splice variants may encode polypeptides having altered amino acid sequence. The term splice variant is also used herein to denote a polypeptide encoded by a splice variant of an mRNA transcribed from a gene.

As used herein, the term "immunomodulator" includes cytokines, stem cell growth factors, lymphotoxins, co-stimulatory molecules, hematopoietic factors, and synthetic analogs of these molecules.

The term "complement/anti-complement pair" denotes non-identical moieties that form a non-covalently associated, stable pair under appropriate conditions. For instance, biotin and avidin (or streptavidin) are prototypical members of a complement/anti-complement pair. Other exemplary complement/anti-complement pairs include receptor/ligand pairs, antibody/antigen (or hapten or epitope) pairs, sense/antisense polynucleotide pairs, and-the like. Where subsequent dissociation of the complement/anti-complement pair is desirable, the complement/anti-complement pair preferably has a binding affinity of less than $10^9$ $M^{-1}$.

An "anti-idiotype antibody" is an antibody that binds with the variable region domain of an immunoglobulin. In the present context, an anti-idiotype antibody binds with the variable region of an anti-Zsig62 antibody, and thus, an anti-idiotype antibody mimics an epitope of Zsig62.

An "antibody fragment" is a portion of an antibody such as $F(ab')_2$, $F(ab)_2$, Fab', Fab, and the like. Regardless of structure, an antibody fragment binds with the same antigen that is recognized by the intact antibody. For example, an anti-Zsig62 monoclonal antibody fragment binds with an epitope of Zsig62.

The term "antibody fragment" also includes a synthetic or a genetically engineered polypeptide that binds to a specific antigen, such as polypeptides consisting of the light chain variable region, "Fv" fragments consisting of the variable regions of the heavy and light chains, recombinant single chain polypeptide molecules in which light and heavy variable regions are connected by a peptide linker ("scFv proteins"), and minimal recognition units consisting of the amino acid residues that mimic the hypervariable region.

A "chimeric antibody" is a recombinant protein that contains the variable domains and complementary determining regions derived from a rodent antibody, while the remainder of the antibody molecule is derived from a human antibody.

"Humanized antibodies" are recombinant proteins in which murine complementarity determining regions of a monoclonal antibody have been transferred from heavy and light variable chains of the murine immunoglobulin into a human variable domain.

As used herein, a "therapeutic agent" is a molecule or atom which is conjugated to an antibody moiety to produce a conjugate which is useful for therapy. Examples of therapeutic agents include drugs, toxins, immunomodulators, chelators, boron compounds, photoactive agents or dyes, and radioisotopes.

A "detectable label" is a molecule or atom which can be conjugated to an antibody moiety to produce a molecule useful for diagnosis. Examples of detectable labels include chelators, photoactive agents, radioisotopes, fluorescent agents, paramagnetic ions, or other marker moieties.

A "tumor associated antigen" is a protein normally not expressed, or expressed at lower levels, by a normal counterpart cell. Examples of tumor associated antigens include alpha-fetoprotein, carcinoembryonic antigen, and Her-2/neu. Many other illustrations of tumor associated antigens are known to those of skill in the art. See, for example, Urban et al., *Ann. Rev. Immunol.* 10:617 (1992).

The term "affinity tag" is used herein to denote a polypeptide segment that can be attached to a second polypeptide to provide for purification or detection of the second polypeptide or provide sites for attachment of the second polypeptide to a substrate. In principal, any peptide or protein for which an antibody or other specific binding agent is available can be used as an affinity tag. Affinity tags include a poly-histidine tract, protein A (Nilsson et al., *EMBO J.* 4:1075 (1985); Nilsson et al., *Methods Enzymol.* 198:3 (1991)), glutathione S transferase (Smith and Johnson, *Gene* 67:31 (1988)), Glu-Glu affinity tag (Grussenmeyer et al., *Proc. Natl. Acad. Sci. USA* 82:7952 (1985)), substance P, FLAG peptide (Hopp et al., *Biotechnology* 6:1204 (1988)), streptavidin binding peptide, or other antigenic epitope or binding domain. See, in general, Ford et al., *Protein Expression and Purification* 2:95 (1991). Nucleic acid molecules encoding affinity tags are available from commercial suppliers (e.g., Pharmacia Biotech, Piscataway, N.J.).

A "naked antibody" is an entire antibody, as opposed to an antibody fragment, which is not conjugated with a therapeutic agent. Naked antibodies include both polyclonal and monoclonal antibodies, as well as certain recombinant antibodies, such as chimeric and humanized antibodies.

As used herein, the term "antibody component" includes both an entire antibody and an antibody fragment.

An "immunoconjugate" is a conjugate of an antibody component with a therapeutic agent or a detectable label.

As used herein, the term "antibody fusion protein" refers to a recombinant molecule that comprises an antibody component and a therapeutic agent. Examples of therapeutic agents suitable for such fusion proteins include immunomodulators ("antibody-immunomodulator fusion protein") and toxins ("antibody-toxin fusion protein").

A "target polypeptide" or a "target peptide" is an amino acid sequence that comprises at least one epitope, and that is expressed on a target cell, such as a tumor cell, or a cell that carries an infectious agent antigen. T cells recognize peptide epitopes presented by a major histocompatibility complex molecule to a target polypeptide or target peptide and typically lyse the target cell or recruit other immune cells to the site of the target cell, thereby killing the target cell.

An "antigenic peptide" is a peptide which will bind a major histocompatibility complex molecule to form an MHC-peptide complex which is recognized by a T cell, thereby inducing a cytotoxic lymphocyte response upon presentation to the T cell. Thus, antigenic peptides are capable of binding to an appropriate major histocompatibility complex molecule and inducing a cytotoxic T cells response, such as cell lysis or specific cytokine release against the target cell which binds or expresses the antigen. The antigenic peptide can be bound in the context of a class I or class II major histocompatibility complex molecule, on an antigen presenting cell or on a target cell.

In eukaryotes, RNA polymerase II catalyzes the transcription of a structural gene to produce mRNA. A nucleic acid molecule can be designed to contain an RNA polymerase II template in which the RNA transcript has a sequence that is complementary to that of a specific mRNA. The RNA transcript is termed an "anti-sense RNA" and a nucleic acid molecule that encodes the anti-sense RNA is termed an "anti-sense gene." Anti-sense RNA molecules are capable of binding to mRNA molecules, resulting in an inhibition of mRNA translation.

An "anti-sense oligonucleotide specific for Zsig62" or an "Zsig62 anti-sense oligonucleotide" is an oligonucleotide having a sequence (a) capable of forming a stable triplex with a portion of the Zsig62 gene, or (b) capable of forming a stable duplex with a portion of an mRNA transcript of the Zsig62 gene.

A "ribozyme" is a nucleic acid molecule that contains a catalytic center. The term includes RNA enzymes, self-splicing RNAs, self-cleaving RNAs, and nucleic acid molecules that perform these catalytic functions. A nucleic acid molecule that encodes a ribozyme is termed a "ribozyme gene."

An "external guide sequence" is a nucleic acid molecule that directs the endogenous ribozyme, RNase P, to a particular species of intracellular mRNA, resulting in the cleavage of the mRNA by RNase P. A nucleic acid molecule that encodes an external guide sequence is termed an "external guide sequence gene."

The term "variant Zsig62 gene" refers to nucleic acid molecules that encode a polypeptide having an amino acid sequence that is a modification of SEQ ID NO:2. Such variants include naturally-occurring polymorphisms of Zsig62 genes, as well as synthetic genes that contain conservative amino acid substitutions of the amino acid sequence of SEQ ID NO:2. Additional variant forms of Zsig62 genes are nucleic acid molecules that contain insertions or deletions of the nucleotide sequences described herein. A variant Zsig62 gene can be identified by determining whether the gene hybridizes with a nucleic acid molecule having the nucleotide sequence of SEQ ID NO:1, or its complement, under stringent conditions.

Alternatively, variant Zsig62 genes can be identified by sequence comparison. Two amino acid sequences have "100% amino acid sequence identity" if the amino acid residues of the two amino acid sequences are the same when aligned for maximal correspondence. Similarly, two nucleotide sequences have "100% nucleotide sequence identity" if the nucleotide residues of the two nucleotide sequences are the same when aligned for maximal correspondence. Sequence comparisons can be performed using standard software programs such as those included in the LASERGENE bioinformatics computing suite, which is produced by DNASTAR (Madison, Wis.). Other methods for comparing two nucleotide or amino acid sequences by determining optimal alignment are well-known to those of skill in the art (see, for example, Peruski and Peruski, *The Internet and the New Biology: Tools for Genomic and Molecular Research* (ASM Press, Inc. 1997), Wu et al. (eds.), "Information Superhighway and Computer Databases of Nucleic Acids and Proteins," in *Methods in Gene Biotechnology*, pages 123–151 (CRC Press, Inc. 1997), and Bishop (ed.), *Guide to Human Genome Computing*, 2nd Edition (Academic Press, Inc. 1998)). Particular methods for determining sequence identity are described below.

Regardless of the particular method used to identify a variant Zsig62 gene or variant Zsig62 polypeptide, a variant gene or polypeptide encoded by a variant gene may be characterized the ability to bind specifically to an anti-Zsig62 antibody.

The term "allelic variant" is used herein to denote any of two or more alternative forms of a gene occupying the same chromosomal locus. Allelic variation arises naturally through mutation, and may result in phenotypic polymorphism within populations. Gene mutations can be silent (no change in the encoded polypeptide) or may encode polypeptides having altered amino acid sequence. The term allelic variant is also used herein to denote a protein encoded by an allelic variant of a gene.

The term "ortholog" denotes a polypeptide or protein obtained from one species that is the functional counterpart of a polypeptide or protein from a different species. Sequence differences among orthologs are the result of speciation.

"Paralogs" are distinct but structurally related proteins made by an organism. Paralogs are believed to arise through gene duplication. For example, α-globin, β-globin, and myoglobin are paralogs of each other.

The present invention includes functional fragments of Zsig62 genes. Within the context of this invention, a "functional fragment" of a Zsig62 gene refers to a nucleic acid molecule that encodes a portion of a Zsig62 polypeptide which specifically binds with an anti-Zsig62 antibody, or to a nucleic acid molecule that can be used to distinguish between tumor and non-tumor tissue.

Due to the imprecision of standard analytical methods, molecular weights and lengths of polymers are understood to be approximate values. When such a value is expressed as "about" X or "approximately" X, the stated value of X will be understood to be accurate to ±10%.

3. Production of the Human Zsig62Gene

Nucleic acid molecules encoding a human Zsig62 gene can be obtained by screening a human cDNA or genomic library using polynucleotide probes based upon SEQ ID NO:1. These techniques are standard and well-established.

As an illustration, a nucleic acid molecule that encodes a human Zsig62 gene can be isolated from a human cDNA library. In this case, the first step would be to prepare the cDNA library by isolating RNA from pancreatic islet cells, placenta, spinal cord, pituitary, or prostate, using methods well-known to those of skill in the art. In general, RNA isolation techniques must provide a method for breaking cells, a means of inhibiting RNase-directed degradation of RNA, and a method of separating RNA from DNA, protein, and polysaccharide contaminants. For example, total RNA can be isolated by freezing tissue in liquid nitrogen, grinding the frozen tissue with a mortar and pestle to lyse the cells, extracting the ground tissue with a solution of phenol/chloroform to remove proteins, and separating RNA from the remaining impurities by selective precipitation with lithium chloride (see, for example, Ausubel et al. (eds.), *Short Protocols in Molecular Biology*, 3$^{rd}$ Edition, pages 4-1 to 4-6 (John Wiley & Sons 1995) ["Ausubel (1995)"]; Wu et al., *Methods in Gene Biotechnology*, pages 33–41 (CRC Press, Inc. 1997) ["Wu (1997)"]).

Alternatively, total RNA can be isolated from placental tissue (or, pancreatic islet cells, spinal cord, pituitary, and prostate) by extracting ground tissue with guanidinium isothiocyanate, extracting with organic solvents, and separating RNA from contaminants using differential centrifugation (see, for example, Chirgwin et al., *Biochemistry* 18:52 (1979); Ausubel (1995) at pages 4-1 to 4-6; Wu (1997) at pages 33–41).

In order to construct a cDNA library, poly(A)$^+$ RNA must be isolated from a total RNA preparation. Poly(A)$^+$ RNA can be isolated from total RNA using the standard technique of oligo(dT)-cellulose chromatography (see, for example, Aviv and Leder, *Proc. Nat'l Acad. Sci. USA* 69:1408 (1972); Ausubel (1995) at pages 4-11 to 4-12).

Double-stranded cDNA molecules are synthesized from poly(A)$^+$ RNA using techniques well-known to those in the art. (see, for example, Wu (1997) at pages 41–46). Moreover, commercially available kits can be used to synthesize double-stranded cDNA molecules. For example, such kits are available from Life Technologies, Inc. (Gaithersburg, Md.), CLONTECH Laboratories, Inc. (Palo Alto, Calif.), Promega Corporation (Madison, Wis.) and STRATAGENE (La Jolla, Calif.).

Various cloning vectors are appropriate for the construction of a cDNA library. For example, a cDNA library can be prepared in a vector derived from bacteriophage, such as a λgt10 vector. See, for example, Huynh et al., "Constructing and Screening cDNA Libraries in λgt10 and λgt11," in *DNA Cloning: A Practical Approach Vol. I,* Glover (ed.), page 49 (IRL Press, 1985); Wu (1997) at pages 47–52.

Alternatively, double-stranded cDNA molecules can be inserted into a plasmid vector, such as a PBLUESCRIPT vector (STRATAGENE; La Jolla, Calif.), a LAMDAGEM-4 (Promega Corp.) or other commercially available vectors. Suitable cloning vectors also can be obtained from the American Type Culture Collection (Manassas, Va.).

To amplify the cloned cDNA molecules, the cDNA library is inserted into a prokaryotic host, using standard techniques. For example, a cDNA library can be introduced into competent *E. coli* DH5 cells, which can be obtained, for example, from Life Technologies, Inc. (Gaithersburg, Md.).

A human genomic library can be prepared by means well-known in the art (see, for example, Ausubel (1995) at pages 5-1 to 5-6; Wu (1997) at pages 307–327). Genomic DNA can be isolated by lysing tissue with the detergent Sarkosyl, digesting the lysate with proteinase K, clearing insoluble debris from the lysate by centrifugation, precipitating nucleic acid from the lysate using isopropanol, and purifying resuspended DNA on a cesium chloride density gradient.

DNA fragments that are suitable for the production of a genomic library can be obtained by the random shearing of genomic DNA or by the partial digestion of genomic DNA with restriction endonucleases. Genomic DNA fragments can be inserted into a vector, such as a bacteriophage or cosmid vector, in accordance with conventional techniques, such as the use of restriction enzyme digestion to provide appropriate termini, the use of alkaline phosphatase treatment to avoid undesirable joining of DNA molecules, and ligation with appropriate ligases. Techniques for such manipulation are well-known in the art (see, for example, Ausubel (1995) at pages 5-1 to 5-6; Wu (1997) at pages 307–327).

Nucleic acid molecules that encode a human Zsig62 gene can also be obtained using the polymerase chain reaction (PCR) with oligonucleotide primers having nucleotide sequences that are based upon the nucleotide sequences of the human Zsig62 gene, as described herein. General methods for screening libraries with PCR are provided by, for example, Yu et al., "Use of the Polymerase Chain Reaction to Screen Phage Libraries," in *Methods in Molecular Biology, Vol.* 15: *PCR Protocols: Current Methods and Applications,* White (ed.), pages 211–215 (Humana Press, Inc. 1993). Moreover, techniques for using PCR to isolate related genes are described by, for example, Preston, "Use of Degenerate Oligonucleotide Primers and the Polymerase Chain Reaction to Clone Gene Family Members," in *Methods in Molecular Biology, Vol.* 15: *PCR Protocols: Current Methods and Applications,* White (ed.), pages 317–337 (Humana Press, Inc. 1993).

Alternatively, human genomic libraries can be obtained from commercial sources such as Research Genetics (Huntsville, Ala.) and the American Type Culture Collection (Manassas, Va.).

A library containing cDNA or genomic clones can be screened with one or more polynucleotide probes based upon SEQ ID NO:1, using standard methods (see, for example, Ausubel (1995) at pages 6-1 to 6-11).

Anti-Zsig62 antibodies, produced as described below, can also be used to isolate DNA sequences that encode human Zsig62 genes from cDNA libraries. For example, the antibodies can be used to screen λ.gt11 expression libraries, or the antibodies can be used for immunoscreening following hybrid selection and translation (see, for example, Ausubel (1995) at pages 6-12 to 6-16; Margolis et al., "Screening λ expression libraries with antibody and protein probes," in *DNA Cloning 2. Expression Systems, 2nd Edition,* Glover et al. (eds.), pages 1–14 (Oxford University Press 1995)).

As an alternative, a Zsig62 gene can be obtained by synthesizing nucleic acid molecules using mutually priming long oligonucleotides and the nucleotide sequences described herein (see, for example, Ausubel (1995) at pages 8-8 to 8-9). Established techniques using the polymerase chain reaction provide the ability to synthesize DNA molecules at least two kilobases in length (Adang et al., *Plant Molec. Biol.* 21:1131 (1993), Bambot et al., *PCR Methods and Applications* 2:266 (1993), Dillon et al., "Use of the Polymerase Chain Reaction for the Rapid Construction of Synthetic Genes," in *Methods in Molecular Biology, Vol.* 15: *PCR Protocols: Current Methods and Applications,* White (ed.), pages 263–268, (Humana Press, Inc. 1993), and Holowachuk et al., *PCR Methods Appl.* 4:299 (1995)).

The nucleic acid molecules of the present invention can also be synthesized with "gene machines" using protocols such as the phosphoramidite method. If chemically-synthesized double stranded DNA is required for an application such as the synthesis of a gene or a gene fragment, then each complementary strand is made separately. The production of short genes (60 to 80 base pairs) is technically straightforward and can be accomplished by synthesizing the complementary strands and then annealing them. For the production of longer genes (>300 base pairs), however, special strategies may be required, because the coupling efficiency of each cycle during chemical DNA synthesis is seldom 100%. To overcome this problem, synthetic genes (double-stranded) are assembled in modular form from single-stranded fragments that are from 20 to 100 nucleotides in length. For reviews on polynucleotide synthesis, see, for example, Glick and Pasternak, *Molecular Biotechnology, Principles and Applications of Recombinant DNA* (ASM Press 1994), Itakura et al., *Annu. Rev. Biochem.* 53:323 (1984), and Climie et al., *Proc. Nat'l Acad. Sci. USA* 87:633 (1990).

The sequence of a Zsig62 cDNA or Zsig62 genomic fragment can be determined using standard methods. Zsig62 polynucleotide sequences disclosed herein can also be used as probes or primers to clone 5' non-coding regions of a Zsig62 gene. Promoter elements from a Zsig62 gene can be used to direct the expression of heterologous genes in, for example, pituitary tissue of transgenic animals or patients undergoing gene therapy. The identification of genomic fragments containing a Zsig62 promoter or regulatory element can be achieved using well-established techniques, such as deletion analysis (see, generally, Ausubel (1995)).

Cloning of 5' flanking sequences also facilitates production of Zsig62 proteins by "gene activation," according to the general methods disclosed in U.S. Pat. No. 5,641,670. Briefly, expression of an endogenous Zsig62 gene in a cell is altered by introducing into the Zsig62 locus a DNA construct comprising at least a targeting sequence, a regulatory sequence, an exon, and an unpaired splice donor site. The targeting sequence is a Zsig62 5' non-coding sequence that permits homologous recombination of the construct with the endogenous Zsig62 locus, whereby the sequences within the construct become operably linked with the endogenous Zsig62 coding sequence. In this way, an endogenous Zsig62 promoter can be replaced or supplemented with other regulatory sequences to provide enhanced, tissue-specific, or otherwise regulated expression.

4. Production of Zsig62 Gene Variants

The present invention provides a variety of nucleic acid molecules, including DNA and RNA molecules, that encode the Zsig62 polypeptides disclosed herein. Those skilled in the art will readily recognize that, in view of the degeneracy of the genetic code, considerable sequence variation is possible among these polynucleotide molecules. SEQ ID NO:3 is a degenerate nucleotide sequence that encompasses all nucleic acid molecules that encode the Zsig62 polypeptides of SEQ ID NO:2. Those skilled in the art will recognize that the degenerate sequence of SEQ ID NO:3 also provides all RNA sequences encoding SEQ ID NO:2, by substituting U for T. Thus, the present invention contemplates Zsig62 polypeptide-encoding nucleic acid molecules comprising nucleotide 20 to nucleotide 316 of SEQ ID NO:1, and their RNA equivalents.

Table 1 sets forth the one-letter codes used within SEQ ID NO:3 to denote degenerate nucleotide positions. "Resolutions" are the nucleotides denoted by a code letter. "Complement" indicates the code for the complementary nucleotide (s). For example, the code Y denotes either C or T, and its complement R denotes A or G, A being complementary to T, and G being complementary to C.

TABLE 1

| Nucleotide | Resolution | Complement | Resolution |
|---|---|---|---|
| A | A | T | T |
| C | C | G | G |
| G | G | C | C |
| T | T | A | A |
| R | A\|G | Y | C\|T |
| Y | C\|T | R | A\|G |
| M | A\|C | K | G\|T |
| K | G\|T | M | A\|C |
| S | C\|G | S | C\|G |
| W | A\|T | W | A\|T |
| H | A\|C\|T | D | A\|G\|T |
| B | C\|G\|T | V | A\|C\|G |
| V | A\|C\|G | B | C\|G\|T |
| D | A\|G\|T | H | A\|C\|T |
| N | A\|C\|G\|T | N | A\|C\|G\|T |

The degenerate codons used in SEQ ID NO:3, encompassing all possible codons for a given amino acid, are set forth in Table 2.

TABLE 2

| Amino Acid | One Letter Code | Codons | Degenerate Codon |
|---|---|---|---|
| Cys | C | TGC TGT | TGY |
| Ser | S | AGC AGT TCA TCC TCG TCT | WSN |
| Thr | T | ACA ACC ACG ACT | ACN |
| Pro | P | CCA CCC CCG CCT | CCN |
| Ala | A | GCA GCC GCG GCT | GCN |
| Gly | G | GGA GGC GGG GGT | GGN |
| Asn | N | AAC AAT | AAY |
| Asp | D | GAC GAT | GAY |
| Glu | E | GAA GAG | GAR |
| Gln | Q | CAA CAG | CAR |
| His | H | CAC CAT | CAY |
| Arg | R | AGA AGG CGA CGC CGG CGT | MGN |
| Lys | K | AAA AAG | AAR |
| Met | M | ATG | ATG |
| Ile | I | ATA ATC ATT | ATH |
| Leu | L | CTA CTC CTG CTT TTA TTG | YTN |
| Val | V | GTA GTC GTG GTT | GTN |

TABLE 2-continued

| Amino Acid | One Letter Code | Codons | Degenerate Codon |
|---|---|---|---|
| Phe | F | TTC TTT | TTY |
| Tyr | Y | TAC TAT | TAY |
| Trp | W | TGG | TGG |
| Ter | . | TAA TAG TGA | TRR |
| Asn\|Asp | B | | RAY |
| Glu\|Gln | Z | | SAR |
| Any | X | | NNN |

One of ordinary skill in the art will appreciate that some ambiguity is introduced in determining a degenerate codon, representative of all possible codons encoding an amino acid. For example, the degenerate codon for serine (WSN) can, in some circumstances, encode arginine (AGR), and the degenerate codon for arginine (MGN) can, in some circumstances, encode serine (AGY). A similar relationship exists between codons encoding phenylalanine and leucine. Thus, some polynucleotides encompassed by the degenerate sequence may encode variant amino acid sequences, but one of ordinary skill in the art can easily identify such variant sequences by reference to the amino acid sequence of SEQ ID NO:2. Variant sequences can be readily tested for functionality as described herein.

Different species can exhibit "preferential codon usage." In general, see, Grantham et al., *Nucleic Acids Res.* 8:1893 (1980), Haas et al. *Curr. Biol.* 6:315 (1996), Wain-Hobson et al, *Gene* 13:355 (1981), Grosjean and Fiers, *Gene* 18:199 (1982), Holm, *Nuc. Acids Res.* 14:3075 (1986), Ikemura, *J. Mol. Biol.* 158:573 (1982), Sharp and Matassi, *Curr. Opin. Genet. Dev.* 4:851 (1994), Kane, *Curr. Opin. Biotechnol.* 6:494 (1995), and Makrides, *Microbiol. Rev.* 60:512 (1996). As used herein, the term "preferential codon usage" or "preferential codons" is a term of art referring to protein translation codons that are most frequently used in cells of a certain species, thus favoring one or a few representatives of the possible codons encoding each amino acid (See Table 2). For example, the amino acid threonine (Thr) may be encoded by ACA, ACC, ACG, or ACT, but in mammalian cells ACC is the most commonly used codon; in other species, for example, insect cells, yeast, viruses or bacteria, different Thr codons may be preferential. Preferential codons for a particular species can be introduced into the polynucleotides of the present invention by a variety of methods known in the art. Introduction of preferential codon sequences into recombinant DNA can, for example, enhance production of the protein by making protein translation more efficient within a particular cell type or species. Therefore, the degenerate codon sequence disclosed in SEQ ID NO:3 serves as a template for optimizing expression of polynucleotides in various cell types and species commonly used in the art and disclosed herein. Sequences containing preferential codons can be tested and optimized for expression in various species, and tested for functionality as disclosed herein.

The present invention further provides variant polypeptides and nucleic acid molecules that represent counterparts from other species (orthologs). These species include, but are not limited to mammalian, avian, amphibian, reptile, fish, insect and other vertebrate and invertebrate species. Of particular interest are Zsig62 polypeptides from other mammalian species, including murine, porcine, ovine, bovine, canine, feline, equine, and other primate polypeptides. Orthologs of human Zsig62 can be cloned using information and compositions provided by the present invention in combination with conventional cloning techniques. For example, a cDNA can be cloned using mRNA obtained from a tissue or cell type that expresses Zsig62 as disclosed herein. Suitable sources of mRNA can be identified by probing northern blots with probes designed from the sequences disclosed herein. A library is then prepared from mRNA of a positive tissue or cell line.

A Zsig62-encoding cDNA can then be isolated by a variety of methods, such as by probing with a complete or partial human cDNA or with one or more sets of degenerate probes based on the disclosed sequences. A cDNA can also be cloned using the polymerase chain reaction with primers designed from the representative human Zsig62 sequences disclosed herein. Within an additional method, the cDNA library can be used to transform or transfect host cells, and expression of the cDNA of interest can be detected with an antibody to Zsig62 polypeptide. Similar techniques can also be applied to the isolation of genomic clones.

Those skilled in the art will recognize that the sequence disclosed in SEQ ID NO:1 represents a single allele of human Zsig62, and that allelic variation and alternative splicing are expected to occur. Allelic variants of this sequence can be cloned by probing cDNA or genomic libraries from different individuals according to standard procedures. Allelic variants of the nucleotide sequence shown in SEQ ID NO:1, including those containing silent mutations and those in which mutations result in amino acid sequence changes, are within the scope of the present invention, as are proteins which are allelic variants of SEQ ID NO:2. cDNA molecules generated from alternatively spliced mRNAs, which retain the properties of the Zsig62 polypeptide are included within the scope of the present invention, as are polypeptides encoded by such cDNAs and mRNAs. Allelic variants and splice variants of these sequences can be cloned by probing cDNA or genomic libraries from different individuals or tissues according to standard procedures known in the art.

Within certain embodiments of the invention, the isolated nucleic acid molecules can hybridize under stringent conditions to nucleic acid molecules comprising nucleotide sequences disclosed herein. For example, such nucleic acid molecules can hybridize under stringent conditions to nucleic acid molecules comprising the nucleotide sequence of SEQ ID NO:1, to nucleic acid molecules having the nucleotide sequence of nucleotides 20 to 316 of SEQ ID NO: 1, or to nucleic acid molecules having a nucleotide sequence complementary to SEQ ID NO:1 or to nucleotides 20 to 316 of SEQ ID NO:1. In general, stringent conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe.

A pair of nucleic acid molecules, such as DNA-DNA, RNA-RNA and DNA-RNA, can hybridize if the nucleotide sequences have some degree of complementarity. Hybrids can tolerate mismatched base pairs in the double helix, but the stability of the hybrid is influenced by the degree of mismatch. The $T_m$ of the mismatched hybrid decreases by 1° C. for every 1–1.5% base pair mismatch. Varying the stringency of the hybridization conditions allows control over the degree of mismatch that will be present in the hybrid. The degree of stringency increases as the hybridization temperature increases and the ionic strength of the hybridization buffer decreases. Stringent hybridization conditions encompass temperatures of about 5–25° C. below the $T_m$ of the hybrid and a hybridization buffer having up to 1 M Na$^+$. Higher degrees of stringency at lower temperatures can be achieved with the addition of formamide which reduces the $T_m$ of the hybrid about 1° C. for each 1% formamide in the buffer solution. Generally, such stringent conditions include temperatures of 20–70° C. and a hybridization buffer containing up to 6×SSC and 0–50% formamide. A higher degree of stringency can be achieved at temperatures of from 40–70° C. with a hybridization buffer having up to 4×SSC and from 0–50% formamide. Highly stringent conditions typically encompass temperatures of 42–70° C. with a hybridization buffer having up to 1×SSC and 0–50% formamide. Different degrees of stringency can be used during hybridization and washing to achieve maximum specific binding to the target sequence. Typically, the washes following hybridization are performed at increasing degrees of stringency to remove non-hybridized polynucleotide probes from hybridized complexes.

The above conditions are meant to serve as a guide and it is well within the abilities of one skilled in the art to adapt these conditions for use with a particular polypeptide hybrid. The $T_m$ for a specific target sequence is the temperature (under defined conditions) at which 50% of the target sequence will hybridize to a perfectly matched probe sequence. Those conditions which influence the $T_m$ include, the size and base pair content of the polynucleotide probe, the ionic strength of the hybridization solution, and the presence of destabilizing agents in the hybridization solution. Numerous equations for calculating $T_m$ are known in the art, and are specific for DNA, RNA and DNA-RNA hybrids and polynucleotide probe sequences of varying length (see, for example, Sambrook et al., *Molecular Cloning: A Laboratory Manual,* Second Edition (Cold Spring Harbor Press 1989); Ausubel et al, (eds.), *Current Protocols in Molecular Biology* (John Wiley and Sons, Inc. 1987); Berger and Kimmel (eds.), *Guide to Molecular Cloning Techniques,* (Academic Press, Inc. 1987); and Wetmur, *Crit. Rev. Biochem. Mol. Biol.* 26:227 (1990)). Sequence analysis software such as OLIGO 6.0 (LSR; Long Lake, Minn.) and *Primer Premier* 4.0 (Premier Biosoft International; Palo Alto, Calif.), as well as sites on the Internet, are available tools for analyzing a given sequence and calculating $T_m$ based on user defined criteria. Such programs can also analyze a given sequence under defined conditions and identify suitable probe sequences. Typically, hybridization of longer polynucleotide sequences, >50 base pairs, is performed at temperatures of about 20–25° C. below the calculated $T_m$. For smaller probes, <50 base pairs, hybridization is typically carried out at the $T_m$ or 5–10° C. below. This allows for the maximum rate of hybridization for DNA-DNA and DNA-RNA hybrids.

The length of the polynucleotide sequence influences the rate and stability of hybrid formation. Smaller probe sequences, <50 base pairs, reach equilibrium with complementary sequences rapidly, but may form less stable hybrids. Incubation times of anywhere from minutes to hours can be used to achieve hybrid formation. Longer probe sequences come to equilibrium more slowly, but form more stable complexes even at lower temperatures. Incubations are allowed to proceed overnight or longer. Generally, incubations are carried out for a period equal to three times the calculated Cot time. Cot time, the time it takes for the polynucleotide sequences to reassociate, can be calculated for a particular sequence by methods known in the art.

The base pair composition of polynucleotide sequence will effect the thermal stability of the hybrid complex, thereby influencing the choice of hybridization temperature and the ionic strength of the hybridization buffer. A-T pairs are less stable than G-C pairs in aqueous solutions containing sodium chloride. Therefore, the higher the G-C content, the more stable the hybrid. Even distribution of G and C residues within the sequence also contribute positively to hybrid stability. In addition, the base pair composition can be manipulated to alter the $T_m$ of a given sequence. For example, 5-methyldeoxycytidine can be substituted for deoxycytidine and 5-bromodeoxyuridine can be substituted for thymidine to increase the $T_m$, whereas 7-deazz-2'-deoxyguanosine can be substituted for guanosine to reduce dependence on $T_m$.

The ionic concentration of the hybridization buffer also affects the stability of the hybrid. Hybridization buffers generally contain blocking agents such as Denhardt's solution (Sigma Chemical Co., St. Louis, Mo.), denatured salmon sperm DNA, tRNA, milk powders (BLOTTO), heparin or SDS, and a Na$^+$ source, such as SSC (1×SSC: 0.15 M sodium chloride, 15 mM sodium citrate) or SSPE (1×SSPE: 1.8 M NaCl, 10 mM NaH$_2$PO$_4$, 1 mM EDTA, pH 7.7). By decreasing the ionic concentration of the buffer, the stability of the hybrid is increased. Typically, hybridization buffers contain from between 10 mM–1 M Na$^+$. The addition of destabilizing or denaturing agents such as formamide, tetralkylammonium salts, guanidinium cations or thiocyanate cations to the hybridization solution will alter the $T_m$ of a hybrid. Typically, formamide is used at a concentration of up to 50% to allow incubations to be carried out at more convenient and lower temperatures. Formamide also acts to reduce non-specific background when using RNA probes.

As an illustration, a nucleic acid molecule encoding a variant Zsig62 polypeptide can be hybridized with a nucleic acid molecule having the nucleotide sequence of SEQ ID NO:1 (or its complement) at 42° C. overnight in a solution comprising 50% formamide, 5×SSC (1×SSC: 0.15 M sodium chloride and 15 mM sodium citrate), 50 mM sodium phosphate (pH 7.6), 5×Denhardt's solution (100×Denhardt's solution: 2%. (w/v) Ficoll 400, 2% (w/v) polyvinylpyrrolidone, and 2% (w/v) bovine serum albumin), 10% dextran sulfate, and 20 μg/ml denatured, sheared salmon sperm DNA. One of skill in the art can devise variations of these hybridization conditions. For example, the hybridization mixture can be incubated at a higher temperature, such as about 65° C., in a solution that does not contain formamide. Moreover, premixed hybridization solutions are available (e.g., EXPRESSHYB Hybridization Solution from CLONTECH Laboratories, Inc.), and hybridization can be performed according to the manufacturer's instructions.

Following hybridization, the nucleic acid molecules can be washed to remove non-hybridized nucleic acid molecules under stringent conditions, or under highly stringent conditions. Typical stringent washing conditions include washing in a solution of 0.5×–2×SSC with 0.1% sodium dodecyl sulfate (SDS) at 55–65° C. That is, nucleic acid molecules encoding a variant Zsig62 polypeptide remain hybridized, following stringent washing conditions, with a nucleic acid molecule having the nucleotide sequence of SEQ ID NO:1 (or its complement), in which the wash stringency is equivalent to 0.5×–2×SSC with 0.1% SDS at 55–65° C., including 0.5×SSC with 0.1% SDS at 55° C., or 2×SSC with 0.1% SDS at 65° C. One of skill in the art can readily devise equivalent conditions, for example, by substituting SSPE for SSC in the wash solution.

Typical highly stringent washing conditions include washing in a solution of 0.1×–0.2×SSC with 0.1% sodium dodecyl sulfate (SDS) at 50–65° C. In other words, nucleic acid molecules encoding a variant Zsig62 polypeptide remain hybridized, following highly stringent washing conditions, with a nucleic acid molecule having the nucleotide sequence of SEQ ID NO:1 (or its complement), in which the wash stringency is equivalent to 0.1×–0.2×SSC with 0.1% SDS at 50–65° C., including 0.1×SSC with 0.1% SDS at 50° C., or 0.2×SSC with 0.1% SDS at 65° C.

and the "BLOSUM62" scoring matrix of Henikoff and Henikoff (ibid.) as shown in Table 3 (amino acids are indicated by the standard one-letter codes). The percent identity is then calculated as: ([Total number of identical matches]/[length of the longer sequence plus the number of gaps introduced into the longer sequence in order to align the two sequences])(100).

TABLE 3

|   | A  | R  | N  | D  | C  | Q  | E  | G  | H  | I  | L  | K  | M  | F  | P  | S  | T  | W  | Y  | V |
|---|----|----|----|----|----|----|----|----|----|----|----|----|----|----|----|----|----|----|----|---|
| A | 4  |    |    |    |    |    |    |    |    |    |    |    |    |    |    |    |    |    |    |   |
| R | -1 | 5  |    |    |    |    |    |    |    |    |    |    |    |    |    |    |    |    |    |   |
| N | -2 | 0  | 6  |    |    |    |    |    |    |    |    |    |    |    |    |    |    |    |    |   |
| D | -2 | -2 | 1  | 6  |    |    |    |    |    |    |    |    |    |    |    |    |    |    |    |   |
| C | 0  | -3 | -3 | -3 | 9  |    |    |    |    |    |    |    |    |    |    |    |    |    |    |   |
| Q | -1 | 1  | 0  | 0  | -3 | 5  |    |    |    |    |    |    |    |    |    |    |    |    |    |   |
| E | -1 | 0  | 0  | 2  | -4 | 2  | 5  |    |    |    |    |    |    |    |    |    |    |    |    |   |
| G | 0  | -2 | 0  | -1 | -3 | -2 | -2 | 6  |    |    |    |    |    |    |    |    |    |    |    |   |
| H | -2 | 0  | 1  | -1 | -3 | 0  | 0  | -2 | 8  |    |    |    |    |    |    |    |    |    |    |   |
| I | -1 | -3 | -3 | -3 | -1 | -3 | -3 | -4 | -3 | 4  |    |    |    |    |    |    |    |    |    |   |
| L | -1 | -2 | -3 | -4 | -1 | -2 | -3 | -4 | -3 | 2  | 4  |    |    |    |    |    |    |    |    |   |
| K | -1 | 2  | 0  | -1 | -3 | 1  | 1  | -2 | -1 | -3 | -2 | 5  |    |    |    |    |    |    |    |   |
| M | -1 | -1 | -2 | -3 | -1 | 0  | -2 | -3 | -2 | 1  | 2  | -1 | 5  |    |    |    |    |    |    |   |
| F | -2 | -3 | -3 | -3 | -2 | -3 | -3 | -3 | -1 | 0  | 0  | -3 | 0  | 6  |    |    |    |    |    |   |
| P | -1 | -2 | -2 | -1 | -3 | -1 | -1 | -2 | -2 | -3 | -3 | -1 | -2 | -4 | 7  |    |    |    |    |   |
| S | 1  | -1 | 1  | 0  | -1 | 0  | 0  | 0  | -1 | -2 | -2 | 0  | -1 | -2 | -1 | 4  |    |    |    |   |
| T | 0  | -1 | 0  | -1 | -1 | -1 | -1 | -2 | -2 | -1 | -1 | -1 | -1 | -2 | -1 | 1  | 5  |    |    |   |
| W | -3 | -3 | -4 | -4 | -2 | -2 | -3 | -2 | -2 | -3 | -2 | -3 | -1 | 1  | -4 | -3 | -2 | 11 |    |   |
| Y | -2 | -2 | -2 | -3 | -2 | -1 | -2 | -3 | 2  | -1 | -1 | -2 | -1 | 3  | -3 | -2 | -2 | 2  | 7  |   |
| V | 0  | -3 | -3 | -3 | -1 | -2 | -2 | -3 | -3 | 3  | 1  | -2 | 1  | -1 | -2 | -2 | 0  | -3 | -1 | 4 |

The present invention also provides isolated Zsig62 polypeptides that have a substantially similar sequence identity to the polypeptides of SEQ ID NO:2, or their orthologs. The term "substantially similar sequence identity" is used herein to denote polypeptides having 70%, 80%, 90%, 95% or greater than 95% sequence identity to the sequences shown in SEQ ID NO:2, or their orthologs.

The present invention also contemplates Zsig62 variant nucleic acid molecules that can be identified using two criteria: a determination of the similarity between the encoded polypeptide with the amino acid sequence of SEQ ID NO:2, and a hybridization assay, as described above. Such Zsig62 variants include nucleic acid molecules (1) that remain hybridized, following stringent washing conditions, with a nucleic acid molecule having the nucleotide sequence of SEQ ID NO:1 (or its complement), in which the wash stringency is equivalent to 0.5×–2×SSC with 0.1% SDS at 55–65° C., and (2) that encode a polypeptide having 70%, 80%, 90%, 95% or greater than 95% sequence identity to the amino acid sequence of SEQ ID NO:2. Alternatively, Zsig62 variants can be characterized as nucleic acid molecules (1) that remain hybridized, following highly stringent washing conditions, with a nucleic acid molecule having the nucleotide sequence of SEQ ID NO:1 (or its complement), in which the wash stringency is equivalent to 0.1×–0.2×SSC with 0.1% SDS at 50–65° C., and (2) that encode a polypeptide having 70%, 80%, 90%, 95% or greater than 95% sequence identity to the amino acid sequence of SEQ ID NO:2.

Percent sequence identity is determined by conventional methods. See, for example, Altschul et al., Bull. Math. Bio. 48:603 (1986), and Henikoff and Henikoff, Proc. Natl. Acad. Sci. USA 89:10915 (1992). Briefly, two amino acid sequences are aligned to optimize the alignment scores using a gap opening penalty of 10, a gap extension penalty of 1, Those skilled in the art appreciate that there are many established algorithms available to align two amino acid sequences. The "FASTA" similarity search algorithm of Pearson and Lipman is a suitable protein alignment method for examining the level of identity shared by an amino acid sequence disclosed herein and the amino acid sequence of a putative Zsig62 variant. The FASTA algorithm is described by Pearson and Lipman, Proc. Nat'l Acad. Sci. USA 85:2444 (1988), and by Pearson, Meth. Enzymol. 183:63 (1990). Briefly, FASTA first characterizes sequence similarity by identifying regions shared by the query sequence (e.g., SEQ ID NO:2) and a test sequence that have either the highest density of identities (if the ktup variable is 1) or pairs of identities (if ktup=2), without considering conservative amino acid substitutions, insertions, or deletions. The ten regions with the highest density of identities are then rescored by comparing the similarity of all paired amino acids using an amino acid substitution matrix, and the ends of the regions are "trimmed" to include only those residues that contribute to the highest score. If there are several regions with scores greater than the "cutoff" value (calculated by a predetermined formula based upon the length of the sequence and the ktup value), then the trimmed initial regions are examined to determine whether the regions can be joined to form an approximate alignment with gaps. Finally, the highest scoring regions of the two amino acid sequences are aligned using a modification of the Needleman-Wunsch-Sellers algorithm (Needleman and Wunsch, J. Mol. Biol. 48:444 (1970); Sellers, SIAM J. Appl. Math. 26:787 (1974)), which allows for amino acid insertions and deletions. Illustrative parameters for FASTA analysis are: ktup=1, gap opening penalty=10, gap extension penalty=1, and substitution matrix=BLOSUM62. These parameters can be introduced into a FASTA program by modifying the scoring matrix file ("SMATRIX"), as explained in Appendix 2 of Pearson, Meth. Enzymol. 183:63 (1990).

FASTA can also be used to determine the sequence identity of nucleic acid molecules using a ratio as disclosed above. For nucleotide sequence comparisons, the ktup value can range between one to six, preferably from three to six, most preferably three, with other parameters set as described above.

The present invention includes nucleic acid molecules that encode a polypeptide having a conservative amino acid change, compared with the amino acid sequence of SEQ ID NO:2. That is, variants can be obtained that contain one or more amino acid substitutions of SEQ ID NO:2, in which an alkyl amino acid is substituted for an alkyl amino acid in a Zsig62 amino acid sequence, an aromatic amino acid is substituted for an aromatic amino acid in a Zsig62 amino acid sequence, a sulfur-containing amino acid is substituted for a sulfur-containing amino acid in a Zsig62 amino acid sequence, a hydroxy-containing amino acid is substituted for a hydroxy-containing amino acid in a Zsig62 amino acid sequence, an acidic amino acid is substituted for an acidic amino acid in a Zsig62 amino acid sequence, a basic amino acid is substituted for a basic amino acid in a Zsig62 amino acid sequence, or a dibasic monocarboxylic amino acid is substituted for a dibasic monocarboxylic amino acid in a Zsig62 amino acid sequence.

Among the common amino acids, for example, a "conservative amino acid substitution" is illustrated by a substitution among amino acids within each of the following groups: (1) glycine, alanine, valine, leucine, and isoleucine, (2) phenylalanine, tyrosine, and tryptophan, (3) serine and threonine, (4) aspartate and glutamate, (5) glutamine and asparagine, and (6) lysine, arginine and histidine.

The BLOSUM62 table is an amino acid substitution matrix derived from about 2,000 local multiple alignments of protein sequence segments, representing highly conserved regions of more than 500 groups of related proteins (Henikoff and Henikoff, *Proc. Nat'l Acad. Sci. USA* 89:10915 (1992)). Accordingly, the BLOSUM62 substitution frequencies can be used to define conservative amino acid substitutions that may be introduced into the amino acid sequences of the present invention. Although it is possible to design amino acid substitutions based solely upon chemical properties (as discussed above), the language "conservative amino acid substitution" preferably refers to a substitution represented by a BLOSUM62 value of greater than –1. For example, an amino acid substitution is conservative if the substitution is characterized by a BLOSUM62 value of 0, 1, 2, or 3. According to this system, certain conservative amino acid substitutions are characterized by a BLOSUM62 value of at least 1 (e.g., 1, 2 or 3), while other conservative amino acid substitutions are characterized by a BLOSUM62 value of at least 2 (e.g., 2 or 3).

Particular variants of Zsig62 are characterized by having greater than 70%, at least 80%, at least 90%, or at least 95% sequence identity to the corresponding amino acid sequence (e.g., SEQ ID NO:2), wherein the variation in amino acid sequence is due to one or more conservative amino acid substitutions.

Conservative amino acid changes in a Zsig62 gene can be introduced by substituting nucleotides for the nucleotides recited in SEQ ID NO: 1. Such "conservative amino acid" variants can be obtained, for example, by oligonucleotide-directed mutagenesis, linker-scanning mutagenesis, mutagenesis using the polymerase chain reaction, and the like (see Ausubel (1995) at pages 8-10 to 8-22; and McPherson (ed.), *Directed Mutagenesis: A Practical Approach* (IRL Press 1991)). A variant Zsig62 polypeptide can be identified by the ability to specifically bind anti-Zsig62 antibodies.

The proteins of the present invention can also comprise non-naturally occurring amino acid residues. Non-naturally occurring amino acids include, without limitation, trans-3-methylproline, 2,4-methanoproline, cis-4-hydroxyproline, trans-4-hydroxyproline, N-methylglycine, allo-threonine, methylthreonine, hydroxyethylcysteine, hydroxyethylhomocysteine, nitroglutamine, homoglutamine, pipecolic acid, thiazolidine carboxylic acid, dehydroproline, 3- and 4-methylproline, 3,3-dimethylproline, tert-leucine, norvaline, 2-azaphenylalanine, 3-azaphenylalanine, 4-azaphenylalanine, and 4-fluorophenylalanine. Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations is typically carried out in a cell-free system comprising an *E. coli* S30 extract and commercially available enzymes and other reagents. Proteins are purified by chromatography. See, for example, Robertson et al., *J. Am. Chem. Soc.* 113:2722 (1991), Ellman et al., *Methods Enzymol.* 202:301 (1991), Chung et al., *Science* 259:806 (1993), and Chung et al., *Proc. Nat'l Acad. Sci. USA* 90:10145 (1993).

In a second method, translation is carried out in Xenopus oocytes by microinjection of mutated mRNA and chemically aminoacylated suppressor tRNAs (Turcatti et al., *J. Biol. Chem.* 271:19991 (1996)). Within a third method, *E. coli* cells are cultured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the protein in place of its natural counterpart. See, Koide et al., *Biochem.* 33:7470 (1994). Naturally occurring amino acid residues can be converted to non-naturally occurring species by in vitro chemical modification. Chemical modification can be combined with site-directed mutagenesis to further expand the range of substitutions (Wynn and Richards, *Protein Sci.* 2.395 (1993)).

A limited number of non-conservative amino acids, amino acids that are not encoded by the genetic code, non-naturally occurring amino acids, and unnatural amino acids may be substituted for Zsig62 amino acid residues.

Essential amino acids in the polypeptides of the present invention can be identified according to procedures known in the art, such as site-directed mutagenesis or alanine-scanning mutagenesis (Cunningham and Wells, *Science* 244:1081 (1989), Bass et al., *Proc. Nat'l Acad Sci. USA* 88:4498 (1991), Coombs and Corey, "Site-Directed Directed Mutagenesis and Protein Engineering," in Proteins: *Analysis and Design,* Angeletti (ed.), pages 259–311 (Academic Press, Inc. 1998)). In the latter technique, single alanine mutations are introduced at every residue in the molecule, and the resultant mutant molecules are tested for biological activity to identify amino acid residues that are critical to the activity of the molecule. See also, Hilton et al., *J. Biol. Chem.* 271:4699 (1996).

The location of Zsig62 receptor binding domains can also be determined by physical analysis of structure, as determined by such techniques as nuclear magnetic resonance, crystallography, electron diffraction or photoaffinity labeling, in conjunction with mutation of putative contact site amino acids. See, for example, de Vos et al., *Science*

255:306 (1992), Smith et al., *J. Mol. Biol.* 224:899 (1992), and Wlodaver et al., *FEBS Lett.* 309:59 (1992). Moreover, Zsig62 labeled with biotin or FITC can be used for expression cloning of Zsig62 receptors.

Multiple amino acid substitutions can be made and tested using known methods of mutagenesis and screening, such as those disclosed by Reidhaar-Olson and Sauer (*Science* 241:53 (1988)) or Bowie and Sauer (*Proc. Nat'l Acad. Sci. USA* 86:2152 (1989)). Briefly, these authors disclose methods for simultaneously randomizing two or more positions in a polypeptide, selecting for functional polypeptide, and then sequencing the mutagenized polypeptides to determine the spectrum of allowable substitutions at each position. Other methods that can be used include phage display (e.g., Lowman et al., *Biochem.* 30:10832 (1991), Ladner et al., U.S. Pat. No. 5,223,409, Huse, international publication No. WO 92/06204, and region-directed mutagenesis (Derbyshire et al., *Gene* 46:145 (1986), and Ner et al., *DNA* 7:127, (1988)).

Variants of the disclosed Zsig62 nucleotide and polypeptide sequences can also be generated through DNA shuffling as disclosed by Stemmer, *Nature* 370:389 (1994), Stemmer, *Proc. Nat'l Acad. Sci. USA* 91:10747 (1994), and international publication No. WO 97/20078. Briefly, variant DNAs are generated by in vitro homologous recombination by random fragmentation of a parent DNA followed by reassembly using PCR, resulting in randomly introduced point mutations. This technique can be modified by using a family of parent DNAs, such as allelic variants or DNAs from different species, to introduce additional variability into the process. Selection or screening for the desired activity, followed by additional iterations of mutagenesis and assay provides for rapid "evolution" of sequences by selecting for desirable mutations while simultaneously selecting against detrimental changes.

Mutagenesis methods as disclosed herein can be combined with high-throughput, automated screening methods to detect activity of cloned, mutagenized polypeptides in host cells. Mutagenized DNA molecules that encode biologically active polypeptides, or polypeptides that bind with anti-Zsig62 antibodies, can be recovered from the host cells and rapidly sequenced using modem equipment. These methods allow the rapid determination of the importance of individual amino acid residues in a polypeptide of interest, and can be applied to polypeptides of unknown structure.

The present invention also includes "functional fragments" of Zsig62 polypeptides and nucleic acid molecules encoding such functional fragments. Routine deletion analyses of nucleic acid molecules can be performed to obtain functional fragments of a nucleic acid molecule that encodes a Zsig62 polypeptide. As an illustration, DNA molecules having the nucleotide sequence of SEQ ID NO:1 can be digested with Bal31 nuclease to obtain a series of nested deletions. The fragments are then inserted into expression vectors in proper reading frame, and the expressed polypeptides are isolated and tested for the ability to bind anti-Zsig62 antibodies. One alternative to exonuclease digestion is to use oligonucleotide-directed mutagenesis to introduce deletions or stop codons to specify production of a desired fragment. Alternatively, particular fragments of a Zsig62 gene can be synthesized using the polymerase chain reaction.

Methods for identifying functional domains are well-known to those of skill in the art. For example, studies on the truncation at either or both termini of interferons have been summarized by Horisberger and Di Marco, *Pharmac. Ther.* 66:507 (1995). Moreover, standard techniques for functional analysis of proteins are described by, for example, Treuter et al., *Molec. Gen. Genet.* 240:113 (1993), Content et al., "Expression and preliminary deletion analysis of the 42 kDa 2-5A synthetase induced by human interferon," in *Biological Interferon Systems, Proceedings of ISIR-TNO Meeting on Interferon Systems,* Cantell (ed.), pages 65–72 (Nijhoff 1987), Herschman, "The EGF Receptor," in *Control of Animal Cell Proliferation, Vol.* 1, Boynton et al., (eds.) pages 169–199 (Academic Press 1985), Coumailleau et al., *J. Biol. Chem.* 270:29270 (1995); Fukunaga et al., *J. Biol. Chem.* 270:25291 (1995); Yamaguchi et al., *Biochem. Pharmacol.* 50:1295 (1995), and Meisel et al., *Plant Molec. Biol.* 30:1 (1996).

The present invention also contemplates functional fragments of a Zsig62 gene that has amino acid changes, compared with the amino acid sequence of SEQ ID NO:2. A variant Zsig62 gene can be identified on the basis of structure by determining the level of identity with nucleotide and amino acid sequences of SEQ ID NOs:1 and 2, as discussed above. An alternative approach to identifying a variant gene on the basis of structure is to determine whether a nucleic acid molecule encoding a potential variant Zsig62 gene can hybridize to a nucleic acid molecule having the nucleotide sequence of SEQ ID NO:1, as discussed above.

The present invention also provides polypeptide fragments or peptides comprising an epitope-bearing portion of a Zsig62 polypeptide described herein. Such fragments or peptides may comprise an "immunogenic epitope," which is a part of a protein that elicits an antibody response when the entire protein is used as an immunogen. Immunogenic epitope-bearing peptides can be identified using standard methods (see, for example, Geysen et al., *Proc. Nat'l Acad. Sci. USA* 81:3998 (1983)).

In contrast, polypeptide fragments or peptides may comprise an "antigenic epitope," which is a region of a protein molecule to which an antibody can specifically bind. Certain epitopes consist of a linear or contiguous stretch of amino acids, and the antigenicity of such an epitope is not disrupted by denaturing agents. It is known in the art that relatively short synthetic peptides that can mimic epitopes of a protein can be used to stimulate the production of antibodies against the protein (see, for example, Sutcliffe et al., *Science* 219:660 (1983)). Accordingly, antigenic epitope-bearing peptides and polypeptides of the present invention are useful to raise antibodies that bind with the polypeptides described herein.

Antigenic epitope-bearing peptides and polypeptides preferably contain at least four to ten amino acids, at least ten to fifteen amino acids, or about 15 to about 30 amino acids of SEQ ID NO:2. Such epitope-bearing peptides and polypeptides can be produced by fragmenting a Zsig62 polypeptide, or by chemical peptide synthesis, as described herein. Moreover, epitopes can be selected by phage display of random peptide libraries (see, for example, Lane and Stephen, *Curr. Opin. Immunol.* 5:268 (1993), and Cortese et al., *Curr. Opin. Biotechnol.* 7:616 (1996)). Standard methods for identifying epitopes and producing antibodies from small peptides that comprise an epitope are described, for example, by Mole, "Epitope Mapping," in *Methods in Molecular Biology, Vol.* 10, Manson (ed.), pages 105–116 (The Humana Press, Inc. 1992), Price, "Production and Characterization of Synthetic Peptide-Derived Antibodies," in *Monoclonal Antibodies: Production, Engineering and Clinical Application,* Ritter and Ladyman (eds.), pages 60–84 (Cambridge University Press 1995), and Coligan et al. (eds.), *Current Protocols in Immunology,* pages 9.3.1–9.3.5 and pages 9.4.1–9.4.11 (John Wiley & Sons 1997). Regardless of the particular nucleotide sequence of a variant Zsig62 gene, the gene encodes a polypeptide may be characterized by its ability to bind specifically to an anti-Zsig62 antibody.

For any Zsig62 polypeptide, including variants and fusion proteins, one of ordinary skill in the art can readily generate a fully degenerate polynucleotide sequence encoding that variant using the information set forth in Tables 1 and 2 above. Moreover, those of skill in the art can use standard software to devise Zsig62 variants based upon the nucleotide and amino acid sequences described herein. Accordingly, the present invention includes a computer-readable medium encoded with a data structure that provides at least one of the following sequences: SEQ ID NO:1, SEQ ID NO:2, and SEQ ID NO:3. Suitable forms of computer-readable media include magnetic media and optically-readable media. Examples of magnetic media include a hard or fixed drive, a random access memory (RAM) chip, a floppy disk, digital linear tape (DLT), a disk cache, and a ZIP disk. Optically readable media are exemplified by compact discs (e.g., CD-read only memory (ROM), CD-rewritable (RW), and CD-recordable), and digital versatile/video discs (DVD) (e.g., DVD-ROM, DVD-RAM, and DVD+RW).

5. Production of Zsig62 Fusion Proteins

Fusion proteins of Zsig62 can be used to express Zsig62 in a recombinant host, and to isolate expressed Zsig62. As described below, particular Zsig62 fusion proteins also have uses in diagnosis and therapy.

One type of fusion protein comprises a peptide that guides a Zsig62 polypeptide from a recombinant host cell. To direct a Zsig62 polypeptide into the secretory pathway of a eukaryotic host cell, a secretory signal sequence (also known as a signal peptide, a leader sequence, prepro sequence or pre sequence) is provided in the Zsig62 expression vector. While the secretory signal sequence may be derived from Zsig62, a suitable signal sequence may also be derived from another secreted protein or synthesized de novo. The secretory signal sequence is operably linked to a Zsig62-encoding sequence such that the two sequences are joined in the correct reading frame and positioned to direct the newly synthesized polypeptide into the secretory pathway of the host cell. Secretory signal sequences are commonly positioned 5' to the nucleotide sequence encoding the polypeptide of interest, although certain secretory signal sequences may be positioned elsewhere in the nucleotide sequence of interest (see, e.g., Welch et al., U.S. Pat. No. 5,037,743; Holland et al., U.S. Pat. No. 5,143,830).

Although the secretory signal sequence of Zsig62 or another protein produced by mammalian cells (e.g., tissue-type plasminogen activator signal sequence, as described, for example, in U.S. Pat. No. 5,641,655) is useful for expression of Zsig62 in recombinant mammalian hosts, a yeast signal sequence is preferred for expression in yeast cells. Examples of suitable yeast signal sequences are those derived from yeast mating phermone α-factor (encoded by the MFαl gene), invertase (encoded by the SUC2 gene), or acid phosphatase (encoded by the PHO5 gene). See, for example, Romanos et al., "Expression of Cloned Genes in Yeast," in *DNA Cloning 2: A Practical Approach*, $2^{nd}$ Edition, Glover and Hames (eds.), pages 123–167 (Oxford University Press 1995).

In bacterial cells, it is often desirable to express a heterologous protein as a fusion protein to decrease toxicity, increase stability, and to enhance recovery of the expressed protein. For example, Zsig62 can be expressed as a fusion protein comprising a glutathione S-transferase polypeptide. Glutathione S-transferease fusion proteins are typically soluble, and easily purifiable from *E. coli* lysates on immobilized glutathione columns. In similar approaches, a Zsig62 fusion protein comprising a maltose binding protein polypeptide can be isolated with an amylose resin column, while a fusion protein comprising the C-terminal end of a truncated Protein A gene can be purified using IgG-Sepharose. Established techniques for expressing a heterologous polypeptide as a fusion protein in a bacterial cell are described, for example, by Williams et al., "Expression of Foreign Proteins in *E. coli* Using Plasmid Vectors and Purification of Specific Polyclonal Antibodies," in *DNA Cloning 2: A Practical Approach*, $2^{nd}$ Edition, Glover and Hames (Eds.), pages 15–58 (Oxford University Press 1995). In addition, commercially available expression systems are available. For example, the PINPOINT Xa protein purification system (Promega Corporation; Madison, Wis.) provides a method for isolating a fusion protein comprising a polypeptide that becomes biotinylated during expression with a resin that comprises avidin.

Peptide tags that are useful for isolating heterologous polypeptides expressed by either prokaryotic or eukaryotic cells include polyHistidine tags (which have an affinity for nickel-chelating resin), c-myc tags, calmodulin binding protein (isolated with calmodulin affinity chromatography), substance P, the RYIRS tag (which binds with anti-RYIRS antibodies), the Glu-Glu tag, and the FLAG tag (which binds with anti-FLAG antibodies). See, for example, Luo et al., *Arch. Biochem. Biophys.* 329:215 (1996), Morganti et al., *Biotechnol. Appl. Biochem.* 23:67 (1996), and Zheng et al., *Gene* 186:55 (1997). Nucleic acid molecules encoding such peptide tags are available, for example, from Sigma-Aldrich Corporation (St. Louis, Mo.).

The present invention also contemplates that the use of the secretory signal sequence contained in the Zsig62 polypeptides of the present invention to direct other polypeptides into the secretory pathway. A signal fusion polypeptide can be made wherein a secretory signal sequence derived from amino acid residues 1 to 31 of SEQ ID NO:2 is operably linked to another polypeptide using methods known in the art and disclosed herein. The secretory signal sequence contained in the fusion polypeptides of the present invention is preferably fused amino-terminally to an additional peptide to direct the additional peptide into the secretory pathway. Such constructs have numerous applications known in the art. For example, these novel secretory signal sequence fusion constructs can direct the secretion of an active component of a normally non-secreted protein, such as a receptor. Such fusions may be used in a transgenic animal or in a cultured recombinant host to direct peptides through the secretory pathway. With regard to the latter, exemplary polypeptides include pharmaceutically active molecules such as Factor VIIa, proinsulin, insulin, follicle stimulating hormone, tissue type plasminogen activator, tumor necrosis factor, interleukins (e.g., interleukin-1 (IL-1), IL-2, IL-3, IL-4, IL-5, IL-6, IL-7, IL-8, IL-9, IL-10, IL-11, IL-12, IL-13, IL-14, and IL-15), colony stimulating factors (e.g., granulocyte-colony stimulating factor (G-CSF) and granulocyte macrophage-colony stimulating factor (GM-CSF)), interferons (e.g., interferons-α, -β, -γ, -ω, -δ, and -τ), the stem cell growth factor designated "S1 factor," erythropoietin, and thrombopoietin. The Zsig62 secretory signal sequence contained in the fusion polypeptides of the present invention is preferably fused amino-terminally to an additional peptide to direct the additional peptide into the secretory pathway. Fusion proteins comprising a Zsig62 secretory signal sequence can be constructed using standard techniques.

Another form of fusion protein comprises a Zsig62 polypeptide and an immunoglobulin heavy chain constant region, typically an Fc fragment, which contains two constant region domains and a hinge region but lacks the variable region. As an illustration, Chang et al, U.S. Pat. No. 5,723,125, describe a fusion protein comprising a human interferon and a human immunoglobulin Fc fragment. The C-terminal of the interferon is linked to the N-terminal of the Fc fragment by a peptide linker moiety. An example of a peptide linker is a peptide comprising primarily a T cell inert sequence, which is immunologically inert. An exemplary peptide linker has the amino acid sequence: GGSGG SGGGG SGGGG S (SEQ ID NO:8). In this fusion protein, a preferred Fc moiety is a human γ4 chain, which is stable in solution and has little or no complement activating activity. Accordingly, the present invention contemplates a Zsig62 fusion protein that comprises a Zsig62 moiety and a human Fc fragment, wherein the C-terminus of the Zsig62 moiety is attached to the N-terminus of the Fc fragment via a peptide linker, such as a peptide consisting of the amino acid sequence of SEQ ID NO:20. The Zsig62 moiety can be a Zsig62 molecule or a fragment thereof.

In another variation, a Zsig62 fusion protein comprises an IgG sequence, a Zsig62 moiety covalently joined to the aminoterminal end of the IgG sequence, and a signal peptide that is covalently joined to the aminoterminal of the Zsig62 moiety, wherein the IgG sequence consists of the following elements in the following order: a hinge region, a $CH_2$ domain, and a $CH_3$ domain. Accordingly, the IgG sequence lacks a $CH_1$ domain. The Zsig62 moiety displays a Zsig62 activity, such as the ability to bind with a Zsig62 receptor. This general approach to producing fusion proteins that comprise both antibody and nonantibody portions has been described by LaRochelle et al., EP 742830 (WO 95/21258).

Fusion proteins comprising a Zsig62 moiety and an Fc moiety can be used, for example, as an in vitro assay tool. For example, the presence of a Zsig62 receptor in a biological sample can be detected using a Zsig62-antibody fusion protein, in which the Zsig62 moiety is used to target the cognate receptor, and a macromolecule, such as Protein A or anti-Fc antibody, is used to detect the bound fusion protein-receptor complex. Moreover, such fusion proteins can be used to identify agonists and antagonists that interfere with the binding of Zsig62 to its receptor. In addition, antibody-Zsig62 fusion proteins, comprising antibody variable domains, are useful as therapeutic proteins, in which the antibody moiety binds with a target antigen, such as a tumor associated antigen.

Fusion proteins can be prepared by methods known to those skilled in the art by preparing each component of the fusion protein and chemically conjugating them. Alternatively, a polynucleotide encoding both components of the fusion protein in the proper reading frame can be generated using known techniques and expressed by the methods described herein. General methods for enzymatic and chemical cleavage of fusion proteins are described, for example, by Ausubel (1995) at pages 16-19 to 16-25.

6. Production of Zsig62 Polypeptides in Cultured Cells

The polypeptides of the present invention, including full-length polypeptides, functional fragments, and fusion proteins, can be produced in recombinant host cells following conventional techniques. To express a Zsig62 gene, a nucleic acid molecule encoding the polypeptide must be operably linked to regulatory sequences that control transcriptional expression in an expression vector and then, introduced into a host cell. In addition to transcriptional regulatory sequences, such as promoters and enhancers, expression vectors can include translational regulatory sequences and a marker gene which is suitable for selection of cells that carry the expression vector.

Expression vectors that are suitable for production of a foreign protein in eukaryotic cells typically contain (1) prokaryotic DNA elements coding for a bacterial replication origin and an antibiotic resistance marker to provide for the growth and selection of the expression vector in a bacterial host; (2) eukaryotic DNA elements that control initiation of transcription, such as a promoter; and (3) DNA elements that control the processing of transcripts, such as a transcription termination/polyadenylation sequence. As discussed above, expression vectors can also include nucleotide sequences encoding a secretory sequence that directs the heterologous polypeptide into the secretory pathway of a host cell. For example, a Zsig62 expression vector may comprise a Zsig62 gene and a secretory sequence derived from a Zsig62 gene or another secreted gene.

Zsig62 proteins of the present invention may be expressed in mammalian cells. Examples of suitable mammalian host cells include African green monkey kidney cells (Vero; ATCC CRL 1587), human embryonic kidney cells (293-HEK; ATCC CRL 1573), baby hamster kidney cells (BHK-21, BHK-570; ATCC CRL 8544, ATCC CRL 10314), canine kidney cells (MDCK; ATCC CCL 34), Chinese hamster ovary cells (CHO-K1; ATCC CCL61; CHO DG44 [Chasin et al., *Som. Cell. Molec. Genet.* 12:555 (1986)]), rat pituitary cells (GH1; ATCC CCL82), HeLa S3 cells (ATCC CCL2.2), rat hepatoma cells (H-4-II-E; ATCC CRL 1548) SV40-transformed monkey kidney cells (COS-1; ATCC CRL 1650) and murine embryonic cells (NIH-3T3; ATCC CRL 1658).

For a mammalian host, the transcriptional and translational regulatory signals may be derived from viral sources, such as adenovirus, bovine papilloma virus, simian virus, or the like, in which the regulatory signals are associated with a particular gene which has a high level of expression. Suitable transcriptional and translational regulatory sequences also can be obtained from mammalian genes, such as actin, collagen, myosin, and metallothionein genes.

Transcriptional regulatory sequences include a promoter region sufficient to direct the initiation of RNA synthesis. Suitable eukaryotic promoters include the promoter of the mouse metallothionein I gene (Hamer et al., *J. Molec. Appl. Genet.* 1:273 (1982)), the TK promoter of Herpes virus (McKnight, *Cell* 31:355 (1982)), the SV40 early promoter (Benoist et al., *Nature* 290:304 (1981)), the Rous sarcoma virus promoter (Gorman et al., *Proc. Nat'l Acad. Sci. USA* 79:6777 (1982)), the cytomegalovirus promoter (Foecking et al., *Gene* 45:101 (1980)), and the mouse mammary tumor virus promoter (see, generally, Etcheverry, "Expression of Engineered Proteins in Mammalian Cell Culture," in *Protein Engineering: Principles and Practice,* Cleland et al. (eds.), pages 163–181 (John Wiley & Sons, Inc. 1996)).

Alternatively, a prokaryotic promoter, such as the bacteriophage T3 RNA polymerase promoter, can be used to control Zsig62 gene expression in mammalian cells if the prokaryotic promoter is regulated by a eukaryotic promoter (Zhou et al., *Mol. Cell. Biol.* 10:4529 (1990), and Kaufman et al., *Nucl. Acids Res.* 19:4485 (1991)).

An expression vector can be introduced into host cells using a variety of standard techniques including calcium phosphate transfection, liposome-mediated transfection, microprojectile-mediated delivery, electroporation, and the like. The transfected cells can be selected and propagated to provide recombinant host cells that comprise the expression vector stably integrated in the host cell genome. Techniques for introducing vectors into eukaryotic cells and techniques for selecting such stable transformants using a dominant selectable marker are described, for example, by Ausubel (1995) and by Murray (ed.), *Gene Transfer and Expression Protocols* (Humana Press 1991).

For example, one suitable selectable marker is a gene that provides resistance to the antibiotic neomycin. In this case, selection is carried out in the presence of a neomycin-type drug, such as G-418 or the like. Selection systems can also be used to increase the expression level of the gene of interest, a process referred to as "amplification." Amplification is carried out by culturing transfectants in the presence of a low level of the selective agent and then increasing the amount of selective agent to select for cells that produce high levels of the products of the introduced genes. A suitable amplifiable selectable marker is dihydrofolate reductase, which confers resistance to methotrexate. Other drug resistance genes (e.g., hygromycin resistance, multidrug resistance, puromycin acetyltransferase) can also be used. Alternatively, markers that introduce an altered phenotype, such as green fluorescent protein, or cell surface proteins such as CD4, CD8, Class I MHC, placental alkaline phosphatase may be used to sort transfected cells from untransfected cells by such means as FACS sorting or magnetic bead separation technology.

Zsig62 polypeptides can also be produced by cultured mammalian cells using a viral delivery system. Exemplary viruses for this purpose include adenovirus, herpesvirus, vaccinia virus and adeno-associated virus (AAV). Adenovirus, a double-stranded DNA virus, is currently the best studied gene transfer vector for delivery of heterologous nucleic acid (for a review, see Becker et al., *Meth. Cell Biol.* 43:161 (1994), and Douglas and Curiel, *Science & Medicine* 4:44 (1997)). Advantages of the adenovirus system include the accommodation of relatively large DNA inserts, the ability to grow to high-titer, the ability to infect a broad range of mammalian cell types, and flexibility that allows use with a large number of available vectors containing different promoters.

By deleting portions of the adenovirus genome, larger inserts (up to 7 kb) of heterologous DNA can be accommodated. These inserts can be incorporated into the viral DNA by direct ligation or by homologous recombination with a co-transfected plasmid. An option is to delete the essential E1 gene from the viral vector, which results in the inability to replicate unless the E1 gene is provided by the host cell. Adenovirus vector-infected human 293 cells (ATCC Nos. CRL-1573, 45504, 45505), for example, can be grown as adherent cells or in suspension culture at relatively high cell density to produce significant amounts of protein (see Gamier et al., *Cytotechnol.* 15:145 (1994)).

Zsig62 genes may also be expressed in other higher eukaryotic cells, such as avian, fungal, insect, yeast, or plant cells. The baculovirus system provides an efficient means to introduce cloned Zsig62 genes into insect cells. Suitable expression vectors are based upon the *Autographa californica* multiple nuclear polyhedrosis virus (AcMNPV), and contain well-known promoters such as Drosophila heat shock protein (hsp) 70 promoter, *Autographa californica* nuclear polyhedrosis virus immediate-early gene promoter (ie-1) and the delayed early 39K promoter, baculovirus p10 promoter, and the *Drosophila metallothionein* promoter. A second method of making recombinant baculovirus utilizes a transposon-based system described by Luckow (Luckow, et al., *J. Virol.* 67:4566 (1993)). This system, which utilizes transfer vectors, is sold in the BAC-to-BAC kit (Life Technologies, Rockville, Md.). This system utilizes a transfer vector, PFASTBAC (Life Technologies) containing a Tn7 transposon to move the DNA encoding the Zsig62 polypeptide into a baculovirus genome maintained in *E. coli* as a large plasmid called a "bacmid." See, Hill-Perkins and Possee, *J. Gen. Virol.* 71:971 (1990), Bonning, et al., *J. Gen. Virol.* 75:1551 (1994), and Chazenbalk, and Rapoport, *J. Biol. Chem.* 270:1543 (1995). In addition, transfer vectors can include an in-frame fusion with DNA encoding an epitope tag at the C- or N-terminus of the expressed Zsig62 polypeptide, for example, a Glu-Glu epitope tag (Grussenmeyer et al., *Proc. Nat'l Acad. Sci.* 82:7952 (1985)). Using a technique known in the art, a transfer vector containing a Zsig62 gene is transformed into *E. coli,* and screened for bacmids which contain an interrupted lacZ gene indicative of recombinant baculovirus. The bacmid DNA containing the recombinant baculovirus genome is then isolated using common techniques.

The illustrative PFASTBAC vector can be modified to a considerable degree. For example, the polyhedrin promoter can be removed and substituted with the baculovirus basic protein promoter (also known as Pcor, p6.9 or MP promoter) which is expressed earlier in the baculovirus infection, and has been shown to be advantageous for expressing secreted proteins (see, for example, Hill-Perkins and Possee, *J. Gen. Virol.* 71:971 (1990), Bonning, et al., *J. Gen. Virol.* 75:1551 (1994), and Chazenbalk and Rapoport, *J. Biol. Chem.* 270:1543 (1995). In such transfer vector constructs, a short or long version of the basic protein promoter can be used. Moreover, transfer vectors can be constructed which replace the native Zsig62 secretory signal sequences with secretory signal sequences derived from insect proteins. For example, a secretory signal sequence from Ecdysteroid Glucosyltransferase (EGT), honey bee Melittin (Invitrogen Corporation; Carlsbad, Calif.), or baculovirus gp67 (PharMingen: San Diego, Calif.) can be used in constructs to replace the native Zsig62 secretory signal sequence.

The recombinant virus or bacmid is used to transfect host cells. Suitable insect host cells include cell lines derived from IPLB-Sf-21, a *Spodoptera frugiperda* pupal ovarian cell line, such as Sf9 (ATCC CRL 1711), Sf21AE, and Sf21 (Invitrogen Corporation; San Diego, Calif.), as well as Drosophila Schneider-2 cells, and the HIGH FIVEO cell line (Invitrogen) derived from *Trichoplusia ni* (U.S. Pat. No. 5,300,435). Commercially available serum-free media can be used to grow and to maintain the cells. Suitable media are Sf900 II™ (Life Technologies) or ESF 921™ (Expression Systems) for the Sf9 cells; and Ex-cellO405™ (JRH Biosciences, Lenexa, Kans.) or Express FiveO™ (Life Technologies) for the *T. ni* cells. When recombinant virus is used, the cells are typically grown up from an inoculation density of approximately $2-5 \times 10^5$ cells to a density of $1-2 \times 10^6$ cells at which time a recombinant viral stock is added at a multiplicity of infection (MOI) of 0.1 to 10, more typically near 3.

Established techniques for producing recombinant proteins in baculovirus systems are provided by Bailey et al., "Manipulation of Baculovirus Vectors," in *Methods in Molecular Biology, Volume 7: Gene Transfer and Expression Protocols,* Murray (ed.), pages 147–168 (The Humana Press, Inc. 1991), by Patel et al., "The baculovirus expression system," in *DNA Cloning 2: Expression Systems, 2nd Edition,* Glover et al. (eds.), pages 205–244 (Oxford University Press 1995), by Ausubel (1995) at pages 16–37 to 16–57, by Richardson (ed.), *Baculovirus Expression Protocols* (The Humana Press, Inc. 1995), and by Lucknow, "Insect Cell Expression Technology," in *Protein Engineering: Principles and Practice,* Cleland et al. (eds.), pages 183–218 (John Wiley & Sons, Inc. 1996).

Fungal cells, including yeast cells, can also be used to express the genes described herein. Yeast species of particular interest in this regard include *Saccharomyces cerevisiae*, *Pichia pastoris*, and *Pichia methanolica*. Suitable promoters for expression in yeast include promoters from GAL1 (galactose), PGK (phosphoglycerate kinase), ADH (alcohol dehydrogenase), AOX1 (alcohol oxidase), HIS4 (histidinol dehydrogenase), and the like. Many yeast cloning vectors have been designed and are readily available. These vectors include YIp-based vectors, such as YIp5, YRp vectors, such as YRp17, YEp vectors such as YEp13 and YCp vectors, such as YCp19. Methods for transforming *S. cerevisiae* cells with exogenous DNA and producing recombinant polypeptides therefrom are disclosed by, for example, Kawasaki, U.S. Pat. No. 4,599,311, Kawasaki et al., U.S. Pat. No. 4,931,373, Brake, U.S. Pat. No. 4,870,008, Welch et al., U.S. Pat. No. 5,037,743, and Murray et al., U.S. Pat. No. 4,845,075. Transformed cells are selected by phenotype determined by the selectable marker, commonly drug resistance or the ability to grow in the absence of a particular nutrient (e.g., leucine). A suitable vector system for use in *Saccharomyces cerevisiae* is the POT1 vector system disclosed by Kawasaki et al. (U.S. Pat. No. 4,931,373), which allows transformed cells to be selected by growth in glucose-containing media. Additional suitable promoters and terminators for use in yeast include those from glycolytic enzyme genes (see, e.g., Kawasaki, U.S. Pat. No. 4,599,311, Kingsman et al., U.S. Pat. No. 4,615,974, and Bitter, U.S. Pat. No. 4,977,092) and alcohol dehydrogenase genes. See also U.S. Pat. Nos. 4,990,446, 5,063,154, 5,139,936, and 4,661,454.

Transformation systems for other yeasts, including *Hansenula polymorpha*, *Schizosaccharomyces pombe*, *Kluyveromyces lactis*, *Kluyveromyces fragilis*, *Ustilago maydis*, *Pichia pastoris*, *Pichia methanolica*, *Pichia guillermondii* and *Candida maltosa* are known in the art. See, for example, Gleeson et al., *J. Gen. Microbiol.* 132:3459 (1986), and Cregg, U.S. Pat. No. 4,882,279. Aspergillus cells may be utilized according to the methods of McKnight et al., U.S. Pat. No. 4,935,349. Methods for transforming *Acremonium chrysogenum* are disclosed by Sumino et al., U.S. Pat. No. 5,162,228. Methods for transforming Neurospora are disclosed by Lambowitz, U.S. Pat. No. 4,486,533.

For example, the use of *Pichia methanolica* as host for the production of recombinant proteins is disclosed by Raymond, U.S. Pat. No. 5,716,808, Raymond, U.S. Pat. No. 5,736,383, Raymond et al., *Yeast* 14:11–23 (1998), and in international publication Nos. WO 97/17450, WO 97/17451, WO 98/02536, and WO 98/02565. DNA molecules for use in transforming *P. methanolica* will commonly be prepared as double-stranded, circular plasmids, which can be linearized prior to transformation. For polypeptide production in *P. methanolica*, it is preferred that the promoter and terminator in the plasmid be that of a *P. methanolica* gene, such as a *P. methanolica* alcohol utilization gene (AUG1 or AUG2). Other useful promoters include those of the dihydroxyacetone synthase (DHAS), formate dehydrogenase (FMD), and catalase (CAT) genes. To facilitate integration of the DNA into the host chromosome, it is preferred to have the entire expression segment of the plasmid flanked at both ends by host DNA sequences. A suitable selectable marker for use in *Pichia methanolica* is a *P. methanolica* ADE2 gene, which encodes phosphoribosyl-5-aminoimidazole carboxylase (AIRC; EC 4.1.1.21), and which allows ade2 host cells to grow in the absence of adenine. For large-scale, industrial processes where it is desirable to minimize the use of methanol, it is preferred to use host cells in which both methanol utilization genes (AUG1 and AUG2) are deleted. For production of secreted proteins, host cells deficient in vacuolar protease genes (PEP4 and PRB1) are preferred. Electroporation is used to facilitate the introduction of a plasmid containing DNA encoding a polypeptide of interest into *P. methanolica* cells. *P. methanolica* cells can be transformed by electroporation using an exponentially decaying, pulsed electric field having a field strength of from 2.5 to 4.5 kV/cm, preferably about 3.75 kV/cm, and a time constant (t) of from 1 to 40 milliseconds, most preferably about 20 milliseconds.

Expression vectors can also be introduced into plant protoplasts, intact plant tissues, or isolated plant cells. Methods for introducing expression vectors into plant tissue include the direct infection or co-cultivation of plant tissue with *Agrobacterium tumefaciens*, microprojectile-mediated delivery, DNA injection, electroporation, and the like. See, for example, Horsch et al., *Science* 227:1229 (1985), Klein et al., *Biotechnology* 10:268 (1992), and Miki et al., "Procedures for Introducing Foreign DNA into Plants," in *Methods in Plant Molecular Biology and Biotechnology*, Glick et al. (eds.), pages 67–88 (CRC Press, 1993).

Alternatively, Zsig62 genes can be expressed in prokaryotic host cells. Suitable promoters that can be used to express Zsig62 polypeptides in a prokaryotic host are well-known to those of skill in the art and include promoters capable of recognizing the T4, T3, Sp6 and T7 polymerases, the $P_R$ and $P_L$ promoters of bacteriophage lambda, the trp, recA, heat shock, lacUV5, tac, lpp-lacSpr, phoA, and lacZ promoters of *E. coli*, promoters of *B. subtilis*, the promoters of the bacteriophages of Bacillus, Streptomyces promoters, the int promoter of bacteriophage lambda, the bla promoter of pBR322, and the CAT promoter of the chloramphenicol acetyl transferase gene. Prokaryotic promoters have been reviewed by Glick, *J. Ind. Microbiol.* 1:277 (1987), Watson et al., *Molecular Biology of the Gene*, 4th Ed. (Benjamin Cummins 1987), and by Ausubel et al. (1995).

Illustrative prokaryotic hosts include *E. coli* and *Bacillus subtilus*. Suitable strains of *E. coli* include BL21(DE3), BL21(DE3)pLysS, BL21(DE3)pLysE, DH1, DH4I, DH5, DH5I, DH5IF', DH5IMCR, DH10B, DH10B/p3, DH11S, C600, HB101, JM101, JM105, JM109, JM110, K38, RR1, Y1088, Y1089, CSH18, ER1451, and ER1647 (see, for example, Brown (ed.), *Molecular Biology Labfax* (Academic Press 1991)). Suitable strains of *Bacillus subtilus* include BR151, YB886, MI119, MI120, and B170 (see, for example, Hardy, "Bacillus Cloning Methods," in *DNA Cloning: A Practical Approach*, Glover (ed.) (IRL Press 1985)).

When expressing a Zsig62 polypeptide in bacteria such as *E. coli*, the polypeptide may be retained in the cytoplasm, typically as insoluble granules, or may be directed to the periplasmic space by a bacterial secretion sequence. In the former case, the cells are lysed, and the granules are recovered and denatured using, for example, guanidine isothiocyanate or urea. The denatured polypeptide can then be refolded and dimerized by diluting the denaturant, such as by dialysis against a solution of urea and a combination of reduced and oxidized glutathione, followed by dialysis against a buffered saline solution. In the latter case, the polypeptide can be recovered from the periplasmic space in a soluble and functional form by disrupting the cells (by, for example, sonication or osmotic shock) to release the contents of the periplasmic space and recovering the protein, thereby obviating the need for denaturation and refolding.

Methods for expressing proteins in prokaryotic hosts are well-known to those of skill in the art (see, for example, Williams et al., "Expression of foreign proteins in *E. coli* using plasmid vectors and purification of specific polyclonal antibodies," in *DNA Cloning 2: Expression Systems, 2nd Edition,* Glover et al. (eds.), page 15 (Oxford University Press 1995), Ward et al., "Genetic Manipulation and Expression of Antibodies," in *Monoclonal Antibodies: Principles and Applications,* page 137 (Wiley-Liss, Inc. 1995), and Georgiou, "Expression of Proteins in Bacteria," in *Protein Engineering: Principles and Practice,* Cleland et al. (eds.), page 101 (John Wiley & Sons, Inc. 1996)).

Standard methods for introducing expression vectors into bacterial, yeast, insect, and plant cells are provided, for example, by Ausubel (1995).

General methods for expressing and recovering foreign protein produced by a mammalian cell system are provided by, for example, Etcheverry, "Expression of Engineered Proteins in Mammalian Cell Culture," in *Protein Engineering: Principles and Practice,* Cleland et al. (eds.), pages 163 (Wiley-Liss, Inc. 1996). Standard techniques for recovering protein produced by a bacterial system is provided by, for example, Grisshammer et al., "Purification of over-produced proteins from *E. coli* cells," in *DNA Cloning* 2: Expression Systems, *2nd Edition,* Glover et al. (eds.), pages 59–92 (Oxford University Press 1995). Established methods for isolating recombinant proteins from a baculovirus system are described by Richardson (ed.), *Baculovirus Expression Protocols* (The Humana Press, Inc. 1995).

As an alternative, polypeptides of the present invention can be synthesized by exclusive solid phase synthesis, partial solid phase methods, fragment condensation or classical solution synthesis. These synthesis methods are well-known to those of skill in the art (see, for example, Merrifield, *J. Am. Chem. Soc.* 85:2149 (1963), Stewart et al., "Solid Phase Peptide Synthesis" (2nd Edition), (Pierce Chemical Co. 1984), Bayer and Rapp, *Chem. Pept. Prot.* 3:3 (1986), Atherton et al., *Solid Phase Peptide Synthesis: A Practical Approach* (IRL Press 1989), Fields and Colowick, "Solid-Phase Peptide Synthesis," *Methods in Enzymology* Volume 289 (Academic Press 1997), and Lloyd-Williams et al., *Chemical Approaches to the Synthesis of Peptides and Proteins* (CRC Press, Inc. 1997)). Variations in total chemical synthesis strategies, such as "native chemical ligation" and "expressed protein ligation" are also standard (see, for example, Dawson et al., *Science* 266:776 (1994), Hackeng et al., *Proc. Nat'l Acad. Sci. USA* 94:7845 (1997), Dawson, *Methods Enzymol.* 287: 34 (1997), Muir et al, *Proc. Nat'l Acad. Sci. USA* 95:6705 (1998), and Severinov and Muir, *J. Biol. Chem.* 273:16205 (1998)).

Peptides and polypeptides of the present invention comprise at least six, at least nine, or at least 15 contiguous amino acid residues of SEQ ID NO:2. As an illustration, polypeptides can comprise at least six, at least nine, or at least 15 contiguous amino acid residues of any of the following amino acid sequences of SEQ ID NO:2: (a) amino acid residues 1 to 99, (b) amino acid residues 32 to 99 of SEQ ID NO:2, (c) amino acid residues 32 to 94, (d) amino acid residues 1 to 94, (e) amino acid residues 39 to 99, (f) amino acid residues 39 to 94, and (g) an amino acid sequence of (c), (d), or (f), wherein the last amino acid residue of the recited sequence is amidated. Illustrative polypeptides include polypeptides that either comprise, or consist of, amino acid residues (a) to (g). Within certain embodiments of the invention, the polypeptides comprise 20, 30, 40, 50, or more contiguous residues of these amino acid sequences. Nucleic acid molecules encoding such peptides and polypeptides are useful as polymerase chain reaction primers and probes.

7. Isolation of Zsig62 Polypeptides

The polypeptides of the present invention can be purified to at least about 80% purity, to at least about 90% purity, to at least about 95% purity, or even greater than 95% purity with respect to contaminating macromolecules, particularly other proteins and nucleic acids, and free of infectious and pyrogenic agents. The polypeptides of the present invention may also be purified to a pharmaceutically pure state, which is greater than 99.9% pure. Certain preparations comprise a purified polypeptide that is substantially free of other polypeptides, particularly other polypeptides of animal origin.

Fractionation and/or conventional purification methods can be used to obtain preparations of Zsig62 purified from natural sources (e.g., pancreatic islet cells, or placental, spinal cord, pituitary, and prostate tissues), and recombinant Zsig62 polypeptides and fusion Zsig62 polypeptides purified from recombinant host cells. In general, ammonium sulfate precipitation and acid or chaotrope extraction may be used for fractionation of samples. Exemplary purification steps may include hydroxyapatite, size exclusion, FPLC and reverse-phase high performance liquid chromatography. Suitable chromatographic media include derivatized dextrans, agarose, cellulose, polyacrylamide, specialty silicas, and the like. PEI, DEAE, QAE and Q derivatives are preferred. Exemplary chromatographic media include those media derivatized with phenyl, butyl, or octyl groups, such as Phenyl-Sepharose FF (Pharmacia), Toyopearl butyl 650 (Toso Haas, Montgomeryville, Pa.), Octyl-Sepharose (Pharmacia) and the like; or polyacrylic resins, such as Amberchrom CG 71 (Toso Haas) and the like. Suitable solid supports include glass beads, silica-based resins, cellulosic resins, agarose beads, cross-linked agarose beads, polystyrene beads, cross-linked polyacrylamide resins and the like that are insoluble under the conditions in which they are to be used. These supports may be modified with reactive groups that allow attachment of proteins by amino groups, carboxyl groups, sulfhydryl groups, hydroxyl groups and/or carbohydrate moieties.

Examples of coupling chemistries include cyanogen bromide activation, N-hydroxysuccinimide activation, epoxide activation, sulfhydryl activation, hydrazide activation, and carboxyl and amino derivatives for carbodiimide coupling chemistries. These and other solid media are well known and widely used in the art, and are available from commercial suppliers. Selection of a particular method for polypeptide isolation and purification is a matter of routine design and is determined in part by the properties of the chosen support. See, for example, *Affinity Chromatography: Principles & Methods* (Pharmacia LKB Biotechnology 1988), and Doonan, *Protein Purification Protocols* (The Humana Press 1996).

Additional variations in Zsig62 isolation and purification can be devised by those of skill in the art. For example, anti-Zsig62 antibodies, obtained as described below, can be used to isolate large quantities of protein by immunoaffinity purification. Moreover, methods for binding ligands, such as Zsig62, to receptor polypeptides bound to support media are well known in the art.

The polypeptides of the present invention can also be isolated by exploitation of particular properties. For example, immobilized metal ion adsorption (IMAC) chromatography can be used to purify histidine-rich proteins, including those comprising polyhistidine tags. Briefly, a gel is first charged with divalent metal ions to form a chelate (Sulkowski, *Trends in Biochem.* 3:1 (1985)). Histidine-rich proteins will be adsorbed to this matrix with differing affinities, depending upon the metal ion used, and will be eluted by competitive elution, lowering the pH, or use of strong chelating agents. Other methods of purification include purification of glycosylated proteins by lectin affinity chromatography and ion exchange chromatography (M. Deutscher, (ed.), *Meth. Enzymol.* 182:529 (1990)). Within additional embodiments of the invention, a fusion of the polypeptide of interest and an affinity tag (e.g., maltose-binding protein, an immunoglobulin domain) may be constructed to facilitate purification.

Zsig62 polypeptides or fragments thereof may also be prepared through chemical synthesis, as described below. Zsig62 polypeptides may be monomers or multimers; glycosylated or non-glycosylated; pegylated or non-pegylated; and may or may not include an initial methionine amino acid residue.

8. Zsig62 Analogs and the Zsig62 Receptor

One general class of Zsig62 analogs are variants having an amino acid sequence that is a mutation of the amino acid sequence disclosed herein. Another general class of Zsig62 analogs is provided by anti-idiotype antibodies, and fragments thereof, as described below. Moreover, recombinant antibodies comprising anti-idiotype variable domains can be used as analogs (see, for example, Monfardini et al., *Proc. Assoc. Am. Physicians* 108:420 (1996)). Since the variable domains of anti-idiotype Zsig62 antibodies mimic Zsig62, these domains can provide either Zsig62 agonist or antagonist activity. As an illustration, Lim and Langer, *J. Interferon Res.* 13:295 (1993), describe anti-idiotypic interferon-a antibodies that have the properties of either interferon-α agonists or antagonists.

Another approach to identifying Zsig62 analogs is provided by the use of combinatorial libraries. Methods for constructing and screening phage display and other combinatorial libraries are provided, for example, by Kay et al., *Phage Display of Peptides and Proteins* (Academic Press 1996), Verdine, U.S. Pat. No. 5,783,384, Kay, et. al., U.S. Pat. No. 5,747,334, and Kauffman et al., U.S. Pat. No. 5,723,323.

Zsig62 and its analogs can be used to identify and to isolate Zsig62 receptors. For example, proteins and peptides of the present invention can be immobilized on a column and used to bind receptor proteins from membrane preparations that are run over the column (Hermanson et al. (eds.), *Immobilized Affinity Ligand Techniques,* pages 195–202 (Academic Press 1992)). Radiolabeled or affinity labeled Zsig62 polypeptides can also be used to identify or to localize Zsig62 receptors in a biological sample (see, for example, Deutscher (ed.), *Methods in Enzymol.,* vol. 182, pages 721–37 (Academic Press 1990); Brunner et al., *Ann. Rev. Biochem.* 62:483 (1993); Fedan et al., *Biochem. Pharmacol.* 33:1167 (1984)). Also see, Varthakavi and Minocha, *J. Gen. Virol.* 77:1875 (1996), who describe the use of anti-idiotype antibodies for receptor identification.

As a receptor ligand, the activity of Zsig62 can be measured by a silicon-based biosensor microphysiometer which measures the extracellular acidification rate or proton excretion associated with receptor binding and subsequent cellular responses. An exemplary device is the CYTOSENSOR Microphysiometer manufactured by Molecular Devices Corp. (Sunnyvale, Calif.). A variety of cellular responses, such as cell proliferation, ion transport, energy production, inflammatory response, regulatory and receptor activation, and the like, can be measured by this method (see, for example, McConnell et al., *Science* 257:1906 (1992), Pitchford et al., *Meth. Enzymol.* 228:84 (1997), Arimilli et al., *J. Immunol. Meth.* 212:49 (1998), and Van Liefde et al., *Eur. J. Pharmacol.* 346:87 (1998)). Moreover, the microphysiometer can be used for assaying adherent or non-adherent eukaryotic cells.

Since energy metabolism is coupled with the use of cellular ATP, any event which alters cellular ATP levels, such as receptor activation and the initiation of signal transduction, will cause a change in cellular acid section. By measuring extracellular acidification changes in cell media over time, therefore, the microphysiometer directly measures cellular responses to various stimuli, including Zsig62, its agonists, or antagonists. Preferably, the microphysiometer is used to measure responses of a Zsig62-responsive eukaryotic cell, compared to a control eukaryotic cell that does not respond to Zsig62 polypeptide. Zsig62 responsive eukaryotic cells comprise cells into which a receptor for Zsig62 has been transfected to create a cell that is responsive to Zsig62, or cells that are naturally responsive to Zsig62. Zsig62 modulated cellular responses are measured by a change (e.g., an increase or decrease in extracellular acidification) in the response of cells exposed to Zsig62, compared with control cells that have not been exposed to Zsig62.

Accordingly, a microphysiometer can be used to identify cells, tissues, or cell lines which respond to a Zsig62 stimulated pathway, and which express a functional Zsig62 receptor. As an illustration, cells that express a functional Zsig62 receptor can be identified by (a) providing test cells, (b) incubating a first portion of the test cells in the absence of Zsig62, (c) incubating a second portion of the test cells in the presence of Zsig62, and (d) detecting a change (e.g., an increase or decrease in extracellular acidification rate, as measured by a microphysiometer) in a cellular response of the second portion of the test cells, as compared to the first portion of the test cells, wherein such a change in cellular response indicates that the test cells express a functional Zsig62 receptor. An additional negative control may be included in which a portion of the test cells is incubated with Zsig62 and an anti-Zsig62 antibody to inhibit the binding of Zsig62 with its cognate receptor.

The microphysiometer also provides one means to identify Zsig62 agonists. For example, agonists of Zsig62 can be identified by a method, comprising the steps of (a) providing cells responsive to Zsig62, (b) incubating a first portion of the cells in the absence of a test compound, (c) incubating a second portion of the cells in the presence of a test compound, and (d) detecting a change, for example, an increase or diminution, in a cellular response of the second portion of the cells as compared to the first portion of the cells, wherein such a change in cellular response indicates that the test compound is a Zsig62 agonist. An illustrative change in cellular response is a measurable change in extracellular acidification rate, as measured by a microphysiometer. Moreover, incubating a third portion of the cells in the presence of Zsig62 and in the absence of a test compound can be used as a positive control for the Zsig62 responsive cells, and as a control to compare the agonist activity of a test compound with that of Zsig62. An additional control may be included in which a portion of the cells is incubated with a test compound (or Zsig62) and an anti-Zsig62 antibody to inhibit the binding of the test compound (or Zsig62) with the Zsig62 receptor.

A Zsig62 variant gene product that lacks biological activity may be a Zsig62 antagonist. These biologically-inactive Zsig62 variants can be initially identified on the basis of hybridization analysis, sequence identity determination, or by the ability to specifically bind anti-Zsig62 antibody. A Zsig62 antagonist can be further characterized by its ability to inhibit the biological response induced by Zsig62 or by a Zsig62 agonist. This inhibitory effect may result, for example, from the competitive or non-competitive binding of the antagonist to the Zsig62 receptor.

The microphysiometer provides one means to identify Zsig62 antagonists. For example, Zsig62 antagonists can be identified by a method, comprising the steps of (a) providing cells responsive to Zsig62, (b) incubating a first portion of the cells in the presence of Zsig62 and in the absence of a test compound, (c) incubating a second portion of the cells in the presence of both Zsig62 and the test compound, and (d) comparing the cellular responses of the first and second cell portions, wherein a decreased response by the second portion, compared with the response of the first portion, indicates that the test compound is a Zsig62 antagonist. An illustrative change in cellular response is a measurable change extracellular acidification rate, as measured by a microphysiometer.

The present invention contemplates compositions comprising a peptide or polypeptide described herein. Such compositions can further comprise a carrier.

The carrier can be a conventional organic or inorganic carrier. Examples of carriers include water, buffer solution, alcohol, propylene glycol, macrogol, sesame oil, corn oil, and the like.

9. Production of Antibodies to Zsig62 Proteins

Antibodies to Zsig62 can be obtained, for example, using the product of a Zsig62 expression vector or Zsig62 isolated from a natural source as an antigen. Particularly useful anti-Zsig62 antibodies "bind specifically" with Zsig62. Antibodies are considered to be specifically binding if the antibodies exhibit at least one of the following two properties: (1) antibodies bind to Zsig62 with a threshold level of binding activity, and (2) antibodies do not significantly cross-react with polypeptides known in the art. With regard to the first characteristic, antibodies specifically bind if they bind to a Zsig62 polypeptide, peptide or epitope with a binding affinity ($K_a$) of $10^6$ $M^{-1}$ or greater, preferably $10^7$ $M^{-1}$ or greater, more preferably $10^8$ $M^{-1}$ or greater, and most preferably $10^9$ $M^{-1}$ or greater. The binding affinity of an antibody can be readily determined by one of ordinary skill in the art, for example, by Scatchard analysis (Scatchard, *Ann. NY Acad. Sci.* 51:660 (1949)).

Anti-Zsig62 antibodies can be produced using antigenic Zsig62 epitope-bearing peptides and polypeptides. Antigenic epitope-bearing peptides and polypeptides of the present invention contain a sequence of at least six, preferably between 15 to about 30 amino acids contained within SEQ ID NO:2. However, peptides or polypeptides comprising a larger portion of an amino acid sequence of the invention, containing from 30 to 50 amino acids, or any length up to and including the entire amino acid sequence of a polypeptide of the invention, also are useful for inducing antibodies that bind with Zsig62. It is desirable that the amino acid sequence of the epitope-bearing peptide is selected to provide substantial solubility in aqueous solvents (i.e., the sequence includes relatively hydrophilic residues, while hydrophobic residues are preferably avoided). Moreover, amino acid sequences containing proline residues may be also be desirable for antibody production.

As an illustration, potential antigenic sites in Zsig62 were identified using the Jameson-Wolf method, Jameson and Wolf, *CABIOS* 4:181, (1988), as implemented by the PROTEAN program (version 3.14) of LASERGENE (DNASTAR; Madison, Wis.). Default parameters were used in this analysis.

The Jameson-Wolf method predicts potential antigenic determinants by combining six major subroutines for protein structural prediction. Briefly, the Hopp-Woods method, Hopp et al., *Proc. Nat'l Acad. Sci. USA* 78:3824 (1981), was first used to identify amino acid sequences representing areas of greatest local hydrophilicity (parameter: seven residues averaged). In the second step, Emini's method, Emini et al., *J. Virology* 55:836 (1985), was used to calculate surface probabilities (parameter: surface decision threshold (0.6)=1). Third, the Karplus-Schultz method, Karplus and Schultz, *Naturwissenschaften* 72:212 (1985), was used to predict backbone chain flexibility (parameter: flexibility threshold (0.2)=1). In the fourth and fifth steps of the analysis, secondary structure predictions were applied to the data using the methods of Chou-Fasman, Chou, "Prediction of Protein Structural Classes from Amino Acid Composition," in *Prediction of Protein Structure and the Principles of Protein Conformation,* Fasman (ed.), pages 549–586 (Plenum Press 1990), and Garnier-Robson, Garnier et al., *J. Mol. Biol.* 120:97 (1978) (Chou-Fasman parameters: conformation table=64 proteins; α region threshold=103; β region threshold=105; Garnier-Robson parameters: α and β decision constants=0). In the sixth subroutine, flexibility parameters and hydropathy/solvent accessibility factors were combined to determine a surface contour value, designated as the "antigenic index." Finally, a peak broadening function was applied to the antigenic index, which broadens major surface peaks by adding 20, 40, 60, or 80% of the respective peak value to account for additional free energy derived from the mobility of surface regions relative to interior regions. This calculation was not applied, however, to any major peak that resides in a helical region, since helical regions tend to be less flexible.

The results of this analysis indicated that a peptide consisting of amino acids 28 to 33 of SEQ ID NO:2 ("antigenic peptide 1") or a peptide consisting of amino acids 29 to 34 of SEQ ID NO:2 ("antigenic peptide 2") would be suitable antigenic peptides. The analysis also indicated that the following amino acid sequences of SEQ ID NO:2 would provide suitable antigenic peptides: amino acids 86 to 96 ("antigenic peptide 3"), amino acids 86 to 91 ("antigenic peptide 4"), amino acids 87 to 92 ("antigenic peptide 5"), amino acids 88 to 93 ("antigenic peptide 6"), amino acids 89 to 94 ("antigenic peptide 7"), amino acids 90 to 95 ("antigenic peptide 8"), and amino acids 91 to 96 ("antigenic peptide 9"). The present invention contemplates the use of any one of antigenic peptides 1 to 9 to generate antibodies to Zsig62. The present invention also contemplates polypeptides comprising at least one of antigenic peptides 1 to 9.

Polyclonal antibodies to recombinant Zsig62 protein or to Zsig62 isolated from natural sources can be prepared using methods well-known to those of skill in the art. See, for example, Green et al., "Production of Polyclonal Antisera," in *Immunochemical Protocols* (Manson, ed.), pages 1–5 (Humana Press 1992), and Williams et al., "Expression of foreign proteins in *E. coli* using plasmid vectors and purification of specific polyclonal antibodies," in *DNA Cloning 2: Expression Systems, 2nd Edition,* Glover et al. (eds.), page 15 (Oxford University Press 1995). The immunogenicity of a Zsig62 polypeptide can be increased through the use of an adjuvant, such as alum (aluminum hydroxide) or Freund's complete or incomplete adjuvant. Polypeptides useful for immunization also include fusion polypeptides, such as fusions of Zsig62 or a portion thereof with an immunoglobulin polypeptide or with maltose binding protein. The polypeptide immunogen may be a full-length molecule or a portion thereof. If the polypeptide portion is "hapten-like," such portion may be advantageously joined or linked to a macromolecular carrier (such as keyhole limpet hemocyanin (KLH), bovine serum albumin (BSA) or tetanus toxoid) for immunization.

Although polyclonal antibodies are typically raised in animals such as horses, cows, dogs, chicken, rats, mice, rabbits, guinea pigs, goats, or sheep, an anti-Zsig62 antibody of the present invention may also be derived from a subhuman primate antibody. General techniques for raising diagnostically and therapeutically useful antibodies in baboons may be found, for example, in Goldenberg et al., international patent publication No. WO 91/11465, and in Losman et al., *Int. J. Cancer* 46:310 (1990).

Alternatively, monoclonal anti-Zsig62 antibodies can be generated. Rodent monoclonal antibodies to specific antigens may be obtained by methods known to those skilled in the art (see, for example, Kohler et al., *Nature* 256:495 (1975), Coligan et al. (eds.), *Current Protocols in Immunology, Vol.* 1, pages 2.5.1–2.6.7 (John Wiley & Sons 1991) ["Coligan"], Picksley et al., "Production of monoclonal antibodies against proteins expressed in *E. coli*," in *DNA Cloning 2: Expression Systems, 2nd Edition,* Glover et al. (eds.), page 93 (Oxford University Press 1995)).

Briefly, monoclonal antibodies can be obtained by injecting mice with a composition comprising a Zsig62 gene product, verifying the presence of antibody production by removing a serum sample, removing the spleen to obtain B-lymphocytes, fusing the B-lymphocytes with myeloma cells to produce hybridomas, cloning the hybridomas, selecting positive clones which produce antibodies to the antigen, culturing the clones that produce antibodies to the antigen, and isolating the antibodies from the hybridoma cultures.

In addition, an anti-Zsig62 antibody of the present invention may be derived from a human monoclonal antibody. Human monoclonal antibodies are obtained from transgenic mice that have been engineered to produce specific human antibodies in response to antigenic challenge. In this technique, elements of the human heavy and light chain locus are introduced into strains of mice derived from embryonic stem cell lines that contain targeted disruptions of the endogenous heavy chain and light chain loci. The transgenic mice can synthesize human antibodies specific for human antigens, and the mice can be used to produce human antibody-secreting hybridomas. Methods for obtaining human antibodies from transgenic mice are described, for example, by Green et al., *Nature Genet.* 7:13 (1994), Lonberg et al., *Nature* 368:856 (1994), and Taylor et al., *Int. Immun.* 6:579 (1994).

Monoclonal antibodies can be isolated and purified from hybridoma cultures by a variety of well-established techniques. Such isolation techniques include affinity chromatography with Protein-A Sepharose, size-exclusion chromatography, and ion-exchange chromatography (see, for example, Coligan at pages 2.7.1–2.7.12 and pages 2.9.1–2.9.3; Baines et al., "Purification of Immunoglobulin G (IgG)," in *Methods in Molecular Biology, Vol.* 10, pages 79–104 (The Humana Press, Inc. 1992)).

For particular uses, it may be desirable to prepare fragments of anti-Zsig62 antibodies. Such antibody fragments can be obtained, for example, by proteolytic hydrolysis of the antibody. Antibody fragments can be obtained by pepsin or papain digestion of whole antibodies by conventional methods. As an illustration, antibody fragments can be produced by enzymatic cleavage of antibodies with pepsin to provide a 5S fragment denoted F(ab')$_2$. This fragment can be further cleaved using a thiol reducing agent to produce 3.5S Fab' monovalent fragments. Optionally, the cleavage reaction can be performed using a blocking group for the sulfhydryl groups that result from cleavage of disulfide linkages. As an alternative, an enzymatic cleavage using pepsin produces two monovalent Fab fragments and an Fc fragment directly. These methods are described, for example, by Goldenberg, U.S. Pat. No. 4,331,647, Nisonoff et al., *Arch Biochem. Biophys.* 89:230 (1960), Porter, *Biochem. J.* 73:119 (1959), Edelman et al., in *Methods in Enzymology Vol* 1, page 422 (Academic Press 1967), and by Coligan at pages 2.8.1–2.8.10 and 2.10.–2.10.4.

Other methods of cleaving antibodies, such as separation of heavy chains to form monovalent light-heavy chain fragments, further cleavage of fragments, or other enzymatic, chemical or genetic techniques may also be used, so long as the fragments bind to the antigen that is recognized by the intact antibody.

For example, Fv fragments comprise an association of $V_H$ and $V_L$ chains. This association can be noncovalent, as described by Inbar et al., *Proc. Nat'l Acad. Sci. USA* 69:2659 (1972). Alternatively, the variable chains can be linked by an intermolecular disulfide bond or cross-linked by chemicals such as glutaraldehyde (see, for example, Sandhu, *Crit. Rev. Biotech.* 12:437 (1992)).

The Fv fragments may comprise $V_H$ and $V_L$ chains which are connected by a peptide linker. These single-chain antigen binding proteins (scFv) are prepared by constructing a structural gene comprising DNA sequences encoding the $V_H$ and $V_L$ domains which are connected by an oligonucleotide. The structural gene is inserted into an expression vector which is subsequently introduced into a host cell, such as *E. coli*. The recombinant host cells synthesize a single polypeptide chain with a linker peptide bridging the two V domains. Methods for producing scFvs are described, for example, by Whitlow et al., *Methods: A Companion to Methods in Enzymology* 2:97 (1991) (also see, Bird et al., *Science* 242:423 (1988), Ladner et al., U.S. Pat. No. 4,946,778, Pack et al., *Bio/Technology* 11:1271 (1993), and Sandhu, supra).

As an illustration, a scFV can be obtained by exposing lymphocytes to Zsig62 polypeptide in vitro, and selecting antibody display libraries in phage or similar vectors (for instance, through use of immobilized or labeled Zsig62 protein or peptide). Genes encoding polypeptides having potential Zsig62 polypeptide binding domains can be obtained by screening random peptide libraries displayed on phage (phage display) or on bacteria, such as *E. coli*. Nucleotide sequences encoding the polypeptides can be obtained in a number of ways, such as through random mutagenesis and random polynucleotide synthesis. These random peptide display libraries can be used to screen for peptides which interact with a known target which can be a protein or polypeptide, such as a ligand or receptor, a biological or synthetic macromolecule, or organic or inorganic substances. Techniques for creating and screening such random peptide display libraries are known in the art (Ladner et al., U.S. Pat. No. 5,223,409, Ladner et al., U.S. Pat. No. 4,946,778, Ladner et al., U.S. Pat. No. 5,403,484, Ladner et al., U.S. Pat. No. 5,571,698, and Kay et al., *Phage Display of Peptides and Proteins* (Academic Press, Inc. 1996)) and random peptide display libraries and kits for screening such libraries are available commercially, for instance from CLONTECH Laboratories, Inc. (Palo Alto, Calif.), Invitrogen Inc. (San Diego, Calif.), New England Biolabs, Inc. (Beverly, Mass.), and Pharmacia LKB Biotechnology Inc. (Piscataway, N.J.). Random peptide display libraries can be screened using the Zsig62 sequences disclosed herein to identify proteins which bind to Zsig62.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells (see, for example, Larrick et al., *Methods: A Companion to Methods in Enzymology* 2:106 (1991), Courtenay-Luck, "Genetic Manipulation of Monoclonal Antibodies," in *Monoclonal Antibodies: Production, Engineering and Clinical Application,* Ritter et al. (eds.), page 166 (Cambridge University Press 1995), and Ward et al., "Genetic Manipulation and Expression of Antibodies," in *Monoclonal Antibodies: Principles and Applications,* Birch et al., (eds.), page 137 (Wiley-Liss, Inc. 1995)).

Alternatively, an anti-Zsig62 antibody may be derived from a "humanized" monoclonal antibody. Humanized monoclonal antibodies are produced by transferring mouse complementary determining regions from heavy and light variable chains of the mouse immunoglobulin into a human variable domain. Typical residues of human antibodies are then substituted in the framework regions of the murine counterparts. The use of antibody components derived from humanized monoclonal antibodies obviates potential problems associated with the immunogenicity of murine constant regions. General techniques for cloning murine immunoglobulin variable domains are described, for example, by Orlandi et al., *Proc. Nat'l Acad. Sci. USA* 86:3833 (1989). Techniques for producing humanized monoclonal antibodies are described, for example, by Jones et al., *Nature* 321:522 (1986), Carter et al., *Proc. Nat'l Acad. Sci. USA* 89:4285 (1992), Sandhu, *Crit. Rev. Biotech.* 12:437 (1992), Singer et al., *J. Immun.* 150:2844 (1993), Sudhir (ed.), *Antibody Engineering Protocols* (Humana Press, Inc. 1995), Kelley, "Engineering Therapeutic Antibodies," in *Protein Engineering: Principles and Practice,* Cleland et al. (eds.), pages 399–434 (John Wiley & Sons, Inc. 1996), and by Queen et al., U.S. Pat. No. 5,693,762 (1997).

Polyclonal anti-idiotype antibodies can be prepared by immunizing animals with anti-Zsig62 antibodies or antibody fragments, using standard techniques. See, for example, Green et al., "Production of Polyclonal Antisera," in *Methods In Molecular Biology: Immunochemical Protocols,* Manson (ed.), pages 1–12 (Humana Press 1992). Also, see Coligan at pages 2.4.1–2.4.7. Alternatively, monoclonal anti-idiotype antibodies can be prepared using anti-Zsig62 antibodies or antibody fragments as immunogens with the techniques, described above. As another alternative, humanized anti-idiotype antibodies or subhuman primate anti-idiotype antibodies can be prepared using the above-described techniques. Methods for producing anti-idiotype antibodies are described, for example, by Irie, U.S. Pat. No. 5,208,146, Greene, et. al., U.S. Pat. No. 5,637,677, and Varthakavi and Minocha, *J. Gen. Virol.* 77:1875 (1996).

10. Use of Zsig62 Nucleotide Sequences to Detect Zsig62 Gene Expression and to Examine the Zsig62 Gene Locus Nucleic acid molecules can be used to detect the expression of a Zsig62 gene in a biological sample. Such probe molecules include double-stranded nucleic acid molecules comprising the nucleotide sequence of SEQ ID NO: 1, or a fragment thereof, as well as single-stranded nucleic acid molecules having the complement of the nucleotide sequence of SEQ ID NO:1, or a fragment thereof. Probe molecules may be DNA, RNA, oligonucleotides, and the like.

Certain probes bind with regions of the Zsig62 gene that have a low sequence similarity to comparable regions in other genes. As used herein, the term "portion" refers to at least eight nucleotides to at least 20 or more nucleotides.

In a basic assay, a single-stranded probe molecule is incubated with RNA, isolated from a biological sample, under conditions of temperature and ionic strength that promote base pairing between the probe and target Zsig62 RNA species. After separating unbound probe from hybridized molecules, the amount of hybrids is detected.

Well-established hybridization methods of RNA detection include northern analysis and dot/slot blot hybridization (see, for example, Ausubel (1995) at pages 4-1 to 4-27, and Wu et al. (eds.), "Analysis of Gene Expression at the RNA Level," in *Methods in Gene Biotechnology,* pages 225–239 (CRC Press, Inc. 1997)). Nucleic acid probes can be detectably labeled with radioisotopes such as $^{32}P$ or $^{35}S$. Alternatively, Zsig62 RNA can be detected with a nonradioactive hybridization method (see, for example, Isaac (ed.), *Protocols for Nucleic Acid Analysis by Nonradioactive Probes* (Humana Press, Inc. 1993)). Typically, nonradioactive detection is achieved by enzymatic conversion of chromogenic or chemiluminescent substrates. Illustrative nonradioactive moieties include biotin, fluorescein, and digoxigenin.

Zsig62 oligonucleotide probes are also useful for in vivo diagnosis. As an illustration, $^{18}F$-labeled oligonucleotides can be administered to a subject and visualized by positron emission tomography (Tavitian et al., *Nature Medicine* 4:467 (1998)).

Numerous diagnostic procedures take advantage of the polymerase chain reaction (PCR) to increase sensitivity of detection methods. Standard techniques for performing PCR are well-known (see, generally, Mathew (ed.), *Protocols in Human Molecular Genetics* (Humana Press, Inc. 1991), White (ed.), *PCR Protocols: Current Methods and Applications* (Humana Press, Inc. 1993), Cotter (ed.), *Molecular Diagnosis of Cancer* (Humana Press, Inc. 1996), Hanausek and Walaszek (eds.), *Tumor Marker Protocols* (Humana Press, Inc. 1998), Lo (ed.), *Clinical Applications of PCR* (Humana Press, Inc. 1998), and Meltzer (ed.), *PCR in Bioanalysis* (Humana Press, Inc. 1998)). Particular PCR primers are designed to amplify a portion of the Zsig62 gene that has a low sequence similarity to a comparable region in other genes.

One variation of PCR for diagnostic assays is reverse transcriptase-PCR (RT-PCR). In the RT-PCR technique, RNA is isolated from a biological sample, reverse transcribed to cDNA, and the cDNA is incubated with Zsig62 primers (see, for example, Wu et al. (eds.), "Rapid Isolation of Specific cDNAs or Genes by PCR," in *Methods in Gene Biotechnology,* pages 15–28 (CRC Press, Inc. 1997)). PCR is then performed and the products are analyzed using standard techniques.

As an illustration, RNA is isolated from biological sample using, for example, the guanidinium-thiocyanate cell lysis procedure described above. Alternatively, a solid-phase technique can be used to isolate mRNA from a cell lysate. A reverse transcription reaction can be primed with the isolated RNA using random oligonucleotides, short homopolymers of dT, or Zsig62 anti-sense oligomers. Oligo-dT primers offer the advantage that various mRNA nucleotide sequences are amplified that can provide control target sequences. Zsig62 sequences are amplified by the polymerase chain reaction using two flanking oligonucleotide primers that are typically 20 bases in length.

PCR amplification products can be detected using a variety of approaches. For example, PCR products can be fractionated by gel electrophoresis, and visualized by ethidium bromide staining. Alternatively, fractionated PCR products can be transferred to a membrane, hybridized with a detectably-labeled Zsig62 probe, and examined by autoradiography. Additional alternative approaches include the use of digoxigenin-labeled deoxyribonucleic acid triphosphates to provide chemiluminescence detection, and the C-TRAK calorimetric assay.

Another approach for detection of Zsig62 expression is cycling probe technology, in which a single-stranded DNA target binds with an excess of DNA-RNA-DNA chimeric probe to form a complex, the RNA portion is cleaved with RNAase H, and the presence of cleaved chimeric probe is detected (see, for example, Beggs et al., *J. Clin. Microbiol.* 34:2985 (1996), Bekkaoui et al., *Biotechniques* 20:240 (1996)). Alternative methods for detection of Zsig62 sequences can utilize approaches such as nucleic acid sequence-based amplification, cooperative amplification of templates by cross-hybridization, and the ligase chain reaction (see, for example, Marshall et al., U.S. Pat. No. 5,686,272 (1997), Dyer et al., *J. Virol. Methods* 60:161 (1996), Ehricht et al., *Eur. J. Biochem.* 243:358 (1997), and Chadwick et al., J. Virol. Methods 70:59 (1998)). Other standard methods are known to those of skill in the art.

Zsig62 probes and primers can also be used to detect and to localize Zsig62 gene expression in tissue samples. Methods for such in situ hybridization are well-known to those of skill in the art (see, for example, Choo (ed.), *In Situ Hybridization Protocols* (Humana Press, Inc. 1994), Wu et al. (eds.), "Analysis of Cellular DNA or Abundance of mRNA by Radioactive In Situ Hybridization (RISH)," in *Methods in Gene Biotechnology,* pages 259–278 (CRC Press, Inc. 1997), and Wu et al. (eds.), "Localization of DNA or Abundance of mRNA by Fluorescence In Situ Hybridization (RISH)," in *Methods in Gene Biotechnology,* pages 279–289 (CRC Press, Inc. 1997)). Various additional diagnostic approaches are well-known to those of skill in the art (see, for example, Mathew (ed.), *Protocols in Human Molecular Genetics* (Humana Press, Inc. 1991), Coleman and Tsongalis, *Molecular Diagnostics* (Humana Press, Inc. 1996), and Elles, *Molecular Diagnosis of Genetic Diseases* (Humana Press, Inc., 1996)).

Nucleic acid molecules comprising Zsig62 nucleotide sequences can also be used to determine whether a subject's chromosomes contain a mutation in the Zsig62 gene, which resides at chromosome 16q24.3. Detectable chromosomal aberrations at the Zsig62 gene locus include, but are not limited to, aneuploidy, gene copy number changes, insertions, deletions, restriction site changes and rearrangements. Of particular interest are genetic alterations that inactivate the Zsig62 gene.

As noted above, the Zsig62 gene is expressed in certain tissues but not in tumors derived from those tissues. This observation indicates that the Zsig62 gene may encode a tumor suppressor protein. Tumor suppressor genes can be inactivated by various mechanisms, including loss of heterozygosity (LOH), loss of expression, a mutation, and inactivation by cellular binding protein (see, for example, Gao et al., *Adv. Exp. Med. Biol.* 407:41 (1997)).

With regard to LOH, several studies have shown that the same three small regions of LOH on chromosome 16q are associated with prostate cancer (Suzuki et al., *Genes Chromosomes Cancer* 17:225 (1996), Elo et al., *Cancer Res.* 57:3356 (1997), and Latil et al., *Cancer Res.* 57:1058 (1997)). The Zsig62 gene resides within the most distal of the three regions (16q24.2–q24.3), which is associated with aggressive behavior and metastatic potential in the tumors. The researchers concluded that a gene important in the progression of prostate cancer lies within this region of chromosome 16, and its deletion promotes aggressive and metastatic behavior. Studies have also shown an association between LOH in the 16q24 region and breast cancer (Cleton-Jansen et al., *Genes Chromosomes Cancer* 9:101 (1994), Chen et al., *Cancer Res.* 56:5605 (1996), Driouch et al., *Genes Chromosomes Cancer* 19:185 (1997), Hansen et al., *Cancer Res.* 58:2166 (1998)).

Aberrations associated with the Zsig62 locus can be detected using nucleic acid molecules of the present invention by employing molecular genetic techniques, such as restriction fragment length polymorphism analysis, short tandem repeat analysis employing PCR techniques, amplification-refractory mutation system analysis, single-strand conformation polymorphism detection, RNase cleavage methods, denaturing gradient gel electrophoresis, fluorescence-assisted mismatch analysis, and other genetic analysis techniques known in the art (see, for example, Mathew (ed.), *Protocols in Human Molecular Genetics* (Humana Press, Inc. 1991), Marian, *Chest* 108:255 (1995), Coleman and Tsongalis, *Molecular Diagnostics (Human Press, Inc.* 1996), Elles (ed.) *Molecular Diagnosis of Genetic Diseases* (Humana Press, Inc. 1996), Landegren (ed.), *Laboratory Protocols for Mutation Detection* (Oxford University Press 1996), Birren et al. (eds.), *Genome Analysis, Vol.* 2: *Detecting Genes* (Cold Spring Harbor Laboratory Press 1998), Dracopoli et al. (eds.), *Current Protocols in Human Genetics* (John Wiley & Sons 1998), and Richards and Ward, "Molecular Diagnostic Testing," in *Principles of Molecular Medicine, pages* 83–88 (Humana Press, Inc. 1998)).

The protein truncation test is also useful for detecting the inactivation of a tumor suppressor gene in which translation-terminating mutations produce only portions of the tumor suppressor protein (see, for example, Stoppa-Lyonnet et al., *Blood* 91:3920 (1998)). According to this approach, RNA is isolated from a biological sample, and used to synthesize cDNA. PCR is then used to amplify the Zsig62 target sequence and to introduce an RNA polymerase promoter, a translation initiation sequence, and an in-frame ATG triplet. PCR products are transcribed using an RNA polymerase, and the transcripts are translated in vitro with a T7-coupled reticulocyte lysate system. The translation products are then fractionated by SDS-PAGE to determine the lengths of the translation products. The protein truncation test is described, for example, by Dracopoli et al. (eds.), *Current Protocols in Human Genetics,* pages 9.11.1–9.11.18 (John Wiley & Sons 1998).

The present invention also contemplates kits for detecting Zsig62 gene expression, or to examine the Zsig62 locus. Such kits comprise nucleic acid probes, such as double-stranded nucleic acid molecules comprising the nucleotide sequence of SEQ ID NO:1, or a fragment thereof, as well as single-stranded nucleic acid molecules having the complement of the nucleotide sequence of SEQ ID NO:1, or a fragment thereof. Probe molecules may be DNA, RNA, oligonucleotides, and the like. Kits may comprise nucleic acid primers for performing PCR.

Such a kit can contain all the necessary elements to perform a nucleic acid diagnostic assay described above. A kit will comprise at least one container comprising a Zsig62 probe or primer. The kit may also comprise a second container comprising one or more reagents capable of indicating the presence of Zsig62 sequences. Examples of such indicator reagents include detectable labels such as radioactive labels, fluorochromes, chemiluminescent agents, and the like. A kit may also comprise a means for conveying to the user that the Zsig62 probes and primers are used to detect Zsig62 gene expression. For example, written instructions may state that the enclosed nucleic acid molecules can be used to detect either a nucleic acid molecule that encodes Zsig62, or a nucleic acid molecule having a nucleotide sequence that is complementary to a Zsig62-encoding nucleotide sequence. The written material can be applied directly to a container, or the written material can be provided in the form of a packaging insert.

11. Use of Anti-Zsig62 Antibodies to Detect Zsig62 Protein

The present invention contemplates the use of anti-Zsig62 antibodies to screen biological samples in vitro for the presence of Zsig62. In one type of in vitro assay, anti-Zsig62 antibodies are used in liquid phase. For example, the presence of Zsig62 in a biological sample can be tested by mixing the biological sample with a trace amount of labeled Zsig62 and an anti-Zsig62 antibody under conditions that promote binding between Zsig62 and its antibody. Complexes of Zsig62 and anti-Zsig62 in the sample can be separated from the reaction mixture by contacting the complex with an immobilized protein which binds with the antibody, such as an Fc antibody or Staphylococcus protein A. The concentration of Zsig62 in the biological sample will be inversely proportional to the amount of labeled Zsig62 bound to the antibody and directly related to the amount of free labeled Zsig62.

Alternatively, in vitro assays can be performed in which anti-Zsig62 antibody is bound to a solid-phase carrier. For example, antibody can be attached to a polymer, such as aminodextran, in order to link the antibody to an insoluble support such as a polymer-coated bead, a plate or a tube. Other suitable in vitro assays will be readily apparent to those of skill in the art.

In another approach, anti-Zsig62 antibodies can be used to detect Zsig62 in tissue sections prepared from a biopsy specimen. Such immunochemical detection can be used to determine the relative abundance of Zsig62 and to determine the distribution of Zsig62 in the examined tissue. General immunochemistry techniques are well established (see, for example, Ponder, "Cell Marking Techniques and Their Application," in *Mammalian Development: A Practical Approach*, Monk (ed.), pages 115–38 (IRL Press 1987), Coligan at pages 5.8.1–5.8.8, Ausubel (1995) at pages 14.6.1 to 14.6.13 (Wiley Interscience 1990), and Manson (ed.), *Methods In Molecular Biology, Vol.* 10: *Immunochemical Protocols* (The Humana Press, Inc. 1992)).

Immunochemical detection can be performed by contacting a biological sample with an anti-Zsig62 antibody, and then contacting the biological sample with a detectably labeled molecule which binds to the antibody. For example, the detectably labeled molecule can comprise an antibody moiety that binds to anti-Zsig62 antibody. Alternatively, the anti-Zsig62 antibody can be conjugated with avidin/streptavidin (or biotin) and the detectably labeled molecule can comprise biotin (or avidin/streptavidin). Numerous variations of this basic technique are well-known to those of skill in the art.

Alternatively, an anti-Zsig62 antibody can be conjugated with a detectable label to form an anti-Zsig62 immunoconjugate. Suitable detectable labels include, for example, a radioisotope, a fluorescent label, a chemiluminescent label, an enzyme label, a bioluminescent label or colloidal gold. Methods of making and detecting such detectably-labeled immunoconjugates are well-known to those of ordinary skill in the art, and are described in more detail below.

The detectable label can be a radioisotope that is detected by autoradiography. Isotopes that are particularly useful for the purpose of the present invention are $^3$H, $^{125}$I, $^{131}$I, $^{35}$S and $^{14}$C.

Anti-Zsig62 immunoconjugates can also be labeled with a fluorescent compound. The presence of a fluorescently-labeled antibody is determined by exposing the immunoconjugate to light of the proper wavelength and detecting the resultant fluorescence. Fluorescent labeling compounds include fluorescein isothiocyanate, rhodamine, phycoerytherin, phycocyanin, allophycocyanin, o-phthaldehyde and fluorescamine.

Alternatively, anti-Zsig62 immunoconjugates can be detectably labeled by coupling an antibody component to a chemiluminescent compound. The presence of the chemiluminescent-tagged immunoconjugate is determined by detecting the presence of luminescence that arises during the course of a chemical reaction. Examples of chemiluminescent labeling compounds include luminol, isoluminol, an aromatic acridinium ester, an imidazole, an acridinium salt and an oxalate ester.

Similarly, a bioluminescent compound can be used to label anti-Zsig62 immunoconjugates of the present invention. Bioluminescence is a type of chemiluminescence found in biological systems in which a catalytic protein increases the efficiency of the chemiluminescent reaction. The presence of a bioluminescent protein is determined by detecting the presence of luminescence. Bioluminescent compounds that are useful for labeling include luciferin, luciferase and aequorin.

Alternatively, anti-Zsig62 immunoconjugates can be detectably labeled by linking an anti-Zsig62 antibody component to an enzyme. When the anti-Zsig62-enzyme conjugate is incubated in the presence of the appropriate substrate, the enzyme moiety reacts with the substrate to produce a chemical moiety which can be detected, for example, by spectrophotometric, fluorometric or visual means. Examples of enzymes that can be used to detectably label polyspecific immunoconjugates include β-galactosidase, glucose oxidase, peroxidase and alkaline phosphatase.

Those of skill in the art will know of other suitable labels which can be employed in accordance with the present invention. The binding of marker moieties to anti-Zsig62 antibodies can be accomplished using standard techniques known to the art. Typical methodology in this regard is described by Kennedy et al., *Clin. Chim. Acta* 70:1 (1976), Schurs et al., *Clin. Chim. Acta* 81:1 (1977), Shih et al., *Int'l J. Cancer* 46:1101 (1990), Stein et al., *Cancer Res.* 50:1330 (1990), and Coligan, supra Moreover, the convenience and versatility of immunochemical detection can be enhanced by using anti-Zsig62 antibodies that have been conjugated with avidin, streptavidin, and biotin (see, for example, Wilchek et al. (eds.), "Avidin-Biotin Technology," *Methods In Enzymology, Vol.* 184 (Academic Press 1990), and Bayer et al., "Immunochemical Applications of Avidin-Biotin Technology," in *Methods In Molecular Biology, Vol.* 10, Manson (ed.), pages 149–162 (The Humana Press, Inc. 1992).

Methods for performing immunoassays are well-established. See, for example, Cook and Self, "Monoclonal Antibodies in Diagnostic Immunoassays," in *Monoclonal Antibodies: Production, Engineering, and Clinical Application,* Ritter and Ladyman (eds.), pages 180–208, (Cambridge University Press, 1995), Perry, "The Role of Monoclonal Antibodies in the Advancement of Immunoassay Technology," in *Monoclonal Antibodies: Principles and Applications,* Birch and Lennox (eds.), pages 107–120 (Wiley-Liss, Inc. 1995), and Diamandis, *Immunoassay (Academic Press, Inc.* 1996).

In a related approach, biotin- or FITC-labeled Zsig62 can be used to identify cells that bind Zsig62. Such can binding can be detected, for example, using flow cytometry.

The present invention also contemplates kits for performing an immunological diagnostic assay for Zsig62 gene expression. Such kits comprise at least one container comprising an anti-Zsig62 antibody, or antibody fragment. A kit may also comprise a second container comprising one or more reagents capable of indicating the presence of Zsig62 antibody or antibody fragments. Examples of such indicator reagents include detectable labels such as a radioactive label, a fluorescent label, a chemiluminescent label, an enzyme label, a bioluminescent label, colloidal gold, and the like. A kit may also comprise a means for conveying to the user that Zsig62 antibodies or antibody fragments are used to detect Zsig62 protein. For example, written instructions may state that the enclosed antibody or antibody fragment can be used to detect Zsig62. The written material can be applied directly to a container, or the written material can be provided in the form of a packaging insert.

12. Therapeutic Uses of Polypeptides Having Zsig62 Activity

The present invention includes the use of proteins, polypeptides, and peptides having Zsig62 activity (such as Zsig62 polypeptides, anti-idiotype anti-Zsig62 antibodies, and Zsig62 fusion proteins) to a subject who lacks an adequate amount of this polypeptide. For example, such molecules may be used to treat tumors in which Zsig62 gene expression is reduced. Illustrative tumors include lung, uterus, breast, fallopian tube, ovary, and gall bladder tumors.

Generally, the dosage of administered polypeptide, protein or peptide will vary depending upon such factors as the patient's age, weight, height, sex, general medical condition and previous medical history. Typically, it is desirable to provide the recipient with a dosage of a molecule having Zsig62 activity which is in the range of from about 1 pg/kg to 10 mg/kg (amount of agent/body weight of patient), although a lower or higher dosage also may be administered as circumstances dictate.

Administration of a molecule having Zsig62 activity to a subject can be intravenous, intraarterial, intraperitoneal, intramuscular, subcutaneous, intrapleural, intrathecal, by perfusion through a regional catheter, or by direct intralesional injection. When administering therapeutic proteins by injection, the administration may be by continuous infusion or by single or multiple boluses.

A pharmaceutical composition comprising a protein, polypeptide, or peptide having Zsig62 activity can be formulated according to known methods to prepare pharmaceutically useful compositions, whereby the therapeutic proteins are combined in a mixture with a pharmaceutically acceptable carrier. A composition is said to be a "pharmaceutically acceptable carrier" if its administration can be tolerated by a recipient patient. Sterile phosphate-buffered saline is one example of a pharmaceutically acceptable carrier. Other suitable carriers are well-known to those in the art. See, for example, Gennaro (ed.), *Remington's Pharmaceutical Sciences*, 19th Edition (Mack Publishing Company 1995).

For purposes of therapy, molecules having Zsig62 activity and a pharmaceutically acceptable carrier are administered to a patient in a therapeutically effective amount. A combination of a protein, polypeptide, or peptide having Zsig62 activity and a pharmaceutically acceptable carrier is said to be administered in a "therapeutically effective amount" if the amount administered is physiologically significant. An agent is physiologically significant if its presence results in a detectable change in the physiology of a recipient patient. In the present context, an agent having Zsig62 activity is physiologically significant if it inhibits tumor growth. An inhibition of tumor growth may be indicated, for example, by a decrease in the number of tumor cells, decreased metastasis, a decrease in the size of a solid tumor, or increased necrosis of a tumor.

A pharmaceutical composition comprising molecules having Zsig62 activity can be furnished in liquid form, or in solid form. Liquid forms, including liposome-encapsulated formulations, are illustrated by injectable solutions and oral suspensions. Exemplary solid forms include capsules, tablets, and controlled-release forms, such as a miniosmotic pump or an implant. Other dosage forms can be devised by those skilled in the art, as shown, for example, by Ansel and Popovich, *Pharmaceutical Dosage Forms and Drug Delivery Systems*, 5$^{th}$ Edition (Lea & Febiger 1990), Gennaro (ed.), *Remington's Pharmaceutical Sciences*, 19$^{th}$ Edition (Mack Publishing Company 1995), and by Ranade and Hollinger, *Drug Delivery Systems* (CRC Press 1996).

As an illustration, Zsig62 pharmaceutical compositions may be supplied as a kit comprising a container that comprises Zsig62. Zsig62 can be provided in the form of an injectable solution for single or multiple doses, or as a sterile powder that will be reconstituted before injection. Such a kit may further comprise written information on indications and usage of the pharmaceutical composition. Moreover, such information may include a statement that the Zsig62 composition is contraindicated in patients with known hypersensitivity to Zsig62.

13. Therapeutic Uses of Zsig62 Nucleotide Sequences

The present invention includes the use of Zsig62 nucleotide sequences to provide Zsig62 to a subject in need of such treatment. There are numerous approaches to introduce a Zsig62 gene to a subject, including the use of recombinant host cells that express Zsig62, delivery of naked nucleic acid encoding Zsig62, use of a cationic lipid carrier with a nucleic acid molecule that encodes Zsig62, and the use of viruses that express Zsig62, such as recombinant retroviruses, recombinant adeno-associated viruses, recombinant adenoviruses, and recombinant Herpes simplex viruses (see, for example, Mulligan, *Science* 260:926 (1993), Rosenberg et al., *Science* 242:1575 (1988), LaSalle et al., *Science* 259:988 (1993), Wolff et al., *Science* 247:1465 (1990), Breakfield and Deluca, *The New Biologist* 3:203 (1991)). In an ex vivo approach, for example, cells are isolated from a subject, transfected with a vector that expresses a Zsig62 gene, and then transplanted into the subject.

In order to effect expression of a Zsig62 gene, an expression vector is constructed in which a nucleotide sequence encoding a Zsig62 gene is operably linked to a core promoter, and optionally a regulatory element, to control gene transcription. The general requirements of an expression vector are described above.

Alternatively, a Zsig62 gene can be delivered using recombinant viral vectors, including for example, adenoviral vectors (e.g., Kass-Eisler et al., *Proc. Nat'l Acad. Sci. USA* 90:11498 (1993), Kolls et al., *Proc. Nat'l Acad. Sci. USA* 91:215 (1994), Li et al., *Hum. Gene Ther.* 4:403 (1993), Vincent et al., *Nat. Genet.* 5:130 (1993), and Zabner et al., *Cell* 75:207 (1993)), adenovirus-associated viral vectors (Flotte et al., *Proc. Nat'l Acad. Sci. USA* 90:10613 (1993)), alphaviruses such as Semliki Forest Virus and Sindbis Virus (Hertz and Huang, *J. Vir.* 66:857 (1992), Raju and Huang, *J. Vir.* 65:2501 (1991), and Xiong et al., *Science* 243:1188 (1989)), herpes viral vectors (e.g., U.S. Pat. Nos. 4,769,331, 4,859,587, 5,288,641 and 5,328,688), parvovirus vectors (Koering et al., *Hum. Gene Therap.* 5:457 (1994)), pox virus vectors (Ozaki et al., *Biochem. Biophys. Res. Comm.*

193:653 (1993), Panicali and Paoletti, *Proc. Nat'l Acad. Sci. USA* 79:4927 (1982)), pox viruses, such as canary pox virus or vaccinia virus (Fisher-Hoch et al., *Proc. Nat'l Acad. Sci. USA* 86:317 (1989), and Flexner et al., *Ann. N.Y. Acad. Sci.* 569:86 (1989)), and retroviruses (e.g., Baba et al., *J. Neurosurg* 79:729 (1993), Ram et al., *Cancer Res.* 53:83 (1993), Takamiya et al., *J. Neurosci. Res* 33:493 (1992), Vile and Hart, *Cancer Res.* 53:962 (1993), Vile and Hart, *Cancer Res.* 53:3860 (1993), and Anderson et al., U.S. Pat. No. 5,399,346). Within various embodiments, either the viral vector itself, or a viral particle which contains the viral vector may be utilized in the methods and compositions described below.

As an illustration of one system, adenovirus, a double-stranded DNA virus, is a well-characterized gene transfer vector for delivery of a heterologous nucleic acid molecule (for a review, see Becker et al., *Meth. Cell Biol.* 43:161 (1994); Douglas and Curiel, *Science & Medicine* 4:44 (1997)). The adenovirus system offers several advantages including: (i) the ability to accommodate relatively large DNA inserts, (ii) the ability to be grown to high-titer, (iii) the ability to infect a broad range of mammalian cell types, and (iv) the ability to be used with many different promoters including ubiquitous, tissue specific, and regulatable promoters. In addition, adenoviruses can be administered by intravenous injection, because the viruses are stable in the bloodstream.

Using adenovirus vectors where portions of the adenovirus genome are deleted, inserts are incorporated into the viral DNA by direct ligation or by homologous recombination with a co-transfected plasmid. In an exemplary system, the essential E1 gene is deleted from the viral vector, and the virus will not replicate unless the E1 gene is provided by the host cell. When intravenously administered to intact animals, adenovirus primarily targets the liver. Although an adenoviral delivery system with an E1 gene deletion cannot replicate in the host cells, the host's tissue will express and process an encoded heterologous protein. Host cells will also secrete the heterologous protein if the corresponding gene includes a secretory signal sequence. Secreted proteins will enter the circulation from tissue that expresses the heterologous gene (e.g., the highly vascularized liver).

Moreover, adenoviral vectors containing various deletions of viral genes can be used to reduce or eliminate immune responses to the vector. Such adenoviruses are E1-deleted, and in addition, contain deletions of E2A or E4 (Lusky et al., *J. Virol.* 72:2022 (1998); Raper et al., *Human Gene Therapy* 9:671 (1998)). The deletion of E2b has also been reported to reduce immune responses (Amalfitano et al., *J. Virol.* 72:926 (1998)). By deleting the entire adenovirus genome, very large inserts of heterologous DNA can be accommodated. Generation of so called "gutless" adenoviruses, where all viral genes are deleted, are particularly advantageous for insertion of large inserts of heterologous DNA (for a review, see Yeh. and Perricaudet, *FASEB J.* 11:615 (1997)).

High titer stocks of recombinant viruses capable of expressing a therapeutic gene can be obtained from infected mammalian cells using standard methods. For example, recombinant HSV can be prepared in Vero cells, as described by Brandt et al., *J. Gen. Virol.* 72:2043 (1991), Herold et al., *J. Gen. Virol.* 75:1211 (1994), Visalli and Brandt, *Virology* 185:419 (1991), Grau et al., *Invest. Ophthalmol. Vis. Sci.* 30:2474 (1989), Brandt et al., *J. Virol. Meth.* 36:209 (1992), and by Brown and MacLean (eds.), *HSV Virus Protocols* (Humana Press 1997).

Alternatively, an expression vector comprising a Zsig62 gene can be introduced into a subject's cells by lipofection in vivo using liposomes. Synthetic cationic lipids can be used to prepare liposomes for in vivo transfection of a gene encoding a marker (Felgner et al., *Proc. Nat'l Acad. Sci. USA* 84:7413 (1987); Mackey et al., *Proc. Nat'l Acad. Sci. USA* 85:8027 (1988)). The use of lipofection to introduce exogenous genes into specific organs in vivo has certain practical advantages. Liposomes can be used to direct transfection to particular cell types, which is particularly advantageous in a tissue with cellular heterogeneity, such as the pancreas, liver, kidney, and brain. Lipids may be chemically coupled to other molecules for the purpose of targeting. Targeted peptides (e.g., hormones or neurotransmitters), proteins such as antibodies, or non-peptide molecules can be coupled to liposomes chemically.

Electroporation is another alternative mode of administration of a Zsig62 nucleic acid molecules. For example, Aihara and Miyazaki, *Nature Biotechnology* 16:867 (1998), have demonstrated the use of in vivo electroporation for gene transfer into muscle. In an alternative approach to gene therapy, a therapeutic gene may encode a Zsig62 anti-sense RNA that inhibits the expression of Zsig62. Suitable sequences for Zsig62 anti-sense molecules can be derived from the nucleotide sequences of Zsig62 disclosed herein.

Alternatively, an expression vector can be constructed in which a regulatory element is operably linked to a nucleotide sequence that encodes a ribozyme. Ribozymes can be designed to express endonuclease activity that is directed to a certain target sequence in a mRNA molecule (see, for example, Draper and Macejak, U.S. Pat. No. 5,496,698, McSwiggen, U.S. Pat. No. 5,525,468, Chowrira and McSwiggen, U.S. Pat. No. 5,631,359, and Robertson and Goldberg, U.S. Pat. No. 5,225,337). In the context of the present invention, ribozymes include nucleotide sequences that bind with Zsig62 mRNA.

In another approach, expression vectors can be constructed in which a regulatory element directs the production of RNA transcripts capable of promoting RNase P-mediated cleavage of mRNA molecules that encode a Zsig62 gene. According to this approach, an external guide sequence can be constructed for directing the endogenous ribozyme, RNase P, to a particular species of intracellular mRNA, which is subsequently cleaved by the cellular ribozyme (see, for example, Altman et al., U.S. Pat. No. 5,168,053, Yuan et al., *Science* 263:1269 (1994), Pace et al., international publication No. WO 96/18733, George et al., international publication No. WO 96/21731, and Werner et al., international publication No. WO 97/33991). Preferably, the external guide sequence comprises a ten to fifteen nucleotide sequence complementary to Zsig62 mRNA, and a 3'-NCCA nucleotide sequence, wherein N is preferably a purine. The external guide sequence transcripts bind to the targeted mRNA species by the formation of base pairs between the mRNA and the complementary external guide sequences, thus promoting cleavage of mRNA by RNase P at the nucleotide located at the 5'-side of the base-paired region.

In general, the dosage of a composition comprising a therapeutic vector having a Zsig62 nucleotide acid sequence, such as a recombinant virus, will vary depending upon such factors as the subject's age, weight, height, sex, general medical condition and previous medical history. Suitable routes of administration of therapeutic vectors include intravenous injection, intraarterial injection, intraperitoneal injection, intramuscular injection, intratumoral injection, and injection into a cavity that contains a tumor.

A composition comprising viral vectors, non-viral vectors, or a combination of viral and non-viral vectors of the present invention can be formulated according to known methods to prepare pharmaceutically useful compositions, whereby vectors or viruses are combined in a mixture with a pharmaceutically acceptable carrier. As noted above, a composition, such as phosphate-buffered saline is said to be a "pharmaceutically acceptable carrier" if its administration can be tolerated by a recipient subject. Other suitable carriers are well-known to those in the art (see, for example, *Remington's Pharmaceutical Sciences, 19th Ed.* (Mack Publishing Co. 1995), and *Gilman's the Pharmacological Basis of Therapeutics, 7th Ed.* (MacMillan Publishing Co. 1985)).

For purposes of therapy, a therapeutic gene expression vector, or a recombinant virus comprising such a vector, and a pharmaceutically acceptable carrier are administered to a subject in a therapeutically effective amount. A combination of an expression vector (or virus) and a pharmaceutically acceptable carrier is said to be administered in a "therapeutically effective amount" if the amount administered is physiologically significant. An agent is physiologically significant if its presence results in a detectable change in the physiology of a recipient subject. In the present context, an agent is physiologically significant if its presence inhibits tumor growth. An inhibition of tumor growth may be indicated, for example, by a decrease in the number of tumor cells, decreased metastasis, a decrease in the size of a solid tumor, or increased necrosis of a tumor.

When the subject treated with a therapeutic gene expression vector or a recombinant virus is a human, then the therapy is preferably somatic cell gene therapy. That is, the preferred treatment of a human with a therapeutic gene expression vector or a recombinant virus does not entail introducing into cells a nucleic acid molecule that can form part of a human germ line and be passed onto successive generations (i.e., human germ line gene therapy).

14. Production of Transgenic Mice

Transgenic mice can be engineered to over-express the Zsig62 gene in all tissues or under the control of a tissue-specific or tissue-preferred regulatory element. These overproducers of Zsig62 can be used to characterize the phenotype that results from over-expression, and the transgenic animals can serve as models for human disease caused by excess Zsig62. Transgenic mice that over-express Zsig62 also provide model bioreactors for production of Zsig62, such as soluble Zsig62, in the milk or blood of larger animals. Methods for producing transgenic mice are well-known to those of skill in the art (see, for example, Jacob, "Expression and Knockout of Interferons in Transgenic Mice," in *Overexpression and Knockout of Cytokines in Transgenic Mice,* Jacob (ed.), pages 111–124 (Academic Press, Ltd. 1994), Monastersky and Robl (eds.), *Strategies in Transgenic Animal Science* (ASM Press 1995), and Abbud and Nilson, "Recombinant Protein Expression in Transgenic Mice," in *Gene Expression Systems: Using Nature for the Art of Expression,* Fernandez and Hoeffler (eds.), pages 367–397 (Academic Press, Inc. 1999)).

For example, a method for producing a transgenic mouse that expresses a Zsig62 gene can begin with adult, fertile males (studs) (B6C3f1, 2–8 months of age (Taconic Farms, Germantown, N.Y.)), vasectomized males (duds) (B6D2f1, 2–8 months, (Taconic Farms)), prepubescent fertile females (donors) (B6C3f1, 4-5 weeks, (Taconic Farms)) and adult fertile females (recipients) (B6D2f1, 2–4 months, (Taconic Farms)). The donors are acclimated for one week and then injected with approximately 8 IU/mouse of Pregnant Mare's Serum gonadotrophin (Sigma Chemical Company; St. Louis, Mo.) I.P., and 46–47 hours later, 8 IU/mouse of human Chorionic Gonadotropin (hCG (Sigma)) I.P. to induce superovulation. Donors are mated with studs subsequent to hormone injections. Ovulation generally occurs within 13 hours of hCG injection. Copulation is confirmed by the presence of a vaginal plug the morning following mating.

Fertilized eggs are collected under a surgical scope. The oviducts are collected and eggs are released into urinalysis slides containing hyaluronidase (Sigma). Eggs are washed once in hyaluronidase, and twice in Whitten's W640 medium (described, for example, by Menino and O'Claray, *Biol. Reprod* 77:159 (1986), and Dienhart and Downs, *Zygote* 4:129 (1996)) that has been incubated with 5% $CO_2$, 5% $O_2$, and 90% $N_2$ at 37° C. The eggs are then stored in a 37° C./5% $CO_2$ incubator until microinjection.

Ten to twenty micrograms of plasmid DNA containing a Zsig62 encoding sequence is linearized, gel-purified, and resuspended in 10 mM Tris-HCl (pH 7.4), 0.25 mM EDTA (pH 8.0), at a final concentration of 5–10 nanograms per microliter for microinjection. For example, the Zsig62 encoding sequences can encode a polypeptide comprising amino acid resides 32 to 99 of SEQ ID NO:2.

Plasmid DNA is microinjected into harvested eggs contained in a drop of W640 medium overlaid by warm, $CO_2$-equilibrated mineral oil. The DNA is drawn into an injection needle (pulled from a 0.75 mm ID, 1 mm OD borosilicate glass capillary), and injected into individual eggs. Each egg is penetrated with the injection needle, into one or both of the haploid pronuclei.

Picoliters of DNA are injected into the pronuclei, and the injection needle withdrawn without coming into contact with the nucleoli. The procedure is repeated until all the eggs are injected. Successfully microinjected eggs are transferred into an organ tissue-culture dish with pre-gassed W640 medium for storage overnight in a 37° C./5% $CO_2$ incubator.

The following day, two-cell embryos are transferred into pseudopregnant recipients. The recipients are identified by the presence of copulation plugs, after copulating with vasectomized duds. Recipients are anesthetized and shaved on the dorsal left side and transferred to a surgical microscope. A small incision is made in the skin and through the muscle wall in the middle of the abdominal area outlined by the ribcage, the saddle, and the hind leg, midway between knee and spleen. The reproductive organs are exteriorized onto a small surgical drape. The fat pad is stretched out over the surgical drape, and a baby serrefine (Roboz, Rockville, Md.) is attached to the fat pad and left hanging over the back of the mouse, preventing the organs from sliding back in.

With a fine transfer pipette containing mineral oil followed by alternating W640 and air bubbles, 12–17 healthy two-cell embryos from the previous day's injection are transferred into the recipient. The swollen ampulla is located and holding the oviduct between the ampulla and the bursa, a nick in the oviduct is made with a 28 g needle close to the bursa, making sure not to tear the ampulla or the bursa.

The pipette is transferred into the nick in the oviduct, and the embryos are blown in, allowing the first air bubble to escape the pipette. The fat pad is gently pushed into the peritoneum, and the reproductive organs allowed to slide in. The peritoneal wall is closed with one suture and the skin closed with a wound clip. The mice recuperate on a 37° C. slide warmer for a minimum of four hours.

The recipients are returned to cages in pairs, and allowed 19–21 days gestation. After birth, 19–21 days postpartum is allowed before weaning. The weanlings are sexed and placed into separate sex cages, and a 0.5 cm biopsy (used for genotyping) is snipped off the tail with clean scissors.

Genomic DNA is prepared from the tail snips using, for example, a QIAGEN DNEASY kit following the manufacturer's instructions. Genomic DNA is analyzed by PCR using primers designed to amplify a Zsig62 gene or a selectable marker gene that was introduced in the same plasmid. After animals are confirmed to be transgenic, they are back-crossed into an inbred strain by placing a transgenic female with a wild-type male, or a transgenic male with one or two wild-type female(s). As pups are born and weaned, the sexes are separated, and their tails snipped for genotyping.

To check for expression of a transgene in a live animal, a partial hepatectomy is performed. A surgical prep is made of the upper abdomen directly below the zyphoid process. Using sterile technique, a small 1.5–2 cm incision is made below the sternum and the left lateral lobe of the liver exteriorized. Using 4-0 silk, a tie is made around the lower lobe securing it outside the body cavity. An atraumatic clamp is used to hold the tie while a second loop of absorbable Dexon (American Cyanamid; Wayne, N.J.) is placed proximal to the first tie. A distal cut is made from the Dexon tie and approximately 100 mg of the excised liver tissue is placed in a sterile petri dish. The excised liver section is transferred to a 14 ml polypropylene round bottom tube and snap frozen in liquid nitrogen and then stored on dry ice. The surgical site is closed with suture and wound clips, and the animal's cage placed on a 37° C. heating pad for 24 hours post operatively. The animal is checked daily post operatively and the wound clips removed 7–10 days after surgery. The expression level of Zsig62 mRNA is examined for each transgenic mouse using an RNA solution hybridization assay or polymerase chain reaction.

In addition to producing transgenic mice that over-express Zsig62, it is useful to engineer transgenic mice with either abnormally low or no expression of the gene. Such transgenic mice provide useful models for diseases associated with a lack of Zsig62. As discussed above, Zsig62 gene expression can be inhibited using anti-sense genes, ribozyme genes, or external guide sequence genes. To produce transgenic mice that under-express the Zsig62 gene, such inhibitory sequences are targeted to Zsig62 mRNA. Methods for producing transgenic mice that have abnormally low expression of a particular gene are known to those in the art (see, for example, Wu et al., "Gene Underexpression in Cultured Cells and Animals by Antisense DNA and RNA Strategies," in *Methods in Gene Biotechnology*, pages 205–224 (CRC Press 1997)).

An alternative approach to producing transgenic mice that have little or no Zsig62 gene expression is to generate mice having at least one normal Zsig62 allele replaced by a nonfunctional Zsig62 gene. One method of designing a nonfunctional Zsig62 gene is to insert another gene, such as a selectable marker gene, within a nucleic acid molecule that encodes Zsig62. Standard methods for producing these so-called "knockout mice" are known to those skilled in the art (see, for example, Jacob, "Expression and Knockout of Interferons in Transgenic Mice," in *Overexpression and Knockout of Cytokines in Transgenic Mice*, Jacob (ed.), pages 111–124 (Academic Press, Ltd. 1994), and Wu et al., "New Strategies for Gene Knockout," in *Methods in Gene Biotechnology*, pages 339–365 (CRC Press 1997)).

The present invention, thus generally described, will be understood more readily by reference to the following examples, which is provided by way of illustration and is not intended to be limiting of the present invention.

EXAMPLE 1

Expression of the Zsig62 Gene

A probe for northern analyses was produced using ZC18, 137 (5' CTG ATG CAG CAC TCA AGA CAA TC 3'; SEQ ID NO:4) and ZC18,139 (5' GGC ATT TGT GGG CAG TGT TGG GGC 3'; SEQ ID NO:5) as primers and a clone encoding Zsig62 as template. The probe was a radioactively labeled using a commercially available random priming kit (REDIPRIMEII kit; AMERSHAM PHARMACIA BIOTECH, Inc.; Piscataway, N.J.), following the manufacturer's protocol. The probe was purified using a NUCTRAP push column (STRATAGENE, La Jolla, Calif.). EXPRESSHYB (CLONTECH Laboratories, Inc.; Palo Alto, Calif.) solution was used for the prehybridization and hybridization solutions for the northern blots. Hybridization took place overnight at 65° C. Following hybridization, the blots were washed in 2×SSC, 0.1% SDS at 25° C. for one hour, followed by a wash in 0.1×SSC and 0.1% SDS at 50° C. for one hour. Blots were exposed to film at −80° C. for several days.

The results demonstrated that the Zsig62 gene is expressed in tissue from placenta, spinal cord, total pituitary, prostate, as well as prostate cell lines representing epithelial cells, smooth muscle cells, and stromal muscle cells. In contrast, little or no Zsig62 gene expression was observed in samples obtained from adult brain, fetal brain, heart, kidney, liver, fetal lung, pancreas, skeletal muscle, spleen, testis, thymus, small intestine, colon, peripheral blood lymphocytes, esophageal tumor, normal esophagus, stomach tumor, normal stomach, lung tumor, and the Y-1A adrenal cell line. In a number of instances, differential Zsig62 gene expression was observed in normal and cancerous tissues. Specifically, Zsig62 RNA was detected in tissue from lung, uterus, breast, fallopian tube, ovary, and gall bladder, while little or no Zsig62 gene expression in tumors derived from these organs.

EXAMPLE 2

Chromosomal Localization of the Zsig62 Gene

Zsig62 was mapped to chromosome 16 using the commercially available "GeneBridge 4 Radiation Hybrid Panel" (Research Genetics, Inc., Huntsville, Ala.). The GeneBridge 4 Radiation Hybrid Panel contains amplifiable DNA molecules from each of 93 radiation hybrid clones, plus two control DNA molecules (the HFL donor and the A23 recipient).

For the mapping of Zsig62 with the "GeneBridge 4 RH Panel," 20 µl reactions were set up in a 96-well microtiter plate (STRATAGENE, La Jolla, Calif.) and used in a "RobOCycler Gradient 96" thermal cycler (STRATAGENE). Each of the 95 PCR reactions consisted of: 2 µl 10×KlenTaq PCR reaction buffer (CLONTECH Laboratories, Inc., Palo Alto, Calif.), 1.6 µl dNTPs mix (2.5 mM each, PERKIN-ELMER, Foster City, Calif.), 1 µl sense primer, ZC 19,942 (5' GGA GCT GGC ATC TTC TGA 3'; SEQ ID NO:6), 1 µl antisense primer, ZC 19,943 (5' TCC CCA CCC ACC CAC TAT 3'; SEQ ID NO:7), 2 µl "RediLoad" (Research Genetics, Inc., Huntsville, Ala.), 0.4 µl 50×Advantage KlenTaq Polymerase Mix (Clontech Laboratories, Inc.), 25 ng of DNA from an individual hybrid clone or control and ddH2O for a total volume of 20 µl. The reactions were overlaid with an equal amount of mineral oil and sealed. The PCR cycler conditions were as follows: an initial 1 cycle 5 minute denaturation at 95° C., 40 cycles of a 1 minute denaturation at 95° C., 1 minute annealing at 64° C. and 1.5 minute extension at 72° C., followed by a final 1 cycle extension of 7 minutes at 72° C. The reactions were separated by electrophoresis on a 2% agarose gel (Life Technologies, Inc., Gaithersburg, Md.).

The results showed that Zsig62 maps 0.60 cR_3000 from the framework marker CHLC.GATA86C08 on the chromosome 16 WICGR radiation hybrid map. Proximal and distal framework markers were CHLC.GATA86C08 and D16S520, respectively. The use of surrounding markers positions Zsig62 in the 16q24.3 region on the integrated LDB chromosome 16 map. (The Genetic Location Database, University of Southhampton).

From the foregoing, it will be appreciated that, although specific embodiments of the invention have been described herein for purposes of illustration, various modifications may be made without deviating from the spirit and scope of the invention. Accordingly, the invention is not limited except as by the appended claims.

We claim:

1. An isolated nucleic acid molecule that encodes a polypeptide comprising amino acid residues 39 to 94 of SEQ ID NO:2.

2. The isolated nucleic acid molecule of claim 1, wherein the nucleic acid molecule encodes a polypeptide consisting of amino acid residues 39 to 94 of SEQ ID NO:2.

3. The isolated nucleic acid molecule of claim 1, wherein the nucleic acid molecule encodes a polypeptide comprising amino acid residues 32 to 94 of SEQ ID NO:2.

4. The isolated nucleic acid molecule of claim 3, wherein the nucleic acid molecule encodes a polypeptide consisting of amino acid residues 32 to 94 of SEQ ID NO:2.

5. The isolated nucleic acid molecule of claim 1, wherein the nucleic acid molecule encodes a polypeptide comprising amino acid residues 1 to 94 of SEQ ID NO:2.

6. The isolated nucleic acid molecule of claim 5, wherein the nucleic acid molecule encodes a polypeptide consisting of amino acid residues 1 to 94 of SEQ ID NO:2.

7. The isolated nucleic acid molecule of claim 1, wherein the nucleic acid molecule encodes a polypeptide comprising amino acid residues 39 to 99 of SEQ ID NO:2.

8. The isolated nucleic acid molecule of claim 7, wherein the nucleic acid molecule encodes a polypeptide consisting of amino acid residues 39 to 99 of SEQ ID NO:2.

9. The isolated nucleic acid molecule of claim 1, wherein the nucleic acid molecule encodes a polypeptide comprising amino acid residues 32 to 99 of SEQ ID NO:2.

10. The isolated nucleic acid molecule of claim 9, wherein the nucleic acid molecule encodes a polypeptide consisting of amino acid residues 32 to 99 of SEQ ID NO:2.

11. The isolated nucleic acid molecule of claim 9, wherein the nucleic acid molecule comprises nucleotides 113 to 316 of SEQ ID NO: 1.

12. The isolated nucleic acid molecule of claim 1, wherein the nucleic acid molecule encodes a polypeptide comprising amino acid residues 1 to 99 of SEQ ID NO:2.

13. The isolated nucleic acid molecule of claim 12, wherein the nucleic acid molecule encodes a polypeptide consisting of amino acid residues 1 to 99 of SEQ ID NO:2.

14. The isolated nucleic acid molecule of claim 12, wherein the nucleic acid molecule comprises nucleotides 20 to 316 of SEQ ID NO: 1.

15. A vector, comprising the nucleic acid molecule of claim 9.

16. A vector, comprising the nucleic acid molecule of claim 12.

17. A recombinant host cell, comprising an expression vector, wherein the expression vector comprises:

a nucleic acid molecule that encodes a polypeptide comprising amino acid residues 32 to 99 of SEQ ID NO:2, a transcription promoter, and a transcription terminator, wherein the promoter is operably linked with the nucleic acid molecule, and the nucleic acid molecule is operably linked with the transcription terminator, wherein the host cell is selected from the group consisting of bacterium, yeast cell, fungal cell, insect cell, avian cell, mammalian cell, and plant cell.

18. The recombinant host cell of claim 17, wherein the host cell is a bacterium.

19. The recombinant host cell of claim 17, wherein the host cell is a yeast cell.

20. The recombinant host cell of claim 17, wherein the host cell is a fungal cell.

21. The recombinant host cell of claim 17, wherein the host cell is an insect cell.

22. The recombinant host cell of claim 17, wherein the host cell is an avian cell.

23. The recombinant host cell of claim 17, wherein the host cell is a mammalian cell.

24. The recombinant host cell of claim 17, wherein the host cell is a plant cell.

25. An expression vector, comprising a nucleic acid molecule that encodes a polypeptide comprising amino acid residues 32 to 99 of SEQ ID NO:2, a transcription promoter, and a transcription terminator, wherein the promoter is operably linked with the nucleic acid molecule, and wherein the nucleic acid molecule is operably linked with the transcription terminator.

26. A method of producing a polypeptide that comprises amino acid residues 32 to 99 of SEQ ID NO:2, comprising culturing recombinant host cells that comprise the expression vector of claim 25, and that produce the polypeptide.

27. The method of claim 26, further comprising isolating the polypeptide from the cultured recombinant host cells.

* * * * *